(12) United States Patent
Stein et al.

(10) Patent No.: US 10,534,894 B2
(45) Date of Patent: Jan. 14, 2020

(54) MOBILE MEDICINE COMMUNICATION PLATFORM AND METHODS AND USES THEREOF

(71) Applicant: BR Invention Holding, LLC, Scottsdale, AZ (US)

(72) Inventors: Stuart Alan Stein, Tucson, AZ (US); Craig Steven Smith, Littleton, CO (US)

(73) Assignee: BR Invention Holding, LLC, Scottsdale, AZ (US)

( * ) Notice: Subject to any disclaimer, the term of this patent is extended or adjusted under 35 U.S.C. 154(b) by 0 days.

(21) Appl. No.: 15/487,955

(22) Filed: Apr. 14, 2017

(65) Prior Publication Data
US 2017/0300654 A1 Oct. 19, 2017

Related U.S. Application Data

(60) Provisional application No. 62/323,005, filed on Apr. 15, 2016.

(51) Int. Cl.
*G06F 19/00* (2018.01)
*H04B 7/185* (2006.01)
(Continued)

(52) U.S. Cl.
CPC ........ *G06F 19/3418* (2013.01); *A61B 5/0022* (2013.01); *A61B 5/024* (2013.01);
(Continued)

(58) Field of Classification Search
None
See application file for complete search history.

(56) References Cited

U.S. PATENT DOCUMENTS

2003/0167257 A1* 9/2003 de Bonet .......... G06F 17/30902
2003/0231238 A1* 12/2003 Chew ...................... H04N 7/15
348/14.02
(Continued)

FOREIGN PATENT DOCUMENTS

WO  WO 2013/171648 A1  11/2013
WO  WO 2014/036640 A1   3/2014
(Continued)

OTHER PUBLICATIONS

U.S. Appl. No. 61/749,618, filed Jul. 10, 2014, Stein et al.
(Continued)

*Primary Examiner* — Donald L Mills
(74) *Attorney, Agent, or Firm* — Duane Morris LLP

(57) ABSTRACT

Telemedicine systems and methods are described. In a telemedicine system operable to communicate with a remote operations center, communications can be transmitted/received using a transceiver having an antenna. The antenna can include first and second di-pole antenna elements, the first di-pole antenna element being vertically polarized and the second di-pole antenna element being horizontally polarized. A controller of the system can establish, using the transceiver, a telemedicine session with the operations center using a Transport Morphing Protocol (TMP), the TMP being an acknowledgement-based user datagram protocol. The controller can also mask one or more transient network degradations to increase resiliency of the telemedicine session. The telemedicine system can include a 2D and 3D carotid Doppler and transcranial Doppler and/or other diagnostic devices, and provides for real-time connectivity and communication between medical personnel in an emergency vehicle and a receiving hospital for immediate diagnosis and treatment to a patient in need.

33 Claims, 16 Drawing Sheets

(51) Int. Cl.

| | | |
|---|---|---|
| *H01Q 1/32* | (2006.01) | |
| *H01Q 21/24* | (2006.01) | |
| *H01Q 9/04* | (2006.01) | |
| *H01Q 1/42* | (2006.01) | |
| *H04L 29/14* | (2006.01) | |
| *H01Q 1/12* | (2006.01) | |
| *H04L 1/00* | (2006.01) | |
| *H01Q 21/28* | (2006.01) | |
| *H01Q 9/28* | (2006.01) | |
| *H01Q 21/26* | (2006.01) | |
| *A61B 5/024* | (2006.01) | |
| *A61B 5/00* | (2006.01) | |
| *H04L 29/08* | (2006.01) | |

(52) U.S. Cl.
CPC ......... *H01Q 1/1214* (2013.01); *H01Q 1/3275* (2013.01); *H01Q 1/42* (2013.01); *H01Q 9/0407* (2013.01); *H01Q 9/28* (2013.01); *H01Q 21/24* (2013.01); *H01Q 21/26* (2013.01); *H01Q 21/28* (2013.01); *H04B 7/18528* (2013.01); *H04L 1/00* (2013.01); *H04L 69/40* (2013.01); *H04L 67/12* (2013.01)

(56) References Cited

U.S. PATENT DOCUMENTS

| | | | |
|---|---|---|---|
| 2005/0066033 A1 | 3/2005 | Cheston et al. | |
| 2005/0185621 A1 | 8/2005 | Sivakumar et al. | |
| 2007/0283262 A1* | 12/2007 | Pally | G06F 17/30887 715/700 |
| 2009/0224983 A1* | 9/2009 | Laroia | H01Q 21/24 343/702 |
| 2010/0198034 A1 | 8/2010 | Thomas et al. | |
| 2012/0016980 A1* | 1/2012 | Rothschild | G06Q 30/0277 709/224 |
| 2012/0059907 A1 | 3/2012 | Vange et al. | |
| 2012/0179037 A1* | 7/2012 | Halmann | A61B 8/4427 600/443 |
| 2013/0142234 A1 | 6/2013 | Ohayon et al. | |
| 2013/0295841 A1* | 11/2013 | Choi | H01Q 3/24 455/12.1 |
| 2013/0346593 A1* | 12/2013 | Setlur | H04L 29/14 709/224 |
| 2014/0077956 A1 | 3/2014 | Sampath et al. | |
| 2014/0142060 A1 | 5/2014 | Stein et al. | |
| 2014/0160432 A1* | 6/2014 | Brown, Jr. | G06K 9/0061 351/208 |
| 2014/0194740 A1 | 7/2014 | Stein et al. | |
| 2014/0289381 A1* | 9/2014 | Morton | H04L 41/5025 709/221 |
| 2014/0355446 A1 | 12/2014 | Altman | |
| 2015/0119652 A1 | 4/2015 | Hyde et al. | |
| 2016/0030001 A1 | 2/2016 | Stein et al. | |
| 2016/0055305 A1 | 2/2016 | Hiriyannaiah et al. | |
| 2017/0024537 A1* | 1/2017 | Ferlito | G06F 19/3418 |
| 2017/0076057 A1* | 3/2017 | Burton | G06F 19/3418 |
| 2017/0179596 A1* | 6/2017 | Diaz | H01Q 3/46 |

FOREIGN PATENT DOCUMENTS

| | | |
|---|---|---|
| WO | 2014070993 A1 | 5/2014 |
| WO | WO 2016/038611 A1 | 3/2016 |

OTHER PUBLICATIONS

U.S. Appl. No. 61/833,802, filed Jul. 10, 2014, Stein et al.
Jun. 10, 2017 International Search Report and Written Opinion from PCT International Application No. PCT/US2017/027658.
Jan. 24, 2019 Supplemental European Search Report issued by European Patent Office regarding European Patent Application No. 17783250.8.

* cited by examiner

MOBILE MEDICINE COMMUNICATION PLATFORM AND METHODS AND USES THEREOF

CROSS REFERENCE TO RELATED APPLICATIONS

This application claims priority to and the benefit of U.S. Provisional Application No. 62/323,005, filed on Apr. 15, 2016, which is hereby incorporated by reference.

This application also discloses products and references, such as (A) PCT Application No. PCT/US2013/067713, which was filed on Oct. 31, 2013 and entitled "Novel System for Emboli Detection in the Brain Using a Transcranial Doppler Photoacoustic Device Capable of Vasculature and Perfusion Measurement;" (B) U.S. patent application Ser. No. 14/674,411, which was filed on Mar. 31, 2015 and entitled "Helmet Apparatus and System with Carotid Collar Means On-Boarded;" (C) U.S. patent application Ser. No. 14/070,264, filed on Nov. 1, 2013 and entitled "Emboli detection in the brain using a transcranial Doppler photoacoustic device capable of vasculature and perfusion measurement;" (D) U.S. patent application Ser. No. 14/084,039, which was filed on Nov. 19, 2013 and entitled "Method and Device for Identification of One Carbon Pathway Gene Variants as Stroke Risk Markers, Combined Data Mining, Logistic Regression, and Pathway Analysis;" (E) U.S. Provisional Application No. 61/720,992, which was filed on Oct. 31, 2012; (F) U.S. Provisional Application No. 61/794,618, which was filed on Jan. 7, 2013; and (G) U.S. Provisional Application No. 61/833,802, which was filed on Jun. 11, 2013, and the disclosures of such products and references are hereby incorporated by reference.

TECHNICAL FIELD

Aspects described herein generally relate to devices and methods mobile telemedicine, including mobile telemedicine devices and methods for treating traumatic event in the brain, for example, a stroke, cerebrovascular accident (CVA), concussion or a seizure, as well as trauma in general and other acute medical disorders.

BACKGROUND AND RELATED ART

Strokes impact approximately 795,000 Americans each year. Of these, 30% may involve the large vessels, the middle cerebral arteries, the basilar artery, and the carotid arteries. Only 10% of these patients receive definitive early diagnosis and therapy A stroke occurs when a vessel in the brain ruptures or is blocked by a blood clot. Although progress has been made in reducing stroke mortality, it is the fourth leading cause of death in the United States. Moreover, stroke is the leading cause of disability in the United States and the rest of the world. In fact, 20% of survivors still require institutional care after 3 months and 15% to 30% experience permanent disability. This life-changing event affects the patient's family members and caregivers. With an aging US population, the situation will only become more desperate. More significant disability may be associated with large vessel obstruction and large vessel strokes.

Individuals afflicted with a stroke must receive immediate medical attention or risk suffering long term effects. However, many individuals suffering a stroke do not receive medical attention in time or are not diagnosed with a stroke. In some instances, patients are rushed to the closest hospital, but not the appropriate hospital equipped for treating a stroke patient. A hospital may be inappropriate because of inadequate diagnostic equipment, or lack of immediate access to required diagnostic and imaging testing. Also, the hospital may lack medical professionals, such as neurologists or interventional vascular specialists who are trained to give expert interpretation and necessary and warranted therapies. By the time the patient is diagnosed with a stroke, it may be discovered that the patient is at the wrong hospital and the potential for long term affects increases. In a stroke, 2 million nerve cells die per minute. Therefore, time is of the essence when diagnosing and treating stroke patients. It is best to start treatment within an hour of stroke onset.

However, definitive stroke treatment using, for example, clot buster therapy or brain or neck vessel clot removal or clot bypass can be initiated with stroke reversal or reduction in severity and morbidity and elimination of mortality. A golden hour from stroke onset to therapy in selected strokes, particularly those involving the large vessels is recommended, but blood thinner therapy up until 4.5 hours and clot removal up until 6-8 hours but with diminished efficacy of the treatment after the first hour. Early diagnosis and therapy is particularly important for stroke involving the large vessels of the brain and neck (i.e., large vessel obstructions) and only 10% of eligible patients receive definitive therapy. These strokes have the highest potential for significant morbidity and mortality. Adverse factors may affect stroke care. In some instances, definitive therapy may not be available because the stroke has already occurred or is too large and cannot be reversed.

Despite national protocols for stroke care with improved prognosis, the process and logistics of patient care from time of onset (T1) of Stroke or traumatic brain injury (TBI) Episode through initial hospital encounter and emergent and acute care during the acute episode (T 'n') in the Emergency Department is inconsistent nationwide. Other inconsistencies with variability and incompleteness nationwide include the capture, collection and communication of pertinent patient data, communication among the entire community of 1st responders and ER physicians/radiologists and staff, and a neurological examination. As such, definitive diagnosis and treatment may not occur on initial presentation at the emergency department. Disorders that are not stroke may not be identified, but still receive potentially dangerous therapy for stroke. Thus, optimal, personalized care is not being done. Hence, there may be delivery of patients to inappropriate sites, unsafe/unwarranted treatment, delayed treatment, inability to treat due to time limitations, increased brain damage, and poorer prognosis.

If the patient arrives late, or is seen outside of the acceptable time window, or the patient has too many other medical risk factors to allow definitive therapy, then these factors may lead to complications, including brain hemorrhage. Also, screening of patients with stroke causing conditions is often not done. This can lead to a stroke, which may be preventable. Traumatic brain injury occurs in 1.7M patients per year, including but not limited to concussion and brain hemorrhage. These may be mild, moderate, or severe. In the context of traumatic brain injury, vascular obstruction, narrowing due to vessel spasm, and vessel tearing of brain and neck vessels place this group of disorders in those needing evaluation as well as those needing attention to their vascular efficacy. The system and methods of the exemplary embodiments described herein will be useful for identification and diagnosis and early therapy for this group of disorders, as well as other brain injuries or other medical conditions.

SUMMARY

As an overview, the present disclosure provides a systems and methods for assessing a patient for one or more traumatic brain injuries, such as for a stroke, and other neurological disorders while in transport in an emergency vehicle, such as an ambulance, emergency helicopter, airplane, train, boat and/or other vehicle. The disclosure is not limited to in-transit assessments and can include assessing a patient in a diagnostic facility such as an urgent care facility, doctor's office, clinics, nursing homes, fire station, police station, or another facility. The telemedicine system can also be a portable configuration that can be brought into a facility by emergency personnel when assessing a patent.

In consideration of the above problems, in accordance with one aspect disclosed herein, a telemedicine system operable to communicate with a remote operations center, comprising a transceiver configured to transmit or receive one or more communications via an antenna having first and second di-pole antenna elements, the first di-pole antenna element being vertically polarized and the second di-pole antenna element being horizontally polarized; and a controller connected to the transceiver and configured to establish, using the transceiver, a telemedicine session with the operations center using a Transport Morphing Protocol (TMP), the TMP being an acknowledgement-based user datagram protocol; and mask one or more transient network degradations to increase resiliency of the telemedicine session.

In an exemplary embodiment, the controller is configured to (a) adjust data send rate of the telemedicine session to reduce packet loss and reduce the resending of packets of the telemedicine session and (b) switch between cellular communication and satellite communication upon detecting a transient network loss.

In an exemplary embodiment, the controller is configured to encrypt communications of the telemedicine session such that the telemedicine session is a secure telemedicine session; the controller being connected to a router, the router being connected to a cellular modem and two different kinds of satellite modems.

In an exemplary embodiment, the two different kinds of satellite modems include a first modem configured to transmit data over a Ku or Ka band antenna and a second modem configured to transmit data over an L-Band antenna.

In an exemplary embodiment, a vehicle comprising the telemedicine system, a plurality of wheels, and a motor configured to drive the plurality of wheels.

In an exemplary embodiment, the telemedicine system further comprises a router connected to the transceiver, the router being configured to route communications between the controller and the transceiver, and wherein the controller is configured to controller the router to dynamically switch between the two or more wireless communication protocols.

In an exemplary embodiment, the telemedicine system further comprises a satellite transceiver configured to transmit or receive one or more satellite communications to/from one or more orbiting satellites.

In an exemplary embodiment, the controller is configured to control the telemedicine system to dynamically switch communications of the telemedicine session between the transceiver and the satellite transceiver.

In an exemplary embodiment, the telemedicine system further comprises a router connected to the transceiver and the satellite transceiver, wherein the controller is configured to control the router to dynamically switch the communications of the telemedicine session between the transceiver and the satellite transceiver.

In an exemplary embodiment, the first di-pole antenna element includes first and second vertically-arranged antenna radiators, the first vertically-arranged antenna radiator being arranged orthogonal to the second vertically-arranged antenna radiator, wherein the first vertically-arranged antenna radiator and the second vertically-arranged antenna radiator intersect each other.

In an exemplary embodiment, the second di-pole antenna element includes first and second horizontally-arranged antenna radiators, the first and the second horizontally-arranged antenna radiators being arranged in a same horizontal plane.

In an exemplary embodiment, the first di-pole antenna element includes first and second vertically-arranged antenna radiators, the first vertically-arranged antenna radiator being arranged orthogonal to the second vertically-arranged antenna radiator, wherein the first vertically-arranged antenna radiator and the second vertically-arranged antenna radiator intersect each other; and the second di-pole antenna element includes first and second horizontally-arranged antenna radiators, the first and the second horizontally-arranged antenna radiators being arranged in a same horizontal plane.

In an exemplary embodiment, the first and second di-pole antenna elements are enclosed in a single radome.

In an exemplary embodiment, the telemedicine system further comprises one or more medical imaging modalities configured to generate one or more medical images of a patient, wherein controller is configured to transmit the one or more medical images to the operations center using the transceiver; a satellite transceiver comprising a VSAT modem connected to a flat panel phased array satellite terminal comprising at least one antenna configured to communicate over Ku or Ka bands, an L-Band satellite modem connected to an L-band satellite antenna, and a router connected to both the VSAT modem and the L-Band satellite modem; the controller being configured to monitor signal strength of the VSAT modem and the L-Band modem and to cause the router to dynamically switch between the modems based on the monitored signal strengths.

In accordance with another aspect disclosed herein, a telemedicine system operable to communicate with a remote operations center and one or more medical facilities, comprising a transceiver configured to transmit or receive one or more communications using the two or more wireless communication protocols via an antenna having first and second di-pole antenna elements, the first di-pole antenna element being vertically polarized and the second di-pole antenna element being horizontally polarized; a satellite transceiver configured to transmit or receive one or more satellite communications to/from one or more orbiting satellites; a router connected to the transceiver and the satellite transceiver, the router being configured to route communications to and from the transceiver and the satellite transceiver and to dynamically switch between the two or more wireless communication protocols; and a controller connected to the transceiver and the satellite transceiver via the router, the controller being configured to establish, using at least one of the transceiver and the satellite transceiver, a telemedicine session with the operations center and the one or more medical facilities using a Transport Morphing Protocol (TMP), the TMP being an acknowledgement-based user datagram protocol; and mask one or more transient network degradations to increase resiliency of the telemedicine session.

In an exemplary embodiment, the controller is configured to adjust data send rate of the telemedicine session to reduce packet loss and reduce the resending of packets of the telemedicine session.

In an exemplary embodiment, the controller is configured to encrypt communications of the telemedicine session such that the telemedicine session is a secure telemedicine session.

In an exemplary embodiment, the first di-pole antenna element includes first and second vertically-arranged antenna radiators, the first vertically-arranged antenna radiator being arranged orthogonal to the second vertically-arranged antenna radiator, wherein the first vertically-arranged antenna radiator and the second vertically-arranged antenna radiator intersect each other.

In an exemplary embodiment, the second di-pole antenna element includes first and second horizontally-arranged antenna radiators, the first and the second horizontally-arranged antenna radiators being arranged in a same horizontal plane.

In an exemplary embodiment, the first di-pole antenna element includes first and second vertically-arranged antenna radiators, the first vertically-arranged antenna radiator being arranged orthogonal to the second vertically-arranged antenna radiator, wherein the first vertically-arranged antenna radiator and the second vertically-arranged antenna radiator intersect each other; and the second di-pole antenna element includes first and second horizontally-arranged antenna radiators, the first and the second horizontally-arranged antenna radiators being arranged in a same horizontal plane.

In an exemplary embodiment, the first and second di-pole antenna elements are enclosed in a single radome.

In an exemplary embodiment, the telemedicine system further comprises a raman spectroscope configured to perform molecular analysis by raman spectroscopy and/or other molecular diagnostic techniques, the molecular analysis being performed on at least one of: serum, plasma, blood, blood cells, cerebrospinal fluid, urine, cells, and tissue, wherein the controller is configured to diagnose and define, based on the molecular analysis, at least one of: acute stroke, acute stroke subtype, concussion, and traumatic brain injury.

In an exemplary embodiment, the molecular analysis increases the precision of the diagnosis.

In an exemplary embodiment, the satellite transceiver comprises a VSAT modem connected to a flat panel phased array terminal comprising at least one satellite antenna configured to communicate over Ku or Ka bands.

In an exemplary embodiment, the satellite transceiver comprises an L-Band satellite modem connected to an L-band satellite antenna; the router being connected to both the VSAT modem and the L-Band satellite modem; the controller being configured to monitor signal strength of the VSAT modem and the L-Band modem and to cause the router to dynamically switch between the modems based on the monitored signal strengths.

In an exemplary embodiment, the telemedicine system further comprises a 2D and 3D carotid Doppler and transcranial Doppler that are connected to the telemedicine system.

In an exemplary embodiment, the telemedicine system operates in a vehicle in a rural, extreme rural, urban, maritime or aviation environment.

In an exemplary embodiment, the vehicle is selected from the group consisting of ambulance, helicopter, bus, train, car, boat, oil rig, and airplane.

In an exemplary embodiment, the telemedicine system further comprises one or more devices used to evaluate vitals and/or brain condition of a patient that are connected to the telemedicine system, and the telemedicine system is configured to collect and transmit audio, video or other data from the one or more devices to the operations center.

In an exemplary embodiment, the one or more devices is a EEG device, intracranial pressure measurement device, blood pressure measurement device, brain hemorrhage diagnostic device, non-brain diagnostic device, blood diagnostic test device; bodily fluid diagnostic test device, or a combination thereof.

In an exemplary embodiment, the collected and transmitted audio, video or other data is reviewed in real-time by at least one physician to diagnosis and/or treat the patient suffering from stroke, a traumatic brain injury, a neurological disorder, an organ system medical disorder, or a combination thereof.

In an exemplary embodiment, the controller is configured to implement an enhanced transport layer that mitigates high-latency of packets across at least one satellite link and at least one cellular wireless link, and provides Quality of Service (QoS) and wide-area network (WAN) optimization across the at least one satellite link and the at least one cellular wireless link, and wherein the operations center is configured to provide real-time communication between at least one medical personnel in a vehicle with the telemedicine system, the at least one physician, and at least one medical personnel at a receiving hospital.

In an exemplary embodiment, the telemedicine system further comprises at least one teleconferencing solution, the at least one teleconferencing solution is connected to the telemedicine system at an application layer, and rides on top of fully redundant physical, network and transport layers with no single point of failure and with at least 99.99% availability.

BRIEF DESCRIPTION OF THE FIGURES

The accompanying drawings, which are incorporated herein and form a part of the specification, illustrate the aspects of the present disclosure and, together with the description, further serve to explain the principles of the aspects and to enable a person skilled in the pertinent art to make and use the aspects. The drawings are for illustration purposes only and are not necessarily drawn to scale.

The exemplary aspects of the present disclosure will be described with reference to the accompanying drawings. The drawing in which an element first appears is typically indicated by the leftmost digit(s) in the corresponding reference number.

DETAILED DESCRIPTION

Figure 1:
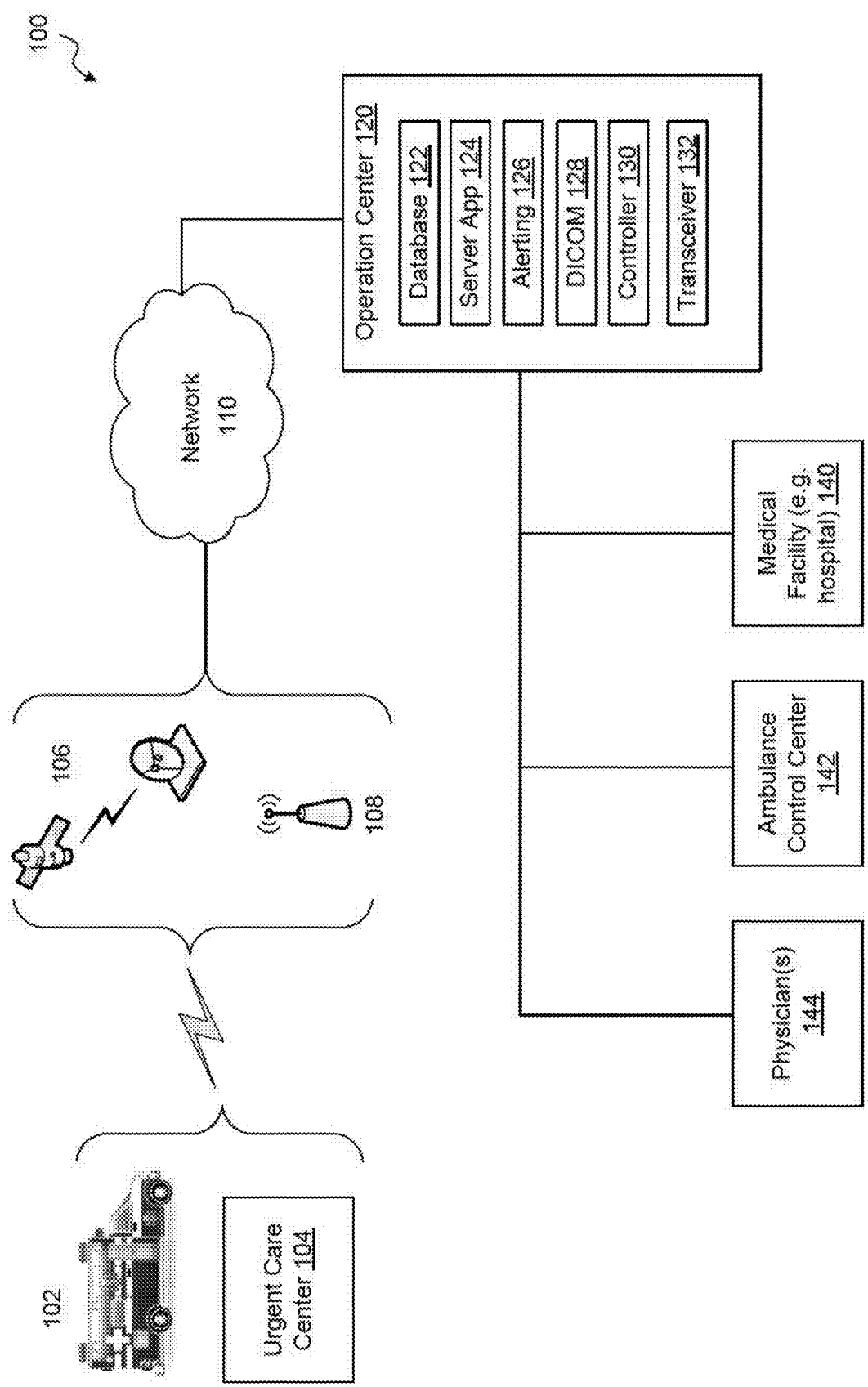
FIG. 1 illustrates a telemedicine system environment according to an exemplary embodiment of the present disclosure.

In the following description, numerous specific details are set forth in order to provide a thorough understanding of the aspects of the present disclosure. However, it will be apparent to those skilled in the art that the aspects, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring aspects of the disclosure.

As an overview, the present disclosure provides a systems and methods for assessing a patient for one or more traumatic brain injuries, such as for a stroke, and other neurological disorders while in transport in an emergency vehicle, such as an ambulance, emergency helicopter, airplane, train, boat and/or other vehicle. The disclosure is not limited to in-transit assessments and can include assessing a patient in a diagnostic facility such as an urgent care facility, doctor's office, clinics, nursing homes, fire station, police station, or another facility. The telemedicine system can also be a portable configuration that can be brought into a facility by emergency personnel when assessing a patent.

In the treatment of a medical condition (e.g., stroke), adverse factors related to time-sensitive, early, reliable, accurate, and safe stroke diagnosis and therapy affect the outcome of treatment. Expert neurological and neuroradiological examination with stroke telemedicine using audio/video teleconferencing in hospital emergency departments, including stroke ready and primary and comprehensive stroke centers can be used to reduce the time to definitive diagnosis, to initiation of clot buster and/or clot removal, and improved prognosis (in some cases). Given the time critical nature of stroke diagnosis and therapy, a prehospital, cloud based solution can be implemented in ambulances or other emergency vehicles. As such, patients may be diagnosed earlier, have therapy initiated earlier, with neurological diagnosis at time of initial patient contact and a seamless continuum of care from pickup to hospital.

Strokes with large vessel obstructions (LVO) can include obstructions in the middle cerebral arteries, the basilar artery, and the carotid artery. These strokes comprise about 30% of acute strokes and can cause the most severe neurological disability unless diagnosed and treated early, when appropriate. The earlier the diagnosis and the earlier the treatment, if warranted with clot buster and/or clot retrieval, particularly with stent retrievers, the better the chance of reversal or neurological abnormalities and stroke or reduced neurological disability or death risk. Prehospital diagnosis, delivery to the appropriate facility, and preparation and expertise at the target hospital facility, particularly a comprehensive stroke center, is crucial for the acute and future prognosis of the patient. In the exemplary embodiments described herein, the pre-hospital environment, including ambulances and other vehicles and urgent care centers, is optimized to identify large vessel obstructions and foster earlier and appropriate therapy.

Stroke, including early onset stroke before age 55 years, is predisposed to by, including but not limited to prior stroke, prior heart attack, rhythm disturbance of the heart, diabetes, obesity, race, high lipids, genetic disorders that cause stroke (including molecular abnormalities), and complicated migraine. Early identification of patients with these predisposing disorders by neurological examination and non-invasive neck and brain blood vessel screening with ultrasound may lead to identification of patients at risk for impending stroke, as well as initiation of therapies that may be useful in preventing stroke, i.e. high blood pressure, high lipid or heart rhythm disturbance management. In exemplary embodiments, telemedicine systems and method can be used in hospital or in outpatient settings for patient management.

Seizures with or without residual weakness and other neurological signs and symptoms can mimic strokes. The acute therapy for these is very different than for strokes and diagnosis of stroke in these situations may lead to treatment with clot buster. The latter has 4-10% risk of brain hemorrhage in all cases and would not be warranted in seizure cases. Neurological examination in the acute situation as well as EEG tied to the telemedicine system may be useful and diagnostic.

Traumatic brain injury (TBI) and stroke may have increased intracranial pressure, which is needed for diagnosis and potential acute and subacute therapy. In addition to the transcranial Doppler, ultrasound measures to look at pressure on the eye nerve as well as separate devices that measure intracranial pressure externally may be employed with the telemedicine system.

Trauma, stroke, traumatic brain injury (TBI), other acute neurological disorders, and other clinical disorders may need emergent or urgent care or home or clinic diagnosis. Devices that look at the ear for blood or infection (e.g., an otoscope), the mouth for conditions, including but not limited to pharyngeal inflammation and trauma, can be interfaced with telemedicine systems. The same is true for stethoscopes for evaluation of the heart and lungs, which can be interfaced with telemedicine systems. Similarly, ophthalmoscopes can be interfaced for eye conditions and increased brain pressure, reflected in the eye nerve. Electrocardiography can also be interfaced with telemedicine systems.

A primary barrier for giving clot buster in stroke early and pre-hospital situations is the need for a CT scan, which is used to determine if there is a brain bleed. The latter is an absolute contraindication to clot buster. The presence of hemorrhage starts a different treatment protocol potentially in ambulance and at the hospital. As explained in the various exemplary embodiments herein, the telemedicine systems and methods ameliorate these issues.

Telemedicine can include the use of telecommunication and information technology to support health care when distance separates the patient from the caregiver. Telemedicine has been fostered by the development of computer and connectivity equipment and software, dedicated IT development and support at hospitals, advanced software for telemedicine. Telemedicine may involve wide area networks (WAN), local area networks (LAN) Internet, private and public networks, virtual private networks, wired and/or wireless networks, municipal wireless and/or wired broadband networks, cellular networks, metropolitan networks. Telemedicine networks can be implemented in concert with hosts that may involve any device, including a computer. These devices may involve security tools, particularly in a clinical environment.

Initiation of telemedicine can include Tele-stroke diagnosis and measurements. The quality and definitive telemedicine in an ambulance depends on WiFi, commercial wireless carriers, and associated dependence on cell towers, results in connectivity issues, including, for example, the inability to connect, persistent connectivity, signal loss, bandwidth availability and quality of service. These issues can be more prevalent within rural regions and busy urban areas and quality audio and video may be reduced. Other types of data transfer, including images may also have limitations in this setting. For example, some telemedicine implementations have been tested and have only achieved consultation success rate of approximately a 40%. This success rate was impacted by connectivity initiation and persistence, as well as poor quality audio and video. The deployment of ambulance systems that include mobile CT scanner devices have also experienced these issues of connectivity degradation, bandwidth, poor quality audio and video transmissions, and low success rates.

The exemplary embodiments described herein are directed to hardware and software solutions for improved telemedicine, having more effective and reliable connectivity. As described herein, ambulance telemedicine systems for stroke, TBI, and other neurological conditions may address and diagnosis at the time of first response, transport to the appropriate medical facility (e.g., hospital), and allow for the preparation for rapid definitive intervention with the appropriate diagnosis, personnel, & equipment for treatment when the patient arrives at the emergency facility.

The systems and methods of the present disclosure can perform remote neurological examination and determination of parameters indicative of, for example, a possible stroke or a stroke risk patient. The results of the assessment allow for a patient to then be redirected to the nearest stroke treating hospital, thus saving valuable treatment time, allowing the preparation for, and evaluation of, the safest and most appropriate diagnosis and treatment. As would be understood by one of ordinary skill in the relevant arts, this disclosure is not limited to brain injuries such as strokes, and can be applied to other medical conditions.

In exemplary embodiments of the present disclosure, the system and methods include telemedicine and an ecosystem of care for stroke, traumatic brain injury and other neurological disorders and trauma for clinical and neurological examination and determining blood flow velocity and brain neck vessel obstructions, and/or generate one or more medical images of the patient using one or more imaging modalities.

The telemedicine system can include measurement devices configured to perform high quality, telemedicine neurological or non-neurological examinations in real time, visualize and capture audio input directly, collect measurements for brain and neck vessel function and physiology, and deliver integrated care for a patient in emergency vehicles (e.g., ambulances), acute care situations, and also non-emergent care locations.

In exemplary embodiments, the clinical examinations, including, but not limited to, the National Institute of Health (NM) Stroke Scale, neurological examination, and/or other clinical examination data related to brain and other organ systems, and/or the measurements are collected while the patient is in transport, including the electronic health record of the patient with the examination results (e.g., in text format and by audio/video communication) and the measurements are sent to an operations center and/or more neurological and/or radiological experts at one or more remote locations, using advanced health information technology techniques. The operations center and/or neurological and radiological teams can analyze the measurements and/or one or more patent images to determine whether a stroke has or is occurring, and can provide instructions to the transport team. The operations center can also communicate with one or more emergency vehicle control centers and/or or medical facilities to determine the appropriate facility to route the emergency vehicle to.

In an exemplary embodiment, a textual electronic health record with examination information and interpretation of other physiological measurements are provided to the ambulance personnel, the appropriate hospital to which the patient will be transported, and stroke and other personnel at that facility. This allows for the patient can be transported to the appropriate facility and for preparations and decisions to be made prior to the transport's arrival.

Upon arrival at the appropriate facility (e.g., hospital or emergency room), warranted and appropriate medical (e.g., stroke) diagnostics and treatments can begin immediately, thus saving valuable time. Therapy for the patients can be selected and increase the positive outcomes, including stroke reversal and reduced stroke severity, as well as reducing mortality. In assessing stroke, identifying abnormalities or reduced blood flow in neck or brain blood vessels are important because of the associated urgency with addressing these conditions.

In exemplary embodiments, one or more imaging modalities can be used to assess the patient, including ultrasound imaging such as, carotid and/or transcranial Doppler, photoacoustic spectroscopy, and phased array ultrasound. The Doppler imaging can include both two-dimensional (2D) and three-dimensional (3D) imaging, transcranial Doppler (TCD), and/or transcranial color coded Doppler (TCCD). The imaging modalities are not limited thereto and can include, for example (but not limited to), computed tomography (CT) imaging, positron emission tomography (PET) imaging, single-photon emission computed tomography (SPECT), X-ray imaging, magnetic resonance imaging (MRI), nuclear magnetic resonance imaging (NMRI), magnetic resonance tomography (MRT), raman spectroscopy, and/or another imaging technology as would be understood by those skilled in the relevant arts.

In an exemplary embodiment, the imaging device can be configured to transmit energy to a region of interest, such as in the patient's head and neck regions and/or cranial and carotid regions. In some embodiments, ultrasound transducers can be placed on the patient to transmit and sense ultrasound waves to characterize a patient's brain and measure blood parameters. The imaging devices can collect ultrasonic waves and process the corresponding data to assess the patient (e.g., blood flow velocity). In exemplary embodiments, the telemedicine system can be configured to measure molecular indices to assess the patient in addition to, or as an alternative to capturing a medical image.

In operation, the telemedicine systems of the present disclosure can be implemented in an emergency vehicle and can be configured to collect direct visual and audio information and direct Digital Imaging and Communications in Medicine (DICOM) and other modality information about the blood flow in the head and neck region of the patient. The telemedicine systems can be configured to transmit the corresponding data to a remote location, such as an operations center of the telemedicine system and/or a medical facility (e.g., hospital).

As discussed further below, the telemedicine systems of the present disclosure can also be used to collect and transmit direct visual and audio information and data from other devices that reflect on brain function and other organ systems. Thus, the systems and methods of the disclosure provide remote, real-time, stroke diagnostics, as well as diagnostics applicable to other disorders that may mimic stroke or that may affect neck and brain blood flow, such as heart attack or diffuse infection (sepsis) or traumatic brain injury and concussions. The systems and methods of the disclosure are integrated into a telemedicine ecosystem, allowing for brain damage to be evaluated in real-time upon first-contact with patients, with a particular focus on definitive neurological examination and the narrowing or obstruction of large neck and brain blood vessels. Systems and methods of the disclosure capture neurological and neurovascular information and data that is rapidly transmitted to a data and operations center for analysis by licensed neurologists, radiologists, and related professionals.

Transmitting 3D and 2D images of carotid and other neck arteries, and collecting blood flow velocities and other parameters on large or medium sized brain bloods vessels, and during patient transport, the systems and methods of the disclosure allow professionals to render a diagnosis, inform Emergency medical technician (EMT) personnel, and alert and discuss with the appropriate emergency room or stroke center to prepare for the pre-diagnosed patient. Thus, the present disclosure helps to differentiate among brain trauma, strokes, seizures, and intoxication, and hyper/hypoglycemic events, so that patients arrive at the right location, already diagnosed, saving valuable time and preventing the loss of up to two-million brain cells per minute in the event of a severe stroke.

In one or more embodiments, the systems and methods of the disclosure deliver energy to a region of interest through a patient's head and neck region. In some embodiments, energy may be delivered by an ultrasound device.

Thus, the devices and methods of the disclosure can be used to preventatively identify pre-stoke and stroke conditions that can lead to life-saving interventions-ranging from immediate removal of vascular obstructions to less invasive dietary and lifestyle changes. The present disclosure helps assure rapid treatment that saves lives, brain cells, expensive and time-consuming rehabilitation. In addition, pain, suffering, and other deleterious brain-related consequences are reduced.

Exemplary embodiments include system and methods for diagnosing strokes, traumatic brain injury, other neurological disorders, and other clinical disorders in patients acutely in prehospital environments, and potentially, preventatively. The devices, systems, and methods also identify and define vessels abnormalities in patients in preventative settings that are at stroke risk. There are two types of strokes: hemorrhagic or ischemic. An ischemic stroke occurs as a result of an obstruction within a blood vessel supplying blood to the brain. It accounts for 87 percent of all stroke cases. A hemorrhagic stroke occurs when a blood vessel ruptures and spills blood into brain tissue. The treatment approaches are different for stroke without hemorrhage versus stroke with hemorrhage. For example, stroke patients without hemorrhage may require vessel opening therapies with intravenous thombolytics or intra-arterial clot busters (e.g., tissue plasminogen activator (tPA)) or catheter-based interventional clot removal. The latter treatments are dangerous and not warranted for hemorrhagic stroke.

Treating an acute stroke patient is time sensitive. However, many patients do not receive the required medical attention in time. The present invention provides devices and methods for early detection and diagnosis of stroke patients to afford the possibility for appropriate and safe treatment modalities acutely and to limit the occurrence of secondary complications, including brain hemorrhage. Further, this device provides a simple means for application to collect physiological data without significant technical expertise or time commitment by emergency technical providers. Thus, a patient may be recognized as suffering from cardiac arrest, but the presence of a stroke may go undetected.

An ischemic stroke is the result of neuronal death due to lack of oxygen, a deficit that produces focal brain injury. This event is accompanied by tissue changes consistent with an infarction that can be identified with neuroimaging of the brain. Strokes are usually accompanied by symptoms, but they also may occur without producing clinical findings and be considered clinically silent.

Both acute and chronic conditions may result in cerebral ischemia or stroke. Acute events that can lead to stroke include cardiac arrest, drowning, strangulation, asphyxiation, choking, carbon monoxide poisoning, and closed head injury. More commonly, the etiology of stroke is related to chronic medical conditions including large artery atherosclerosis, atrial fibrillation, left ventricular dysfunction, mechanical cardiac valves, diabetes, hypertension and hyperlipidemia.

Regardless of the cause, prompt recognition of symptoms and urgent medical attention are necessary for evaluation and institution of clinically warranted thrombolytic or clot busting therapy through the veins or catheter and stent retriever related intra-arterial clot busting therapy or clot removal to be considered and provided.

Time is of the essence for beginning therapy and performing suitable evaluations. Clinical imaging and other testing may be performed during that time. Because time is so critical for performing neurological examination, imaging and other testing needs to occur during a critical time window. This has prompted increased education and awareness campaigns for the public and emergency services providers about the signs and symptoms of stroke. This has also established national protocols for acute stroke diagnosis and treatment to be adopted at increasing number of United States hospitals and their emergency departments. The present disclosure is built on novel enhancement of existing established National protocols. The arrival of a stroke patient in the emergency room (ER) must be viewed as a true emergency, and the patient should receive the highest priority. On arrival to the ER, identification of the patient with a potential stroke should prompt the collection of several important data points: time the patient was last known to be neurologically normal; detailed neurological exam, including the use of National Institutes of Health Stroke Scale (NIHSS); determination of the neurological diagnosis and the severity of the neurological dysfunction; time known to last be neurologically normal; serum glucose level; general metabolic screening; blood count and blood clotting status screening; recent and remote medical and neurological history, with particular attention to diabetes, hypertension, recent surgery or head injury; prior bleeds in brain and other tissues, and epilepsy; current medications, allergies, and baseline CT scan of head for stroke, hemorrhage or other condition. Potential stroke and determination of risk and eligibility or clot buster or intervention brain or neck artery therapy are derived from this evaluation. Rapid, safe and appropriate therapy for specific patients is fostered by rapid assessment as documented above.

The American Heart Association standards mandate for evaluation of clot buster and endovascular therapy, a neurological examination that includes a NIH stroke scale, a CT scan to evaluate for stroke, stroke size, and presence or absence of brain hemorrhage, as well as vessel imaging of neck and brain. Protocols for stroke evaluation and/or treatment may be variable across centers of similar type, i.e. primary stroke centers or comprehensive strokes centers or primary stroke centers that do not have full stroke treatment capacities (endovascular capabilities for clot retrieval versus no capacity), primary stroke centers versus stroke ready vs. non-stroke ready hospitals, versus comprehensive stroke centers.

Recently, since neurological evaluation with stroke specialists may not be uniformly available rapidly or geographically, stroke telemedicine using tele-neurologists at remote locations with special mobile audio video equipment in the Emergency Department or other settings can provide review of all relevant data, neurological examination, and CT scan review, while advising Emergency physicians about appropriate and safe therapies. Efficacy and quality of the neurological examination and radiological interpretation by offsite neurologists is similar; stroke identification and time to deliver clot buster to appropriate patients and the occurrence of clot buster side effects (e.g., hemorrhage) is similar to hospitals that have regular in person neurological evaluation. This is helpful within the time window and similar in concept to the rapid determination of neurological examination and physiological measures pre-hospital in the current application.

In exemplary embodiments of the present disclosure, the systems and methods can include a telemedicine solution for ambulances that combines unique proprietary and standards-based products delivering uninterrupted data signals between telemedicine equipped ambulance and critical-care providers. In an exemplary embodiment, dual di-pole antennas provide continuous Physical layer signaling to mobile endpoints (ambulances) regardless of terrain, locality, and available cellular provider.

In exemplary embodiments, the Transport layer protocol of the OSI model provides application persistence even in low coverage and highly congested situations with reduced losses in connectivity. This transport layer protocol can also be configured to be plug-and-play ready.

In exemplary embodiments, the systems and methods include a high-quality audio/video platforms (hardware and/or software) which are agnostic and can be easily interfaced with other software and hardware, and with ease of use can be combined with a software vehicle; special, ruggedized router; a ruggedized laptop; and/or specialized antennas. The embodiments described herein can be implemented in both rural and urban environments, in forward military positions, and in maritime environments (including, but not limited to, ships and oil rigs and aviation environments) for stroke and other telemedicine systems, and be used in fast moving (e.g., up to approximately 90 miles per hour) emergency vehicles (e.g., ambulances) and in aviation vehicles (including, but not limited to, planes and helicopters).

In an exemplary embodiment, neurological examination and physiological measurements can be performed using carotid and transcranial Doppler devices. The measurements can be performed in real time by telemedicine to operations centers staffed by expert tele-radiologists and tele-neurologists that also provide real time analysis to allow for stroke patient transport to appropriate stroke centers that are prepared to provide rapid diagnostics and appropriate and warranted treatment.

In exemplary embodiments, an ambulance personnel or EMTs (Emergency Medical Technicians) can evaluate a stroke in the field or on the ambulance's way to a medical facility. The ambulance can be outfitted with a telemedicine system configured to send valuable telemetry to the medical facility ahead of the patient's arrival. In exemplary embodiments, the operations include dispatching an ambulance to the patient. A neurological examination using, for example (but not limited to), the NIH stroke scale would be performed. A Transcranial Doppler of Bilateral Middle Cerebral Arteries and Carotid Arteries and then Basilar Artery can be performed. These arteries are the large arteries that can cause the most severe stroke and that would be amenable to intravenous or intra-arterial therapy. In exemplary embodiments, depending on the length of the ambulance ride, the neurological examination and ultrasound examinations could be repeated or could be continuous to provide ongoing data about the patient during transport.

The data can be sent to an operations center where it would be rapidly processed. The processed data would be rapidly evaluated by experienced neurologists and radiologists at the operations center at a power of care and in real time, 24-7. The analysis of this data would be provided to the ambulance, providers at the stroke center or hospital or emergency room, including neurologists and radiologists. A decision would then be made as to the hospital destination for the ambulance that would maximize care quality, specific imaging and expert availability, and reduce time to evaluation and therapy. Further, preparation of imaging needs, clot buster mixing, other protocol requirements for diagnostics, and preparation of the angiography suite and personnel for rapid intra-arterial clot buster or clot retrieval would be promoted by this plan. This can be done prior to the patient's arrival at the medical facility and emergency department. The embodiments foster a logistical operation that would reduce time and maximize potential appropriate therapy, reduce risk, and improve patient prognosis.

In exemplary embodiments, a system architecture of software and hardware, and network management with an operations center have been employed and optimized to maximize audio video telemedicine as well as physiological data transmission, i.e. ultrasound of brain and neck blood vessels, by persistent connectivity in different environments, including variable bandwidth situations and low signal in rural and urban settings.

Telemedicine can be applied to acute care with emergencies, non-emergent care, and long-term care of neurological, neurosurgical and other medical disorders. The type of monitoring can include real-time, store-and-forward and remote monitoring. "Store-and-forward" is defined as asynchronous transmission of medical information that can be accessed at a later date or for immediate processing. As would be understood by those skilled in the art, store-and-forward corresponds to when the packet source, destination and CRC checksums are validated before the packet is forwarded on the wire. Cut-through refers to data that is not validated as to data integrity prior to forwarding across the wire. Cut-through can be faster than store-and-forward but has an increased risk of corrupt/useless packets and so data packets frequently must be resent due to errors. The stored data can be used for later or simultaneous big data analysis The telemedicine system can include exchanging images, videos and audio information. Real-time telemedicine can include the synchronous transfer of medical information between two or more parties, such as an ambulance, operations center, medical facility, and/or one or more telephysicians. The exchange can include live audio/video teleconferencing or the use of medical devices to assess patients clinically or physiologically. In real-time telemedicine, bidirectional communication is essential and demands the received data matches the data sent and must include persistent connectivity and mitigated latency.

In exemplary embodiments, real-time telemedicine can be applied to acute neurological and other medical disorder situations. Real-time and store-and-forward transmissions will be applied to chronic or outpatient care for the system and methods. Bidirectional real-time audio/video telemedicine can be utilized with central coordination at an operations center between patient location in an ambulance or at an urgent care facility, neurology and radiology experts, and an appropriate receiving hospital and emergency medicine and neurology and radiology professionals and ancillary services at the receiving hospital.

Brain and neck imaging modalities can be used for the rapid evaluation of stroke. At the time of stroke, ministrokes, suspected strokes, or transient ischemic attacks (TIAs), a CT scan of brain can be performed to look for bleeding or brain hemorrhage, stroke presence and size, or other diagnosis. Under normal results, treatment decisions are based on neurological examination. When a hemorrhage is present, the patient follows a different but rapid treatment pathway. Embodiments within this disclosure provide systems and methods to distinguish stroke with hemorrhage from stroke without hemorrhage, using, for example (but not limited to), phased array, carotid and/or transcranial Doppler and photoacoustic spectroscopy.

Typically, a CT scan of the brain is routinely available in most hospitals. Reading of the data may or may not be available or available within the required time frame. Telemedicine systems with CTs can provide information in advance and in the prehospital period. In hospitals, magnetic resonance imaging (MRI) of the brain (intracranial) is more sensitive and specific for stroke and for therapy risk assessment for stroke than CT scan for stroke presence and severity and therapy risk evaluation, but in the majority of hospital and emergency settings, MRI is not physically available or with rapid expert interpretation rapidly, i.e. within 15-20 minutes and is expensive. The telemedicine systems and methods of the exemplary embodiments can be used alone or in combination with CT and/or MRI imaging to provide a sensitive and specific means to determine appropriate rapid therapies for acute stroke and help to delimit risk. The exemplary embodiments provide imaging methods for distinction of stroke with brain hemorrhage from stroke without hemorrhage that would affect the type of treatment, while also saving time.

In exemplary embodiments, 2D and 3D carotid Doppler and transcranial Doppler can be employed in pre-hospital evaluation and can replace vessel imaging in multiple circumstances. The system and methods of the exemplary embodiments can be used to look for blood vessel abnormalities, including stenosis and obstruction of the main brain arteries, including the middle cerebral arteries and basilar artery, and neck arteries, carotids, as a basis for stroke and for specific intravenous clot buster therapy and intra-arterial clot buster or catheter based clot retrieval therapy.

FIG. 1 illustrates a telemedicine system environment 100 according to an exemplary embodiment of the present disclosure.

In an exemplary embodiment, the telemedicine system environment 100 includes an emergency vehicle 102 that is communicatively connected to an operations center 120 via a network 110. The emergency vehicle 102 can include ambulances, emergency helicopters, airplanes, and/or other vehicles as would be understood by one of ordinary skill in the relevant arts. The vehicle may include a motor (e.g., an engine), a windshield, at least four wheels, at least two axles, a body or frame, and a motor power source (e.g., a battery and/or a fuel tank). Vehicle can also include oil rig.

The network 110 can include one or more well-known communication components—such as one or more network switches, one or more network gateways, and/or one or more servers. The network 110 can include one or more devices and/or components configured to exchange data with one or more other devices and/or components via one or more wired and/or wireless communications protocols. In an exemplary embodiment, the network 110 is one or more backhaul networks, such as a cellular backhaul network, Internet service provider network, GNSS backhaul network, the Internet, and/or one or more other networks as would be understood by one of ordinary skill in the relevant arts.

The vehicle 102 can include a telemedicine system configured to communicate with the operations center 120. The telemedicine system can include measurement devices configured to perform high quality, telemedicine neurological examinations. For example, the telemedicine system can be configured to collect measurements for brain and neck vessel function and physiology. The telemedicine system can include a multimedia system, such as one or more cameras, displays and input/output (I/O) devices configured to teleconference with one or more operating centers 120. A telemedicine system according to an exemplary embodiment is described in more detail below with reference to FIG. 2. In an exemplary embodiment, the operations center 120 and the telemedicine system 200 (FIG. 2) can include a teleconference solution to facilitate multimedia (audio/video) communications between the components within the telemedicine system environment 100. In an exemplary embodiment, the teleconference solution can include Polycom™'s RealPresence Platform by Polycom, Inc., other Polycom-based platforms or the like, that assure communication, telemedicine note construction, connectivity, redundancy, quality of service within a broad bandwidth range (including lower bandwidths), platform quality, cellular wireless and/or satellite compatibility; carotid and transcranial Doppler and/or other diagnostic devices and/or their associated software compatibility. In the exemplary embodiment, the telemedicine system can use the aforementioned teleconferencing solutions at the application layer; however, those applications ride on top of the fully redundant physical, network and transport layers, which are designed as a complete system, with no single point of failure and with 5-9 s (99.999%) availability. The telemedicine system can maintain a video resolution high enough to effectively evaluate a patient remotely, and such video resolution is at least 80-128 Kbps of streaming IP. Communication and other telemedicine applications can be used individually or concurrently with different telemedicine platform options. In an exemplary embodiment, the telemedicine system is an integrated information, data transfer, and analysis solution that includes a webcam-equipped, ruggedized laptop with software including, but not limited to, video teleconferencing, EHR/EMR, ultrasound with the ability to scan and render in 3D, carotid and transcranial Doppler images, and/or an enhanced transport layer software that (i) mitigates high-latency of packets across at least one satellite link and at least one cellular wireless link and (ii) provides Quality of Service (QoS) and wide-area network (WAN) optimization across the at least one satellite link and the at least one cellular wireless link. The enhanced transport layer software can be, for example (but not limited to), an enhanced software that is a streaming protocol (e.g., User Diagram Protocol (UDP))-based and allows sending local TCP acknowledgements (ACKs) to a computer or a mobile device on each endpoint of the WAN connection so it appears at each endpoint that there is sub-millisecond latency between the computer or mobile device on each endpoint of the WAN connection. As another example, the enhanced transport layer software can be the L4 software from Circadence or the like. Additionally, interfaces are required for connecting digital tools, such as an otoscope, stethoscope, EEG, EKG, etc. Dual LTE dipole antennas, dual environmentally-hardened routers and/or power supplies with interfaces to connect satellite modem/router, a flat-panel VSAT antenna or BGAN antenna with associated modem/router can also be connected to and including in the telemedicine system. The telemedicine system also includes an operations center and/or software associated with the operations center that can alert medical personnel (including, but not limited to, emergency medical technicians (EMTs), medics, combat medics, physicians (e.g., formal neurological, radiological, surgical or other medical specialty consults), physician's assistants, nurses, medical students, and medical technicians (e.g., radiology technicians; blood technicians; lab technicians)) in the ambulance and at the hospital. The contents of the telemedicine system's clinical evaluation and consultation can be shared from the operations center in real time with the ambulance personnel/medical director and the receiving hospital physicians and stroke center physicians and their other personnel by direct audio-video telemedicine communication and faxing or electronically delivering a consult note to the receiving hospital. The consult notes along with other physiological and clinical data can be added to the hospital medical record or electronic health record and stored securely at the operations center and data warehouse. The latter stored information can be used for later big data analytics.

In operation, the vehicle 102 can communicate with one or more medical facilities (e.g., hospitals) 140, emergency vehicle control or dispatch centers 142, and/or medical physicians 144 (e.g., tele-physicians). The vehicle 102 can communicate with one or more of these entities via the operations center 120 and/or can be configured to communicate directly with one or more of the entities. In an exemplary embodiment, the telemedicine system can be standalone system located at, for example (but not limited to), a facility 104, such as an urgent care center or other medical facility; a government building such as a fire station or a police station; and/or any facility as would be understood by those skilled in the relevant arts. The standalone system can be portable or implemented as a stationary system.

In an exemplary embodiment, the telemedicine system of the vehicle 102 can be configured to communicate with the operations center 120 via network 110 and one or more wireless and/or wired communication networks. For example, the telemedicine system of the vehicle 102 can be wirelessly connected to the network 110 via a wireless access point 108 and/or a global navigation satellite system (GNSS) 106.

The wireless access point 108 can be configured to transmit and receive communications conforming to, for example (but not limited to), one or more cellular communication protocols (e.g., LTE) and/or non-cellular communication protocols (e.g., WiFi). The GNSS 106 can include one or more GNSS transceivers configured to communicate with one or more GNSS base stations via one or more orbiting satellites. The GNSS base stations can be connected to the network 110.

Figure 9A:
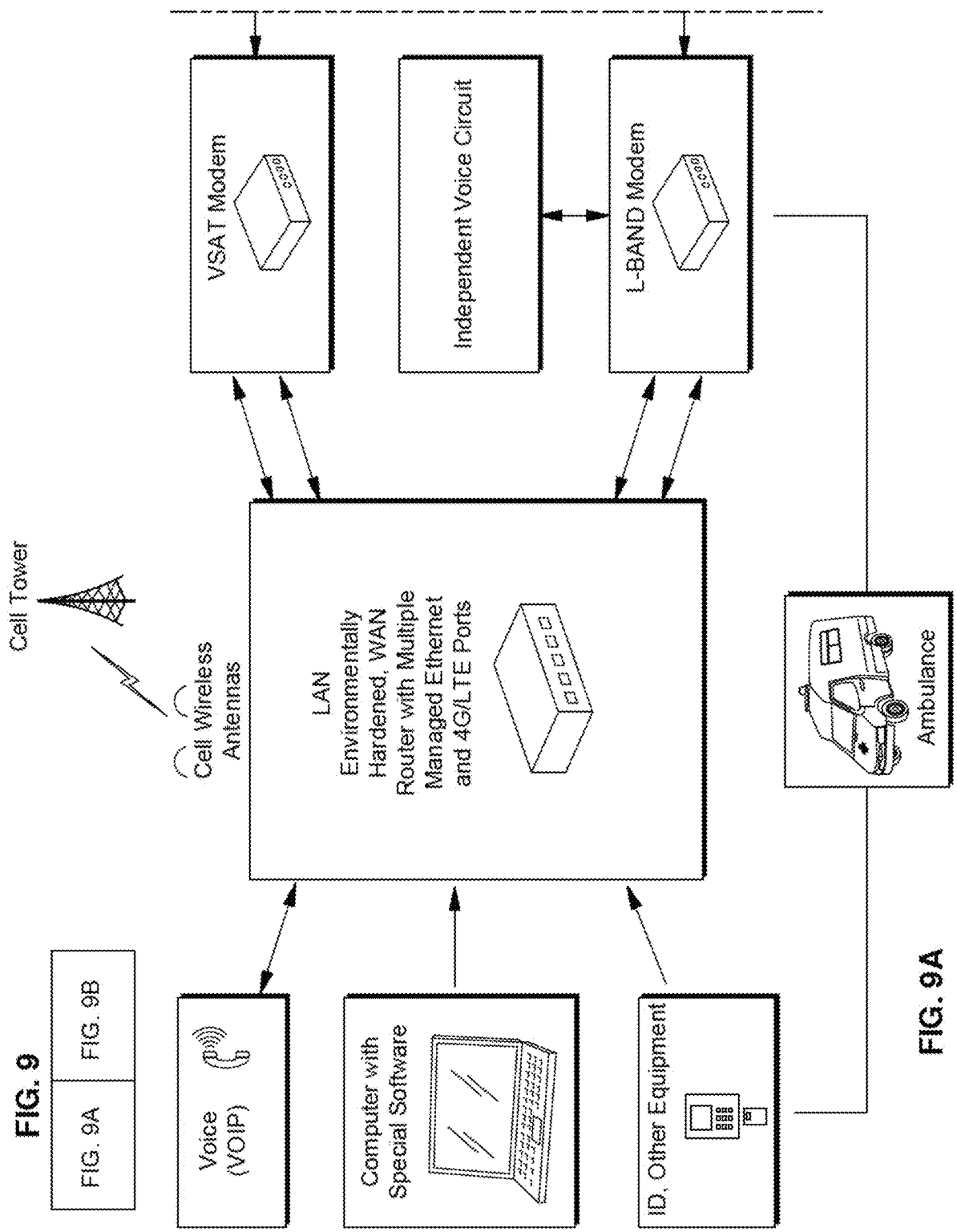
FIGS. 9A and 9B illustrate a network for the telemedicine system according to an exemplary embodiment of the present disclosure.
Figure 9B:
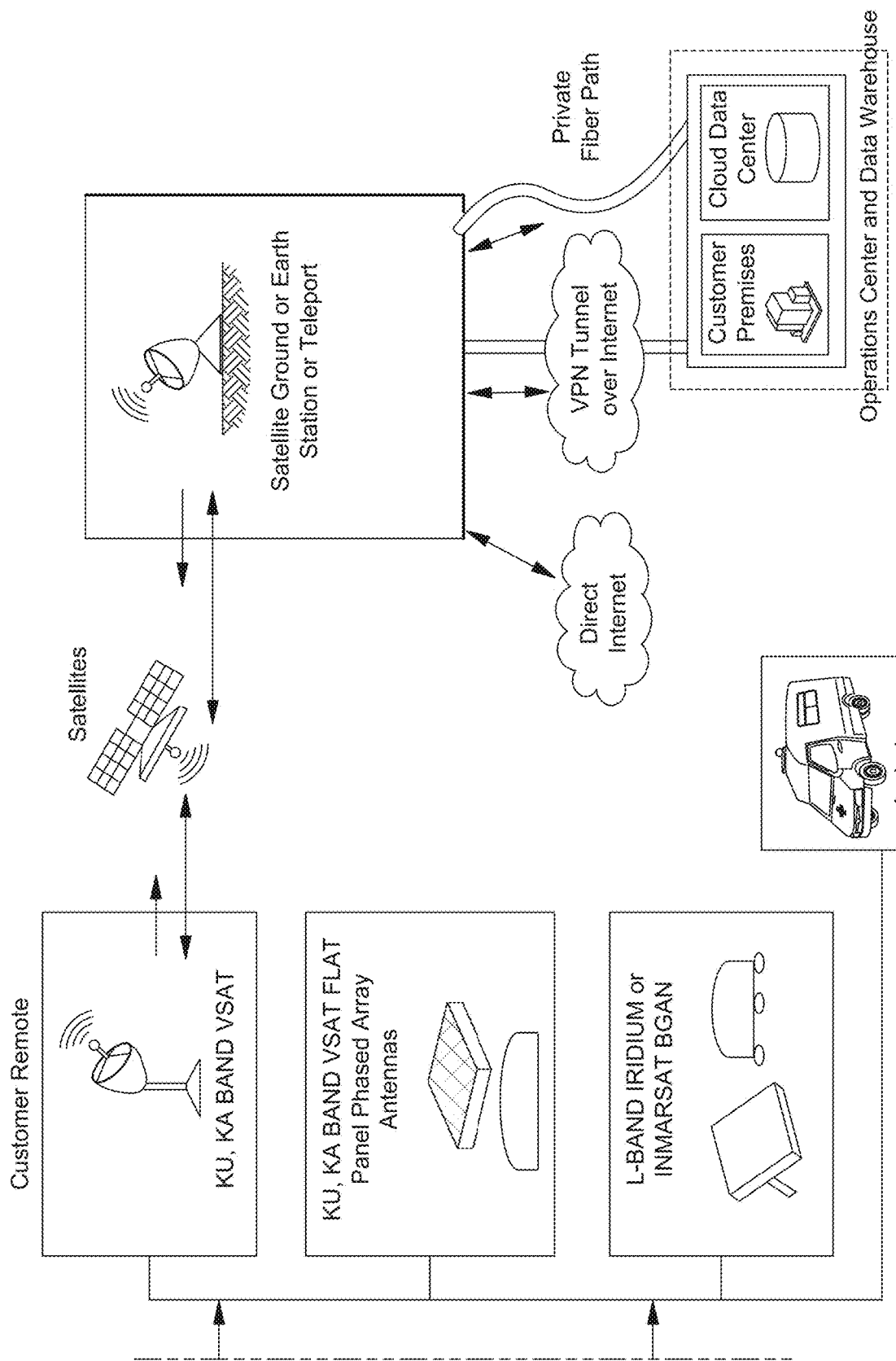

In an exemplary embodiment, the connection between the vehicle 102 and the operations center 120 can be conducted via a telemedicine platform, which may include one or both of broadband global area network (BGAN) and/or very small aperture terminals (VSAT) that utilize satellite technology. As shown in FIGS. 9A and 9B, vehicle 102 may be configured for telemedicine communication alternatively or in addition to any and all of the communication platforms described herein.

In some examples, BGAN and VSAT deployments can be used in rural, maritime, aviation and forward positions. These alternatives allow for mobile antennas tied to land-based hosts and bidirectional flow to and from satellites. In an exemplary embodiment, satellite connectivity involves wireless broadband access from one or more host computers connected to a satellite base station, up to one or more satellites and back to a second base station and computer(s). In an exemplary embodiment, real-time video conferencing maximizes potential latency delays and performance degradation due to the great distances between the two endpoints via the satellite network, as these geostationary satellites are at an altitude of 22,000 miles above the Earth. However, this may be the only available technology in forward military positions, in extreme rural regions with limited or no wireless coverage, in under-developed countries, and as a redundancy solution when there is signal loss or changes in bandwidth or connectivity related to real-time mission critical clinical evaluation using 4G/LTE wireless solutions. In one or more exemplary embodiments, satellite connectivity can be employed in combination with other cellular communications to provide for connectivity and redundancy including but not limited to rural environments, forward military positions, and in low bandwidth situations.

Exemplary features of satellite connectivity via BGAN and VSAT deployments will now be described. The satellite connectivity may occur through a telemedicine system with connectivity. As described below, vehicle 102 may be configured for telemedicine connectivity and includes elements of a telemedicine system.

The present invention's connectivity and Quality-of-Service telemedicine hardware/software solution, with interfaces to existing cellular LTE and satellite networks, allows for real-time, point-of-care evaluation in First Responder vehicles at up to 90 MPH and without limitation due to elevation, with immediate expert neurological and device-related physiological, blood vessel/brain examination. The highly-resilient telemedicine solution overcomes negative effects of transient, low-quality cellular connectivity encountered when traversing multiple cellular towers and multiple service providers at high-speed by masking brief outages to the endpoint software, preventing application re-authentication and application crashes. The same underlying transport technology mitigates the effects of high-latency links, optimizing the WAN connection, resulting in 2× to >10× increases in data transfer rates. Dual-polarity external antennas and hardened routers are deployed complementing the transport layer software, which combined offer a highly available mobile telemedicine solution.

The end-to-end solution is also highly secure, designed to prevent common man-in-the-middle and traffic replay attacks. The system employs dynamic lossless compression whenever possible to reduce the amount of data sent over the WAN connection allowing high-quality video to traverse even sparse cellular coverage areas. It also prioritizes traffic based on pre-defined metrics whereby mission-critical data always takes precedence over the WAN vs. lower priority traffic.

A satellite is a heavy object which goes around another object in space related to the effect of mutual gravitational forces. Artificial, active satellites focused on telecommunication and non-military applications are commercially available and fall into three categories, or zones, depending on their altitude above the earth's surface: Low Earth Orbit (LEO), Medium Earth Orbit (MEO) and Geostationary Orbit (GEO).

These satellites have transponders or communication channels and are controlled by operators through tracking, telemetry and command for earth stations and satellite control centers. Specific satellites and satellite operator can be chosen and contracted with for specific networks. These satellites may be ground to ground, ground cross link ground, and ground to relay platform. Satellite communications are not restricted by geographical location and operate at certain bands and dependent on angle, optimized for speed and mitigated effects of delay. The satellite link involves an uplink from transmitting earth station to satellite, the repeater or satellite, the downlink from satellite to earth station or platform and the receiver or earth station. Frequency modulation or phase variation is used. The link is optimized for path, atmospheric losses, ionosphere losses, antenna system losses, and linking system losses. Some of the sources of noise include: man-made noise, radiation from sun and moon. Rain and vegetation absorption. Communication includes analog signals, speech and video and digital, i.e. telemetry, data transfer. Satellite transponders and earth stations operate at certain bandwidths, which can be optimized. The BR system with satellites is shown in FIGS. 8, 9A, 9B, and 10.

LEO's sit closest to the Earth, up to 2000 kms distance from Earth. The Iridium constellation is the most notable of LEOs, operating at 780 kms above earth. LEO's offer the quickest round trip for a communication signal and so latency is at its lowest. Due to being closer to earth, each LEO satellite's coverage area of an area of Earth is smaller than the other two orbits, so a greater number of satellites are required to cover the same area that a MEO or GEO can. Iridium is the only constellation that offers truly global coverage, including over the Poles. Iridium satellites communicate with each other in space via 10 Mbit microwave links in order to 'pass' a signal transmission between them in order to facilitate the path of that signal to its intended destination (Iridium teleport/remote device). MEO's most commonly sit in the range of 19,000 kms to 27,000 kms distance from Earth. The most common satellites in this orbit are for communications and navigation, the most well-known being the Global Positioning System (GPS). The O3b communications constellation is a very new addition to this orbit, its technology is advanced and offer from 250 Mbps to over 500 Mbps for individual ground terminals. However, the equipment O3b use to provide such a service is large and very expensive and certainly not for a mobile environment.

GEO's are at approximately 36,000 kms directly above the equator, maintaining a geostationary orbit at a fixed location about the earth, moving with the earth rotation at the same rate. Life span of 15-20 years due to the optimum amount of fuel that can be stored and used to maintain a precise fixed position in relation to earth. GEO's are much 'larger' in capacity (both size and the amount of data they can process and transmit) and the predominant purpose of their greater distance from earth is to maximize the extent of their coverage area on the earth's surface (most GEO satellite 'beams' will operate as far toward the poles as approximately 12-15 degrees from the horizontal). Due to the distance from earth, only 3 Geostationary satellites placed equidistant from each other are required to cover the earth's surface (excluding the Poles).

Communications satellites offer up voice-only services, basic compressed data (email, weather reporting, etc.), machine-to-machine (M2M or M-to-M), basic broadband IP and up to very high IP data throughput.

Latency, or the time taken for a signal to travel from one point to another, occurs in all forms of transmission (light, sound, etc.). In satellite communication terms, latency is the time it takes for a signal to travel to the satellite and back down to earth. For geostationary satellites, that latency is approximately 250-300 milliseconds. However, as IP data requires a pinged response each time an IP packet is sent to tell the originator that the packet has been received, latency is measured as the whole round-trip, so in the case of geostationary satellites, that is approximately 550-600 milliseconds.

The lower the look angle from the earth station to the satellite, the more sensitive the signal is to receiver noise due to atmospheric refraction, earth's thermal emission, line-of-sight obstructions, signal reflections with the ground or nearby structures, and weather (cloud cover, snow, fog, rain—the effect of adverse weather on a satellite signal is called rain-fade, which can affect the signal loss regardless of look angle to the satellite). All these contributory factors also have a differing degree of impact on the various Radio Frequency (RF) bands, with L-band possessing the greatest ability to penetrate adverse atmospheric/weather conditions and Ka-band the least.

Geostationary satellites are also subject to solar or sun outages (when the sun is directly behind the line-of-site between the satellite and the earth station, solar radiation is at its strongest point and interferes with the satellite signal by distorting it. These incidents occur twice a year, affecting any specific location for less than 12 minutes a day for a few consecutive days.

The satellite terminal may differ for stationary and mobile applications. A BGAN terminal may be used for streaming IP services at up to 256 Kbps of bandwidth in a vehicle moving at high-speed. Otherwise, a software-tuned, flat panel array may be used for streaming IP services at 10 s of megabits per second, while a vehicle is moving at high-speed or while at rest.

In a mobile environment, the antenna system needs to be able to stay 'locked on' to the satellite(s) regardless of direction, speed and angle. Therefore, antennas for mobile operating environments are 'stabilized' and able to 'track' a satellite when the moving vehicle turns or speeds up, travels at speed or slows down. There are also often weight and size restrictions in a mobile environment, meaning mobile satellite equipment needs to be small in comparison to satellite equipment on a fixed site, which results in a restriction in capacity to process, send and receive data. Video transmissions systems (ntsc, pal and secam), and encoding systems would follow Mpeg-2 and h.264/Mpeg-4 AVC standards.

Mobile antenna systems can either be the omni-directional, domed antenna common for lower bandwidth (up to 256 kbps), L-band service, or flat-panel, software-steered VSAT antennas capable of 10 s of megabits per second. Firewalls can operate at both the remote/mobile site and at the hub/teleport site or anywhere within that private network.

In an exemplary embodiment, the telemedicine satellite application is aimed at emergency responders (such as ambulances, fire trucks) for mobility hardware and corresponding service platforms.

Satellite communications provide ubiquitous coverage and service availability with high reliability for communication. Performance is insensitive to terrain (except for steep mountainous regions using GEO or MEO satellites; instead, LEO satellites must be used) or distance and transmission costs are not distance dependent. Remote satellite equipment is relatively quick and easy to install and satellite network topology is flexible to easily add, move or delete remote sites.

The end user uses a modem that interfaces between the user's computer and an outside antenna with a transceiver (Block Up Converter or BUC and Low Noise Block Downconverter or LNB). The BUC is a power unit that amplifies the signal and increases the frequency in order to send it up to the satellite. The LNB converts the received signal (from the satellite) back down to an amplification and frequency manageable by the ground based system (e.g., 12 GHz satellite transmission to 1 GHz so that less is lost). The transceiver receives or sends a signal to a satellite transponder in space. The satellite sends and receives signals from an earth station, or teleport, that acts as a hub for the system. Each end user is interconnected with the hub station via the satellite in a star topology. For one end user to communicate with another, each transmission has to first go to the hub station which retransmits it via the satellite to the other end user's satellite terminal. Such satellite terminals handle data, voice, and video signals.

The antennas and satellite terminals that deliver different satellite services include small portable BGAN terminals, VSAT terminals (very small aperture terminals), which include large footprint antennas and newer flat panel arrays (geared towards the mobile application environment such as Aeronautical, maritime and land vehicles).

Small portable BGAN terminals can be highly portable terminals which provide connection to a computer and optional handset, globally (excluding the poles) via the Inmarsat L-band frequency network. There are a number of models available, and specifically for mobility these are Cobham Explorer 325 and 727, Add Value Safari, Thuraya Voyager and Hughes 9450. The Inmarsat BGAN network and these terminals are limited significantly with the amount of data that may be accessed and the speed at which that data can be transferred.

Certain mobility BGAN terminals provide the greatest throughput (up to 492 kbps standard IP and up to 256 kbps dedicated streaming on the move/384 kbps on-the-pause). Standard IP is based on best effort and the number of terminals being used in a given region. Inmarsat BGAN represents a small form factor terminal, limited broadband speeds on a contended network (with even more limited scope for applying dedicated bandwidth).

It should be noted here that the forthcoming Iridium NEXT/Certus satellite network and platform (estimated full network capacity in 2019/2020) will offer higher data speeds (up to 1.2 Mbps MIR, with realistic contended throughput being around 350-400 kbps) on a smaller terminal than BGAN.

In an exemplary embodiment, the cellular wireless components of the telemedicine system can be combined with a satellite based network. The cellular wireless is redundant and can automatically switch between cell carriers and be interfaced with a hard-wired Ethernet network, providing connectivity to the satellite terminal on the WAN-side and to the laptop on the LAN-side of the telemedicine solution.

In an exemplary embodiment, a satellite network can be applied to the telemedicine system. This network can interface and combine with the cellular wireless network to provide expanded and potentially full connectivity and quality of service. Redundancy is promoted by both cellular wireless and satellite networks that can work in environments with poor connectivity, including but not limited to highly utilized urban networks or mountainous or other high altitude regions or remote regions, that are not serviced or capable of cellular wireless. Both satellite and cellular wireless networks that are interfaced to the telemedicine system can also interface with hard wired Ethernet networks.

In an exemplary embodiment, the system has been developed to work with telemedicine programs that can operate with high quality audio and video at bandwidths as low as 128 kbps with limited latency and full connectivity in a vehicle moving at high-speed.

VSAT (Very Small Aperture Terminal) will now be described. Different types of services may be delivered using VSAT (either dedicated or shared services). For a mobility application, Ku-band and Ka-band frequencies are preferred and will offer differing levels of availability depending on the location the antenna is being used, the size of the antenna and its associated RF equipment (primarily BUC power), as well as environmental conditions (inclement weather affecting the Ka frequency greater than Ku). Standard VSAT antennas are large (1.0 m to 1.8 m) fixed or auto-deploy antennas, large relative to Inmarsat BGAN terminals. However, this does not work for a mobile environment. For mobile communications, flat panel phased array antennas are required. There are a number of manufacturers of such antennas including RaySat (Gilat), Phasor, ThinKom, and most recently, Kymeta. Multiple Mbps are attainable. However, two drawbacks with VSAT antennas are: First, the technology is considerably expensive. Second, more satellite bandwidth is required for the same gain/data speeds. Further, the type and size of any VSAT antenna and BUC power will depend on availability required, location of the requirement and data speeds required.

Current BGAN capabilities (up to 256 kbps streaming IP in moving vehicle) allow for telemedicine applications to be deployed in most environments. However, BGAN terminals connect to GEO satellites, which quickly lose signal when the terrain in which they are deployed becomes mountainous. In such environments, a flat-panel antenna (e.g., Kymeta's mTenna) connecting to LEO satellites is required. Bandwidths of 10 s of megabits per second can be maintained, even while travelling at high-speed.

As with VSAT antennas, there are different types of services that may be delivered using different types of satellite 'platforms' and associated modems (modems are not generic/ubiquitous and only work with specific platforms). Three of the most widely used VSAT satellite platforms globally are iDirect, Hughes and Gilat.

When trying to transmit multi-Mbps data to/from a satellite in bands>10 GHz (Ku- and Ka-band), the path loss through the atmosphere and RF parameters mean that as much gain as possible is wanted. This is why the most economical solutions for high capacity two-way satellite through geostationary transponder capacity involve 1.8 to 3.0 meters-size dish antennas. VSAT needs at least 10 times more gain than BGAN, but attainable data speeds are far higher compared with L-band BGAN.

In an exemplary embodiment, the ambulance roof and its size has been used as a basis for easily affixable satellite terminal/antennas (BGAN), with automatic pointing features, for mobile applications for telemedicine and other data transfer. In the exemplary embodiment, VSAT with non-automatic pointing and automatic pointing can be deployed as part of the system in stationary environments, including during setup ambulance before transport. In the exemplary embodiment, interface with established global satellite platforms with ease of interfacing, quality of communication, and also maximal attainable Mbps.

Figure 8:
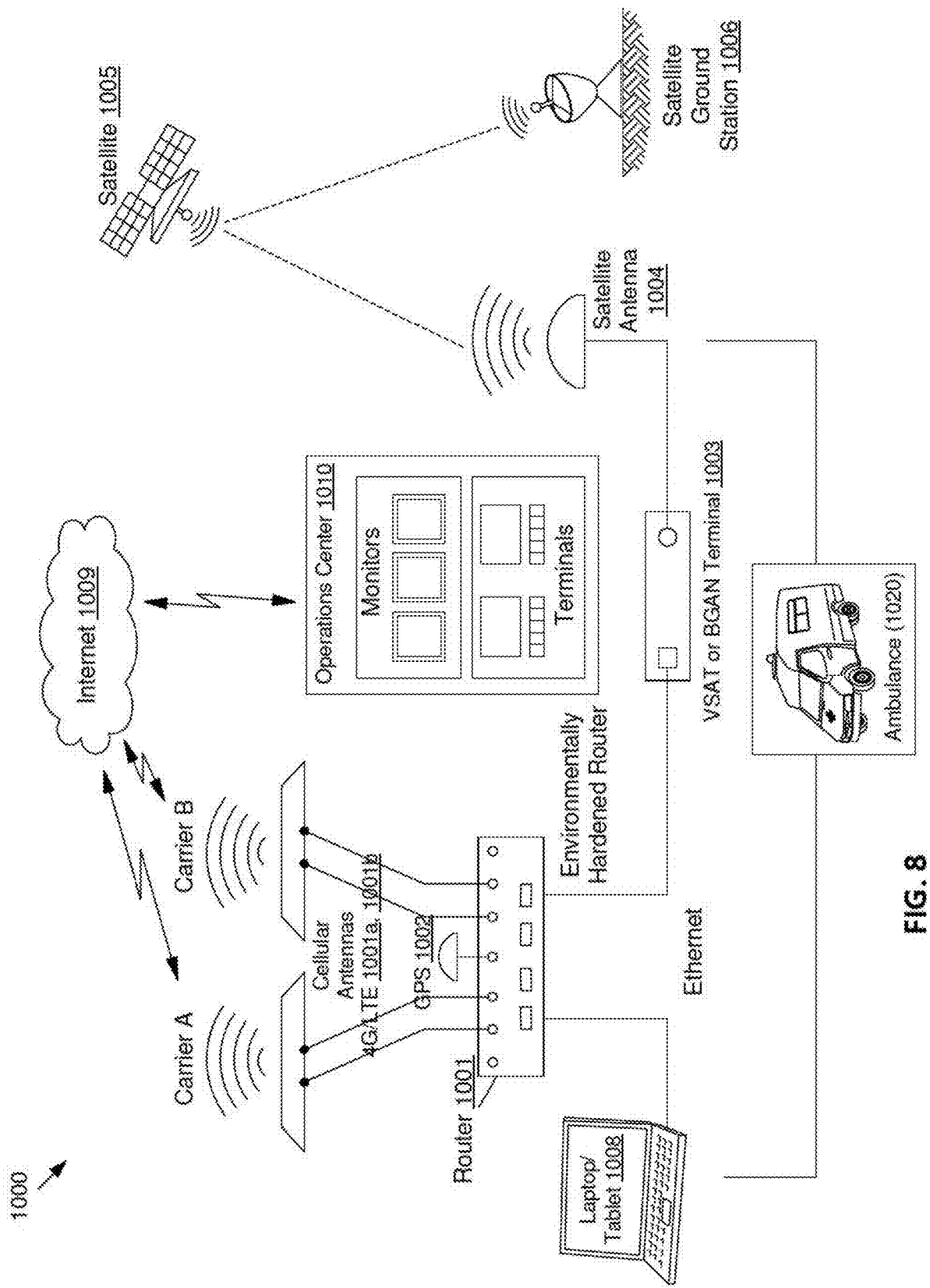
FIG. 8 illustrates a network for the telemedicine system according to an exemplary embodiment of the present disclosure.

Referring to FIG. 8, a network system 1000 enabling the full telemedicine solution include, at the hardware layer, of redundant, hardened, LAN/WAN routers 1001 with multiple Ethernet and cellular 4G/LTE ports. Connecting the dual routers are dual di-pole LTE antennas 1001a, 1000b. Synchronizing the cellular signals are redundant GPS antennas 1002. Additionally, a VSAT or BGAN antenna 1004 and router 1003 complete the hardware connectivity. The satellite router achieves connectivity with the system by-way-of an available Ethernet port on the LAN/WAN routers 1001. Specialized real-time software running on the LAN/WAN routers 1001 constantly monitor the signal strength of each of the WAN connections to determine the most reliable signal. Also verified by the system 1000 is the response time, measured in network-layer latency, of each WAN link to determine the connection best suited to be chosen as the primary link. A combination of the signal strength at the physical layer and the lowest response time at the network layer determines the WAN connection best suited to transport the telemedicine applications. SLAs may also be configured on the system to choose a connection with the lowest application response time. Embedded algorithms also monitor connections for potential flapping, whereby connections continue to get chosen vs. other connections pathologically based on transient conditions preferring one connection over others. Flapping quickly leads to no data being transmitted/received. QoS, to ensure specific applications receive preferential treatment over other lower-priority applications, is governed in both the routers and at the transport layer.

Referring to FIGS. 9A and 9B, a telemedicine cell wireless and satellite system is shown. Voice over IP (VOIP), a computer laptop or tablet with telemedicine, other specialized software, and neuroimaging software, and other equipment connect in the ambulance or other moving vehicle or other site, e.g., clinic or hospital, to a LAN router with multiple managed Ethernet ports. The router routes data traffic to specific areas in the LAN and also aggregates multiple connections, including 3G, 4G, 5G plus WiFi, plus LTE and satellite. The router can automatically switch between cellular and satellite and other inputs by specific programming and firmware. Data can be aggregated or split. Within and outside the ambulance or moving vehicle, the LAN router is connected through its ports to specialized dual antennas, see FIG. 5, which can communicate directly with and switch between cell towers. These in turn provide web connectivity and can connect to the operations center. The LAN router can also have one or more connections through its Ethernet ports to a VSAT modem, within the ambulance, which can then connect directly to a VSAT antenna or satellite terminal. Any satellite terminal discussed herein may include one or more antennas.

Referring to FIGS. 9A and 9B, the VSAT terminal may deliver power to the antenna (BUC and LNB) and is connected with a RF cable. Similarly, the LAN router can have, simultaneously, one or more connections to an L-Band satellite modem within or outside the ambulance. This modem can be independent, connected by Ethernet or RF cable or incorporated into a Satellite antenna or terminal. An independent voice circuit can be connected to the L-band modem for additional audio input. The satellite modems are connected to antenna or satellite terminals which then connect with the satellites.

Referring to FIGS. 9A and 9B, three customer remote terminals can be involved. First, the Ku or Ka VSAT, manually or automatically, acquires a signal that can be used and interfaces with the VSAT modem. The Ku and Ka VSAT terminals are 0.6 meters to 3.6 meters. Second, the Ku or Ka VSAT flat panel phased array terminal/terminal with size between 3-4 to 30 cm. This is interfaced to VSAT modems. Third, L-Band Iridium or Inmarsat BGAN portable manual or auto acquire that are mobile for moving vehicles can be interfaced with the L-Band modems. Each of the three terminals can provide one-way simplex or two way duplex traffic and data flow.

The satellites used in the exemplary embodiments herein include, but not limited to, GEOs e.g., Inmarsat, SES, Intelsat, JSAT; MEOs, e.g., O3b, GPS; and LEOs, e.g., Iridium, Orbcomm. These satellites may have spot beams, steerable beams, regional fixed beams, interplaying moving beams, and global fixed beams. The satellites can provide one-way or two-way data flow to a satellite ground station or teleport. All traffic is processed at the stations in the hub and routed to specific destinations, determined by IP packets and headers via multiple paths. These paths can include direct Internet, a VPN tunnel over the Internet, and a private fiber path to the operations center and mobile computer based systems.

Figure 4:
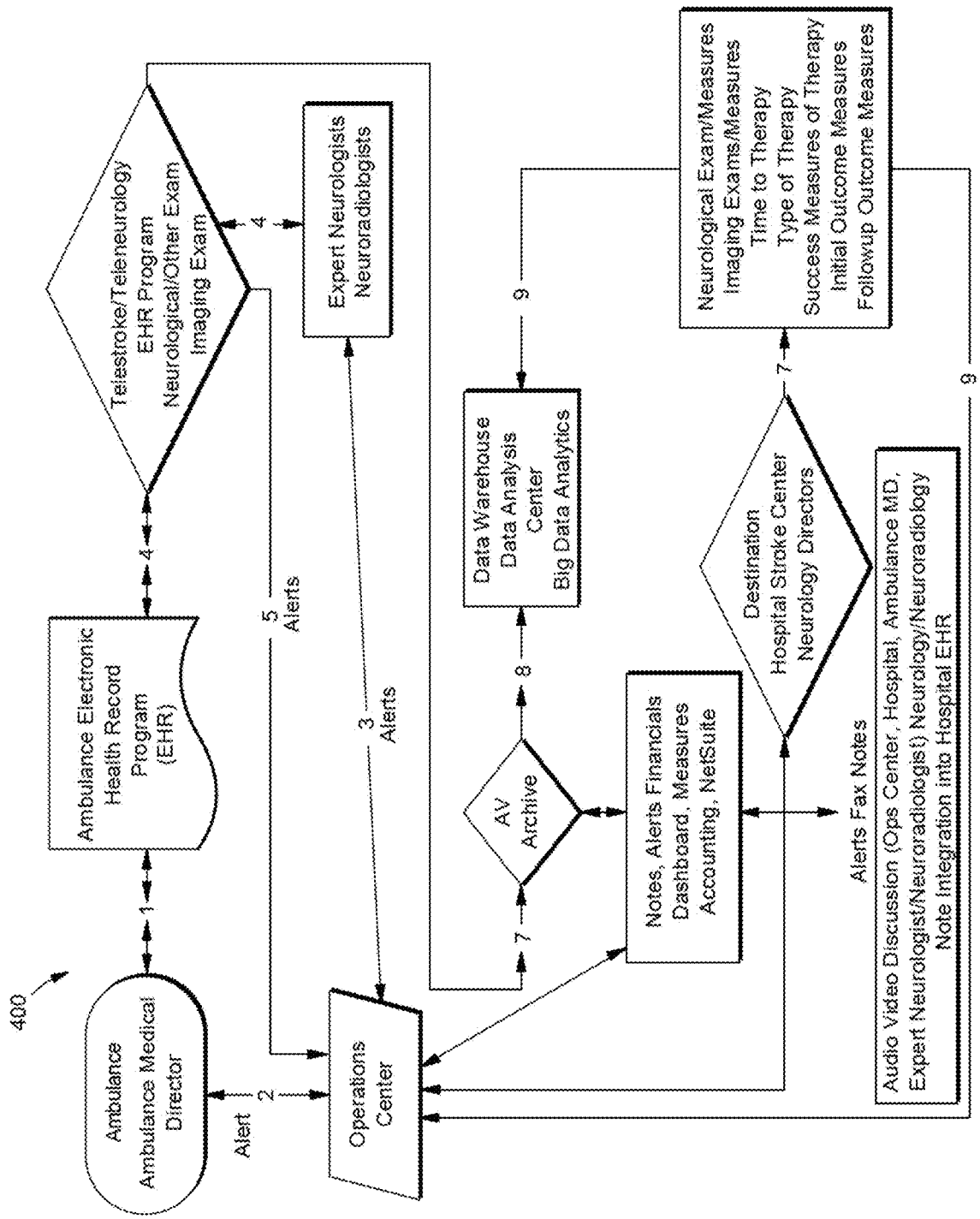
FIG. 4 illustrates a telemedicine system according to an exemplary embodiment of the present disclosure.
Figure 10:
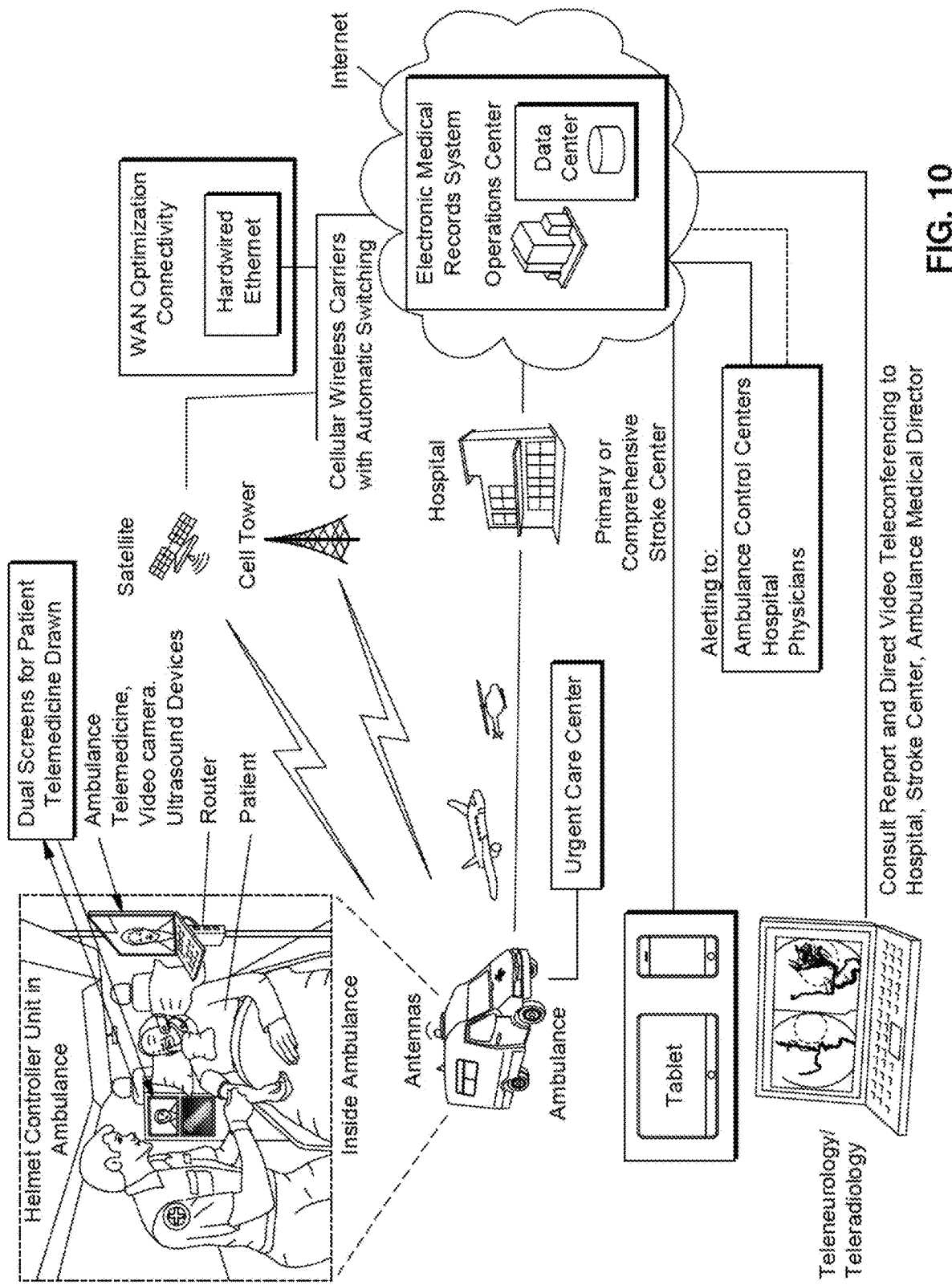
FIG. 10 illustrates communication paths for an emergency response according to an exemplary embodiment of the present disclosure.

Referring to FIG. 10, the patient is evaluated within the ambulance or other moving vehicle or urgent care center or just outside the stationary vehicle with telemedicine involving a laptop computer with specialized telemedicine, connectivity, and ultrasound software. The telemedicine system involves specialized camera. The ultrasound examination involves a special helmet and images are generated in the field and at the operations center. The telemedicine, DICOM, and other data are transmitted via routers and specialized cellular wireless antennas (according to some or all of the cellular communication technologies discussed herein) as well as by specialized satellite terminals/antennas (according to some or all of the satellite communication technologies discussed herein), that work together to provide connectivity and quality of service. The data is transmitted to through satellite and cellular wireless through the cloud to the operations center, that can view in real time all imaging and neurological examinations. At the point of care, the expert neurologists and radiologists can perform their examination of the patient 24/7 by their computer, smart phone, or tablet. A consultation report is written through the operations center. Communication between the ambulance, ambulance medical director, potential destination hospital, stroke and hospital physicians that may receive the patient. Alerting is shown in FIG. 4.

In an exemplary embodiment, as shown in FIG. 1, the operations center 120 is configured as a nexus for communication with multiple remotely located telemedicine systems (e.g., vehicle 102). The operations center 120 may be implemented as a Virtual Desktop Infrastructure (VDI) in the cloud and can include a database 122, server application 124, alerting system 126, Digital Imaging and Communications in Medicine (DICOM) system 128, controller 130, and transceiver 132. A VDI client application may be used on workstations, desktops, tablets, smartphones and other mobile devices that run on Microsoft Windows, Linux, MacOS, Android, iOS, or other desktop or mobile operating systems, which would then connect to the cloud-based, virtual servers. Transceiver 132 may represent any modem and antenna package configured for cellular or satellite communication. The operations center 120 can include a redundant power system to maintain operational power by switching from a primary power source to a secondary power source in the event the primary power source becomes unavailable.

The controller 130 is configured to control the overall operation of the operations center 120, including controlling the operation of one or more of the components of the operations center 120. The controller 130 can include processor circuitry configured to perform the operations of the controller 130. The controller 130 can include memory to store data and/or instructions.

The transceiver 132 is configured to transmit and/or receive wireless and/or wired communications via one or more wireless and/or wired technologies. The transceiver 132 can include processor circuitry that is configured to transmit and/or receive wireless and/or wired communications. The transceiver 132 can be configured to communicate with one or more medical facilities 140, emergency vehicle control or dispatch centers 142, and/or medical physicians 144, as well as with one or more emergency vehicles 102 and/or facilities 104 via the network 110 (which may include satellite communication as discussed above) and the access point 108 and/or GNSS 106.

Those skilled in the relevant art(s) will recognize that the transceiver 132 can also include (but is not limited to) a digital signal processor (DSP), modulator and/or demodulator, a digital-to-analog converter (DAC) and/or an analog-to-digital converter (ADC), an encoder/decoder (e.g., encoders/decoders having convolution, tail-biting convolution, turbo, Viterbi, and/or Low Density Parity Check (LDPC) encoder/decoder functionality), a frequency converter (including mixers, local oscillators, and filters), Fast-Fourier Transform (FFT), precoder, and/or constellation mapper/demapper that can be utilized in transmitting and/or receiving of wireless communications.

The database 122 can be configured to store data, such as patient medical records, including medical images, information regarding one or more medical facilities 140, emergency vehicle control or dispatch centers 142, physicians 144, and/or vehicles 102, and/or other data as would be understood by those skilled in the relevant arts. The database 122 can include processor circuitry configured to perform the operations of the database 122.

The server application 124 can include one or more applications and/or operating systems of the operations center 120. The applications can include one or more application that run to facilitate the functions of the operations center 120. The server application 124 can also host one or more applications that can be provided to remote users, such as the vehicle 102, physicians, 144, dispatch centers 142, medical facilities 140. The server application 124 can include memory that stores the application(s) and/or operating system(s). The server application 124 can also include processor circuitry that can be configured to execute the application(s) and/or operating system(s).

The alerting system 126 is configured to generate and transmit one or more alerts to one or more components within the telemedicine system environment 100. For example, the alerting system 126 can generate an alert in response to a vehicle 102 accepting a patient and/or the vehicle 102 completing a diagnostic test on the patient. The alerting system 126 can generate an alert that identifies the anticipated arrival time of the vehicle 102 to a hospital. In an exemplary embodiment, the alerting system 126 can include processor circuitry configured to perform the operations of the alerting system 126.

The Digital Imaging and Communications in Medicine (DICOM) system 128 is configured to handle, store, print, and/or otherwise process medical images. The DICOM system 128 can specific file formats and/or network communications protocol to comply with the DICOM standard (i.e., NEMA standard PS3, ISO standard 12052:200). The DICOM system 128 can include processor circuitry configured to perform the operations of the DICOM system 128.

In operation, the operations center 120 can be configured to process data through a central system of servers (e.g., server application 124) running an application that provides voice and video, textual data, imaging data, telemetry and tele-operation command communications. The data is routed to an available operations center specialist that is trained to operate the tele-operations and has radiology expertise to acquire usable image and Doppler data.

The operations center 120 may include of pool of radiology tele-operations specialists available to handle data from multiple patients simultaneously. All data (e.g., time, date, patient ID, ambulance, location, images, radiologist or neurologist IDs, emergency room attending physician IDs, operations specialist IDs) surrounding a telemedicine system (e.g., vehicle 102) is collected in a database (e.g., database 122). The database provides internal records for traceability as well as the data to be accessed as part of big data analytics. The operations center specialist will establish communications connections with a qualified diagnostician (e.g., neurologist or radiologist) who will perform the actual assessment of the patient and will provide the consultation to the attending physician. Once the tele-operation specialist has acquired usable images, the images will be uploaded to a medical image server where they will be dispatched to the diagnostician and the attending physician, at which time the images also become part of the patient's electronic medical records.

Diagnosticians (radiologists, neurologists) may be at an operations center facility or remote. An additional remote application can also allow for remote tele-operators. In this way, an external pool of additional diagnosticians and tele-operators may be on call as load demands. In addition to the command and telemetry interface for the telemedicine systems, the remote tele-operator will also have full communications with all diagnosticians, physicians, and ambulance personnel involved with the patient that is assigned to them by the operations center 120.

In exemplary embodiments, the clinical examinations and/or the measurements are collected while the patient is in transport in the vehicle 102, including the electronic health record of the patient with the examination results (e.g., in text format and by audio/video communication) and the measurements are sent to an operations center 120 and/or more neurological and/or radiological experts at one or more remote locations, using advanced health information technology techniques. The operations center 120 and/or neurological and radiological teams can analyze the measurements and/or one or more patent images to determine whether a stroke or other injury has or is occurring, and can provide instructions to the transport team of the vehicle 102. The operations center 120 can also communicate with one or more emergency vehicle control or dispatch centers 142 and/or medical facilities 140 to determine the appropriate facility to route the emergency vehicle to.

In an exemplary embodiment, a textual electronic health record with examination information and interpretation of other physiological measurements are provided to the ambulance personnel of the vehicle 102, the appropriate hospital to which the patient will be transported, and stroke and other personnel at that facility. This allows for the patient can be transported to the appropriate facility and for preparations and decisions to be made prior to the transport's arrival.

Upon arrival at the appropriate facility (e.g., hospital or emergency room), warranted and appropriate medical (e.g., stroke) diagnostics and treatments can begin immediately, thus saving valuable time. Therapy for the patients can be selected and increase the positive outcomes, including stroke reversal and reduced stroke severity, as well as reducing mortality. In assessing stroke, identifying abnormalities or reduced blood flow in neck or brain blood vessels are important because of the associated urgency with addressing these conditions.

Figure 2:
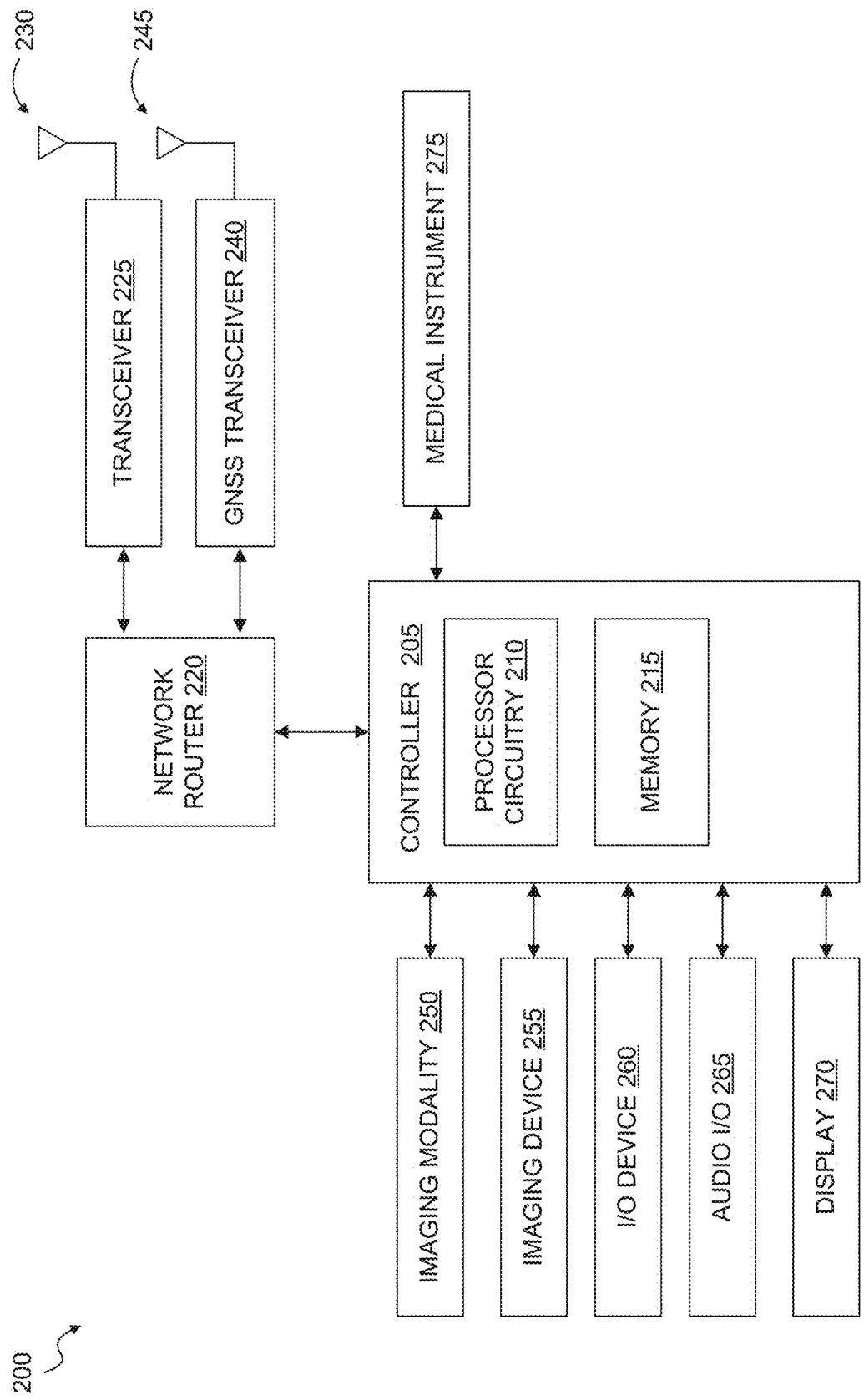
FIG. 2 illustrates a telemedicine system according to an exemplary embodiment of the present disclosure.

FIG. 2 illustrates a telemedicine system 200 according to an exemplary aspect of the present disclosure. The telemedicine system 200 can be included in one or more vehicles 102. In an exemplary embodiment, the telemedicine system 200 includes a controller 205 connected to a network router 220 supporting one or more communication transceivers, such as transceiver 225 and/or GNSS transceiver 240. The transceiver 225 can be configured to (wirelessly and/or via a wired connection) transmit and/or receive communications conforming to one or more cellular (e.g., LTE) and/or non-cellular (e.g., WiFi, satellite) protocols via antenna 230. The transceiver 225 can be configured to transmit and/or receive GNSS communications via antenna 245. Telemedicine system 200 can include a redundant power system to maintain operational power by switching from a primary power source to a secondary power source in the event the primary power source becomes unavailable. As discussed above, telemedicine system 200 can include any aspect of the telemedicine communication platform. Antenna 230 may be configured for communication over any of the above-described satellite systems.

The telemedicine system 200 can include one or more imaging modalities 250, one or more imaging device 225, one or more input/output (I/O) devices 260, one or more audio I/O devices 265, one or more displays 270, and one or more medical instruments 275. These components can be connected to the controller 205.

The controller 205 can include processor circuitry 210 and memory 215. The processor circuitry 210 can be configured to control the overall operation of the telemedicine system 200, such as the operation of one or more components of the telemedicine system 200. The processor circuitry 210 can be configured to carry out instructions to perform arithmetical, logical, and/or input/output (I/O) operations of the telemedicine system 200 and/or one or more components of the telemedicine system 200.

In an exemplary embodiment, the processor circuitry 210 can be configured to control the operation of the transceiver 225 and/or the GNSS transceiver 240—including, for example (but not limited to), transmitting and/or receiving of wireless communications via the transceiver 225 and/or 240, and/or perform one or more baseband processing functions (e.g., media access control (MAC), encoding/decoding, modulation/demodulation, data symbol mapping, error correction, etc.).

The processor circuitry 210 can be configured to control the: running of one or more applications and/or operating systems; power management (e.g., battery control and monitoring); display settings and driving of the display 270; image processing of one or more images and/or videos to be output by the display 270 and/or one or more images and/or videos captured by the camera 225, audio processing of audio captured/inputted via one or more audio I/O devices 265 (e.g., a microphone) and/or of audio outputted by one or more audio I/O devices 265 (e.g., speaker); image processing of one or more images and/or videos captured by one or more of the imaging modalities 250; processing of medical measurement data generated by one or more medical instruments 275; and/or routing of communications via the network router 220.

In an exemplary aspect, the controller 205 can include one or more elements of a protocol stack such as, a physical (PHY) layer, media access control (MAC), radio link control (RLC), packet data convergence protocol (PDCP), and/or radio resource control (RRC) elements.

The memory 215 that stores data and/or instructions, where when the instructions are executed by the processor circuitry 210, controls the processor circuitry 215 to perform the functions described herein. The memory 215 can be any well-known volatile and/or non-volatile memory, and can be non-removable, removable, or a combination of both. The memory 215 can store one or more operating systems of the telemedicine system 200 and one or more applications operable to run on the operating system(s). The memory 215 can also store one or more medical images associated with the imaging modality 250, one or more medical records of one or more corresponding patients.

The imaging device 255 is configured to capture image and/or video data and provide the image/video data to the controller 205. The imaging device 255 can be, for example (but not limited to), a camera and/or a video recorder. The imaging device 225 can be configured to process image and/or video data captured by the imaging device 225 and provide the processed data to the controller 205, where the controller 205 may perform additional processing in some embodiments. In an exemplary embodiment, one or more of the imaging devices 255 are included in the vehicle 102 to provide images and/or video of the patient and/or the emergency personal in a multimedia telemedicine solution. The imaging devices 225 can be mounted in the vehicle 102.

The I/O device 260 is configured to interface with the controller 205 as an input and/or output device of the telemedicine system 200. The I/O device 260 can include, for example (but not limited to), a keyboard, mouse, trackpad, smart pen, printer, scanner, and/or other input and/or output devices as would be understood by those skilled in the relevant arts.

The audio I/O device is configured to interface with the controller 205 as an audio input device and/or audio output device of the telemedicine system 200. The audio I/O device 260 can include, for example (but not limited to), a speaker configured to output audio, a microphone configured to capture audio, and/or one or more other audio input and/or output devices as would be understood by one of ordinary skill in the relevant arts.

The display 270 is configured to display images and/or video data. The display 270 can be, for example (but not limited to), a computer monitor or other display device, projector, LCD display, LED display, OLED display, and/or one or more other display devices as would be understood by one of ordinary skill in the relevant arts.

The medical instrument 275 is configured to measure or otherwise capture medical information from a patient and/or output medical information associated with a patient to, for example (but not limited to), one or more medical personnel. The medical instrument 275 can be, for example (but not limited to) an otoscope, a stethoscope, phonendoscope, sphygmomanometer, pulse monitor, thermometer, electrocardiograph (EKG, ECG), ultrasound device, and/or one or more other medical instruments as would be understood by one of ordinary skill in the relevant arts.

The telemedicine system 200 and one or more of the components of the telemedicine system environment 100 can be configured to utilize one or more network optimization applications. In an exemplary embodiment, the controller 205 of the telemedicine system 200 can include a network optimization application configured to mask transient network outages and/or reduced bandwidth from applications allowing the applications to pause until the network connections are restored. By masking transient network outages/reduced bandwidth, the application running and supporting the telemedicine system 200 are unaware of connectivity issues (or the severity of an issue is reduced at the application level) to reduce and/or prevent the running applications from terminating or crashing in response to a network outage. In this example, the network optimization application provides link resiliency to the communication links of the telemedicine system environment 100. Controller 205 may be configured to switch communication networks to mask transient network outages, such as switching between cellular communication and satellite communication. Controller 205 may further switch between specific kinds of satellite communication (e.g., between BGAN and VSAT and/or 4G cellular and 3G cellular) based on a detected level or network strength (e.g., signal strength optionally combined with data throughput).

The network optimization application can also be configured to provide a Transport Morphing Protocol (TMP). The TMP is an acknowledgement-based user datagram protocol (UDP) with built-in QoS (Quality of Service). The TMP is configured to allow endpoints to automatically adjust data send rate to reduce packet loss and minimize resent packets. The TMP allows data transfers and application performance to be maintained even on degraded communication links and prevents application time-outs during excessive packet loss situations and/or high latency situations.

In an exemplary embodiment, the network optimization application can support one or more encryption technologies, such as Secure Sockets Layer (SSL) encryption. In an exemplary embodiment, the encryption technologies can be used without requiring the installation of client certificates. Using these encryption technologies, the telemedicine system 200 can communicate with the components of the telemedicine system environment 100 while maintaining Health Insurance Portability and Accountability Act of 1996 (HIPAA) compliance.

In an exemplary embodiment, the network optimization application is Circadence's MVO 1200 Optimization Suite produced by Circadence Corporation, but is not limited hereto.

In an exemplary embodiment, the network router 220 is configured to forward data packets between two or more networks, using, for example (but not limited to), one or more routing tables and/or routing policies. The network router 220 can be configured to interface with one or more cellular networks (e.g., LTE, EVDO, HSPA+), one or more non-cellular networks (e.g., WiFi 802.11), and/or one or more GNSS networks. In an exemplary embodiment, the network router 220 includes processor circuitry configured to perform the operations of the network router 220.

For example, the network router 220 can be configured to route data packets conforming to one or more cellular networks, including, for example (but not limited to) Long-Term Evolution (LTE), Evolved High-Speed Packet Access (HSPA+), Wideband Code Division Multiple Access (W-CDMA), CDMA2000, Time Division-Synchronous Code Division Multiple Access (TD-SCDMA), Global System for Mobile Communications (GSM), General Packet Radio Service (GPRS), Enhanced Data Rates for GSM Evolution (EDGE), and Worldwide Interoperability for Microwave Access (WiMAX) (Institute of Electrical and Electronics Engineers (IEEE) 802.16) to provide some examples. The network router 220 can be configured to route data packets conforming to one or more non-cellular networks, including, for example (but not limited to) one or more IEEE 802.11 protocols (e.g., WiFi), Bluetooth, Near-field Communication (NFC) (ISO/IEC 18092), ZigBee (IEEE 802.15.4), and/or Radio-frequency identification (RFID), to provide some examples.

The network router 220 can be configured to route data packets using one or more satellite communication technologies, including one of more global navigation satellite systems (GNSS) protocols that include, for example (but not limited to) Global Positioning System (GPS), the Russian Global Navigation Satellite System (GLONASS), the European Union Galileo positioning system (GALILEO), the Japanese Quasi-Zenith Satellite System (QZSS), the Chinese BeiDou navigation system, the Indian Regional Navigational Satellite System (IRNSS), and/or another GNSS protocol as would be understood by those skilled in the art.

The network router 220 can be configured to route data packets via one or more wired connections, such as Ethernet connections, fiber optic connections, and/or one or more other wired connections as would be understood by those skilled in the art.

In an exemplary embodiment, the network router 220 can include one or more embedded 4G/LTE broadband radio interfaces for true high speed connectivity to on-board applications, Dual 4G/LTE modem and SIM support for automatic failsafe backup through an alternative cellular broadband network, a robust mechanical and electrical design optimized for unattended vehicle cabinet installations, a WiFi 802.11 interface (including 802.11n, 802.11ac) with configurable operation mode (Access Point or Client), a multi-port Ethernet switch (e.g., 4-port, 8-port, etc.), a global navigation system, Hardware-based data encryption, software-based data encryption, Virtual Private Network (VPN) applications, and/or firewall features. In an exemplary embodiment, the network router 220 is Teldat LTE H1-Auto+ Router made by TELDAT USA, but is not limited hereto.

The transceiver 225 is configured to interface with the network router 220 and to transmit and/or receive wireless and/or wired communications via one or more wireless and/or wired technologies via antenna 230. The transceiver 225 can include processor circuitry that is configured to transmit and/or receive wireless and/or wired communications. The transceiver 225 can be configured to communicate with one or more medical facilities 140, emergency vehicle control or dispatch centers 142, and/or medical physicians 144, as well as with one or more other emergency vehicles 102 and/or facilities 104 via the network 110 and the access point 108.

The GNSS transceiver 240 is configured to interface with the network router 220 and to wirelessly transmit and/or receive GNNS communications via antenna 245. The GNSS transceiver 240 can include processor circuitry that is configured to wirelessly transmit and/or receive the GNSS communications. The transceiver 240 can be configured to communicate with one or more orbiting satellites. By communicating with one or more satellites, the GNSS transceiver 240 can communication with one or more medical facilities 140, emergency vehicle control or dispatch centers 142, and/or medical physicians 144, as well as with one or more other emergency vehicles 102 and/or facilities 104 via the network 110 and the global navigation satellite system (GNSS) 106. The GNSS antenna 245 can be configured to transmit and/or receive GNSS communication signals sent to/received from one or more orbiting satellites.

Those skilled in the relevant art(s) will recognize that the transceiver 225 and/or the GNSS transceiver 240 can also include (but is not limited to) a digital signal processor (DSP), modulator and/or demodulator, a digital-to-analog converter (DAC) and/or an analog-to-digital converter (ADC), an encoder/decoder (e.g., encoders/decoders having convolution, tail-biting convolution, turbo, Viterbi, and/or Low Density Parity Check (LDPC) encoder/decoder functionality), a frequency converter (including mixers, local oscillators, and filters), Fast-Fourier Transform (FFT), precoder, and/or constellation mapper/de-mapper that can be utilized in transmitting and/or receiving of wireless communications.

With continued reference to FIG. 2 and with reference to FIGS. 5A-5I, the antenna 230 can be configured to wirelessly transmit and/or receive communications via one or more wireless technologies. In an exemplary embodiment, the antenna 230 includes two di-pole antennas that provide continuous Physical layer signaling to mobile endpoints. In an exemplary embodiment, the antenna 230 is a dual di-pole antenna configured for one or more cellular and/or non-cellular communication protocols. For example, antenna 230 can be a 4G LTE di-pole antenna in small form-factor radome that enables signal transmission and reception with horizontal and vertical polarities. This configuration allows for uninterrupted signal reception in a moving emergency vehicle, including at speeds over 80 Mph. The antenna 230 is configured to maintain signal connection as the vehicle 102 moves between multiple cellular towers. In an exemplary embodiment, the antenna 230 is a multiple-input and multiple-output (MIMO) antenna. The antenna 230 can be an antenna array that includes two or more antenna elements.

In an exemplary embodiment, antenna 230 is a Venti CORE™ antenna solution that is a 2-port MIMO antenna incorporating one or more vertically polarized antennas and one or more true horizontally polarized antennas, but is not limited thereto. In an exemplary embodiment, the antenna 230 includes a single vertically polarized antenna and a single horizontally polarized antenna. In this example, the use of both a true horizontal and a vertical antenna in a MIMO antenna configuration that utilizes polarization diversity to deliver higher data rate throughput and greater coverage.

In an exemplary embodiment, antenna 230 supports all carrier frequency bands covering 698-960, 1,710-2,700 MHz on both ports, but is not limited to these frequency bands. The isolation of the two antennas is greater than 20 dB at every frequency. Typical VSWR is 1.3:1 (vertical) and 1.5:1 (Horizontal). The radome can be made of, for example (but not limited to), UV-ABS plastic and is designed for roof mounting on ambulances, but it not limited thereto. In an exemplary embodiment, the antenna dimensions are 6.53"W×15.55"L×5.62" H, but are not limited thereto.

Figure 5A:
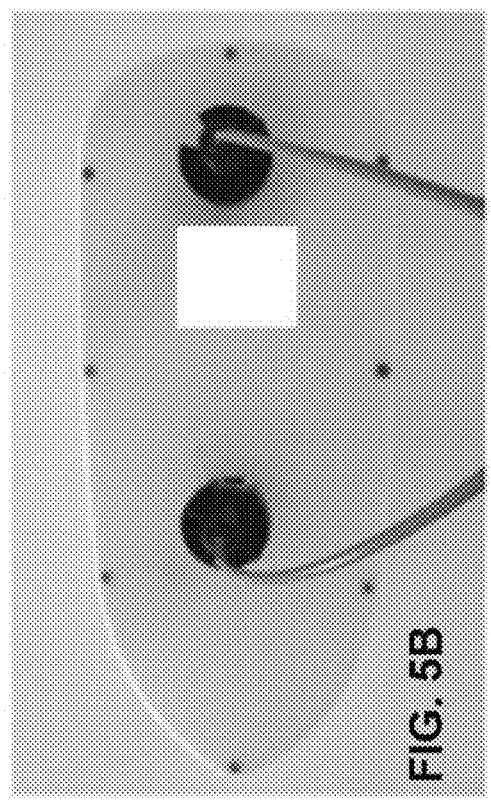
FIGS. 5A-5K illustrate antenna systems according to exemplary embodiments of the present disclosure.
Figure 5B:
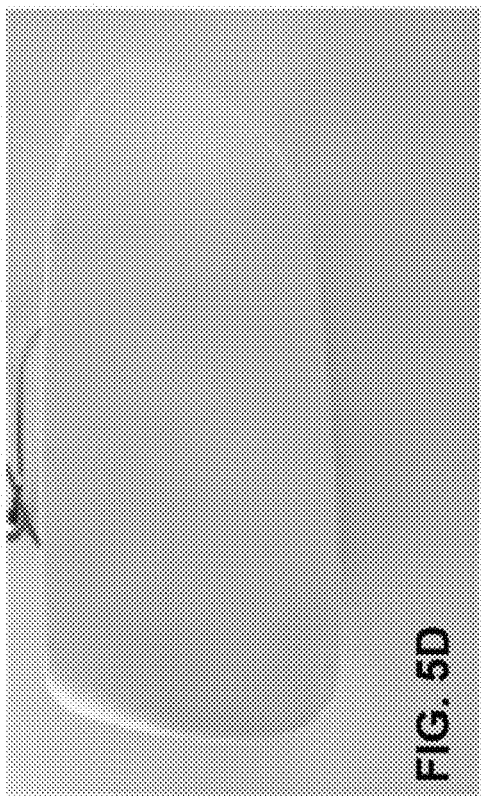
Figure 5C:
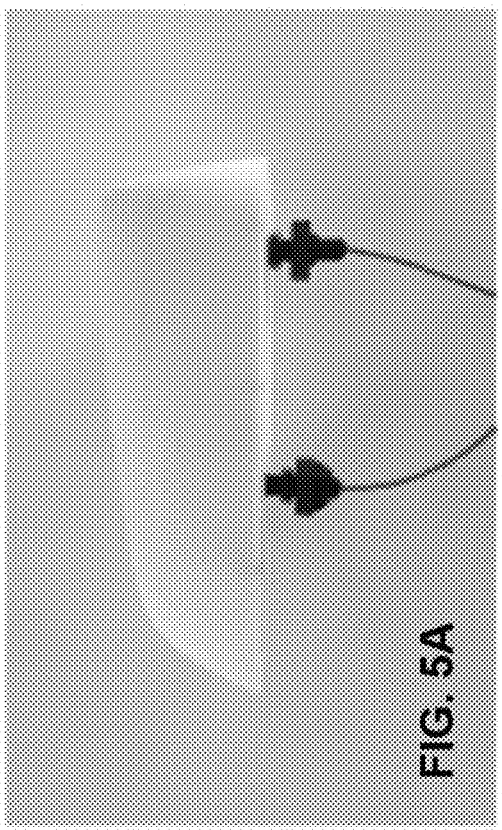
Figure 5D:
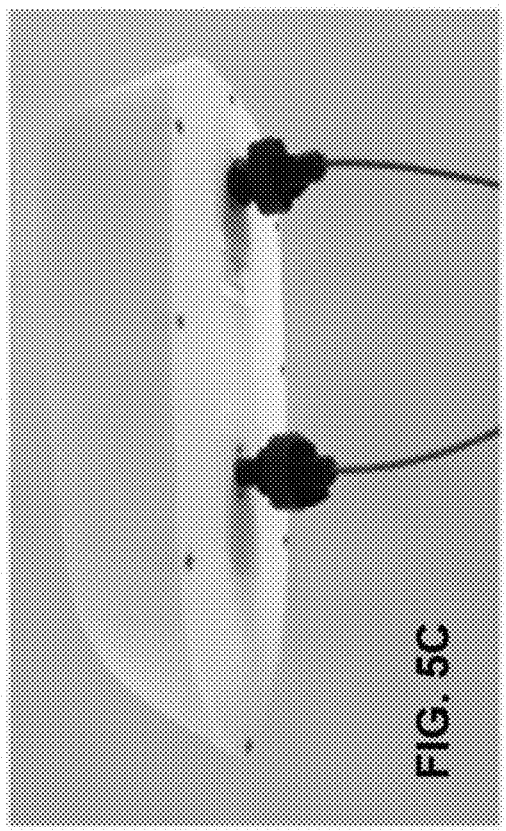
Figure 5E:
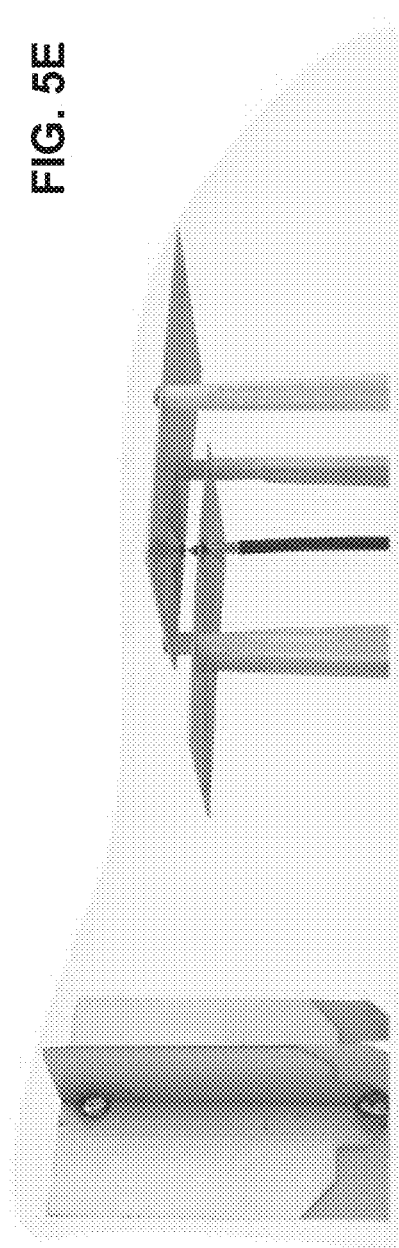
Figure 5F:
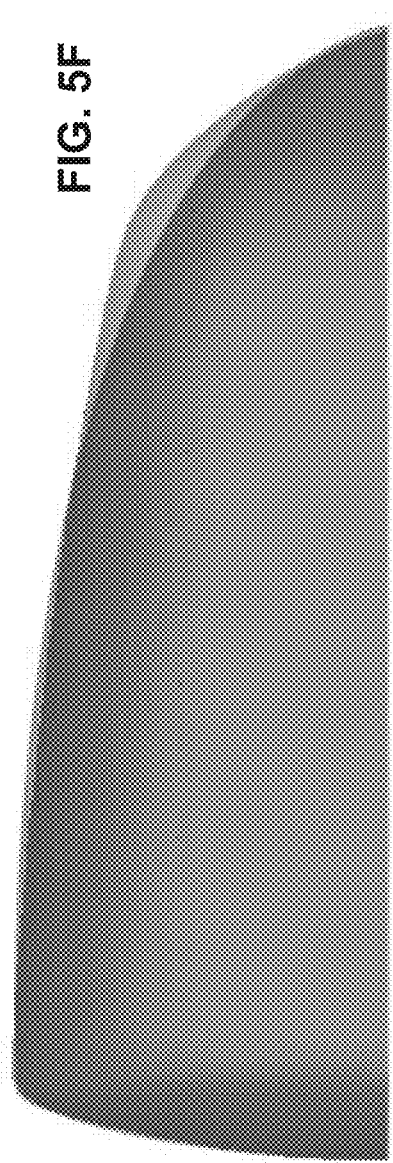
Figure 5G:
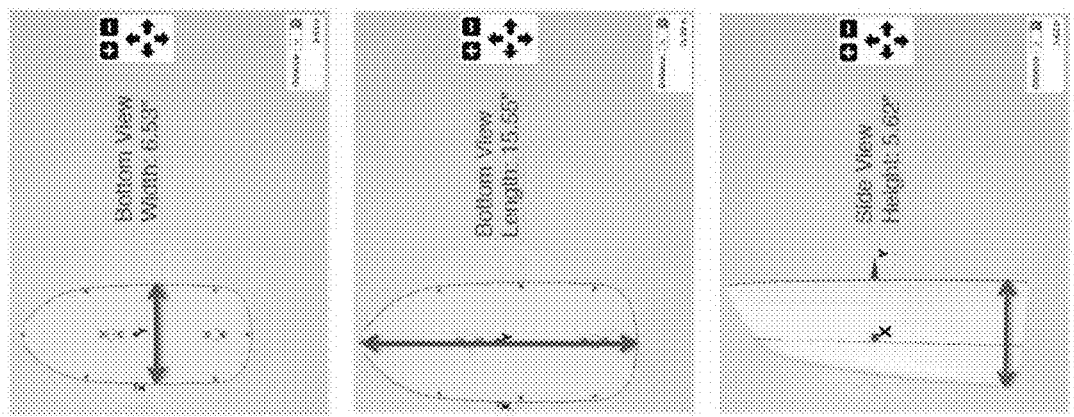
Figure 5I:
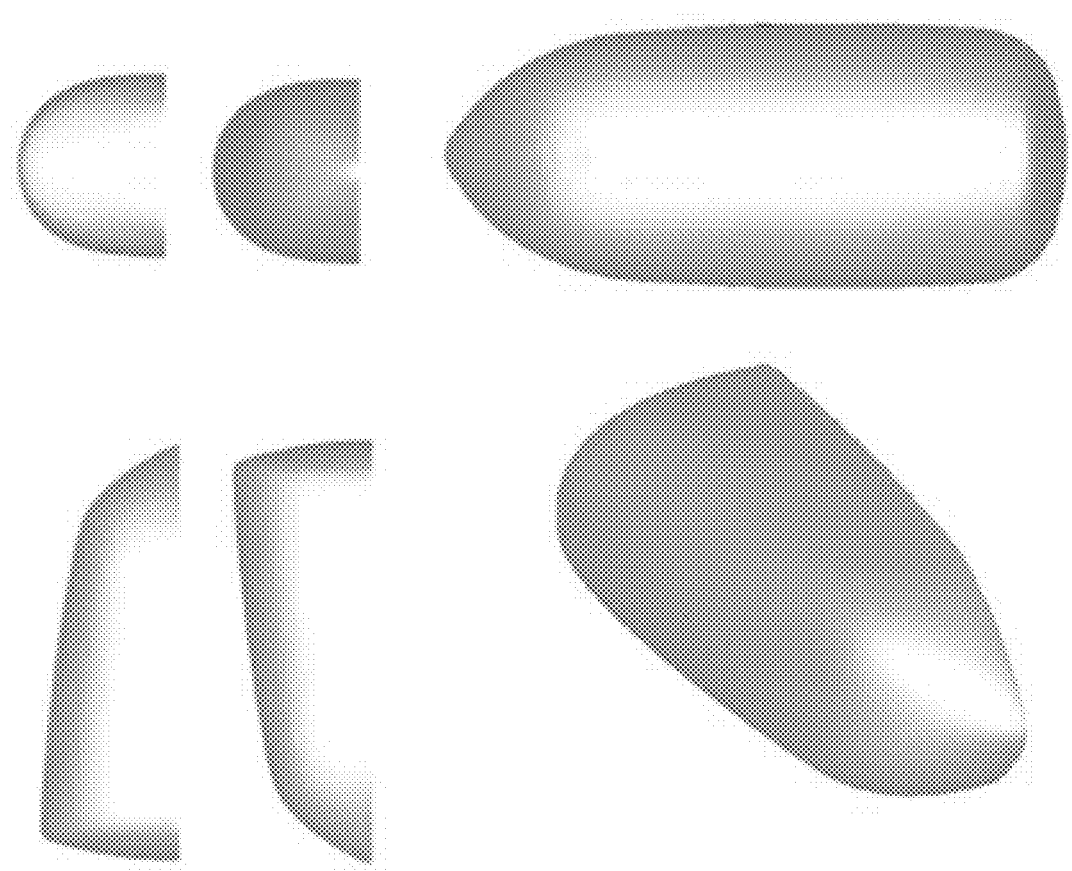
Figure 5H:
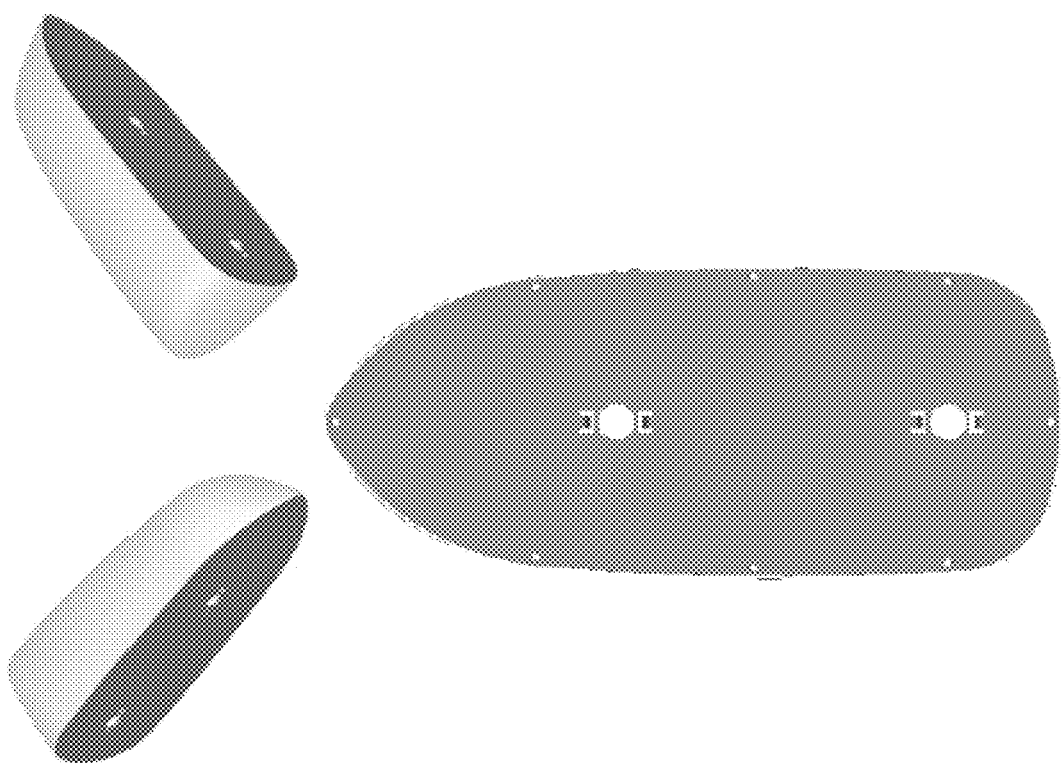
Figure 5K:
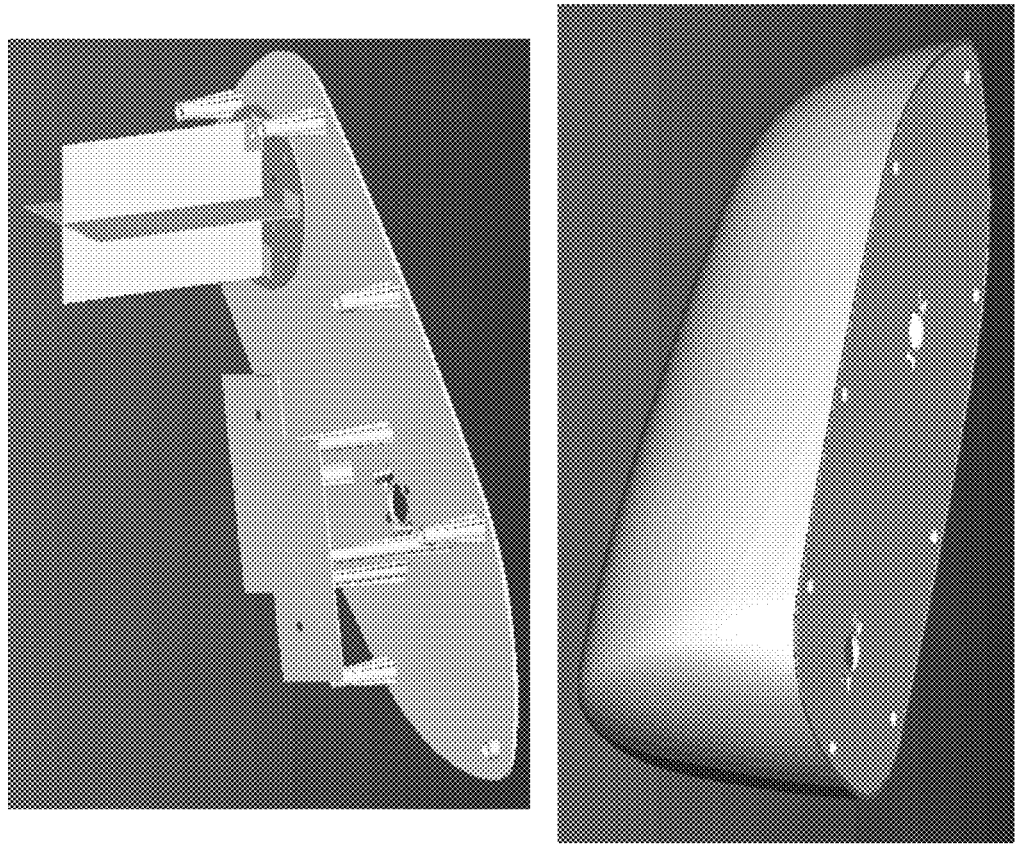
Figure 5J:
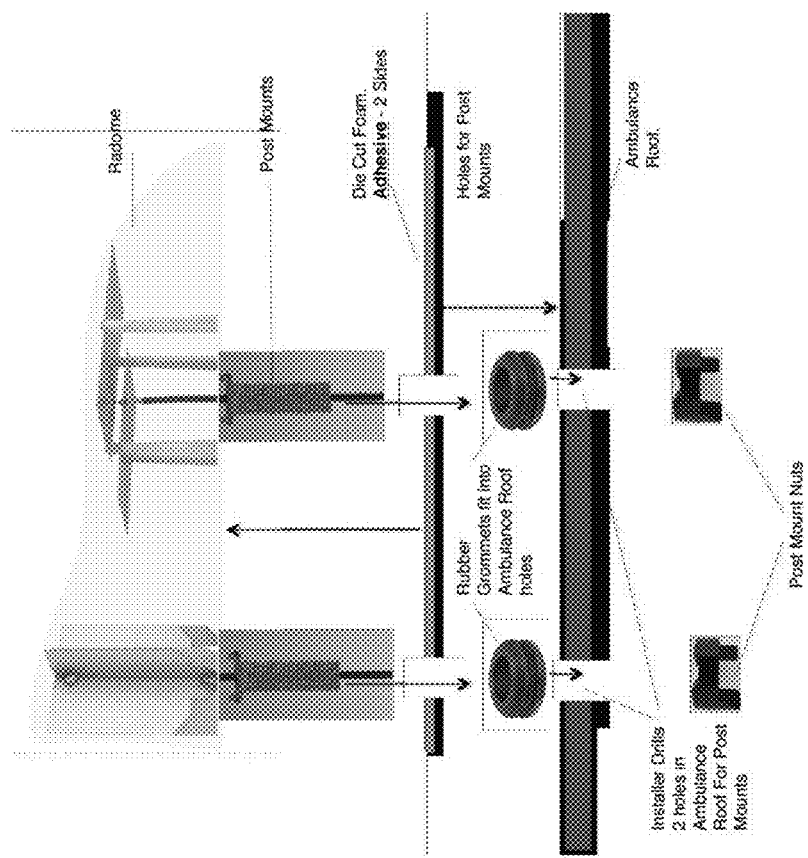

FIGS. 5A-5K illustrate exemplary radome enclosures and antenna systems according to exemplary embodiments of the present disclosure. The radome enclosures can be configured to house di-pole antenna elements (e.g., two elements) of the antenna 230. FIG. 5A shows a left-side view; FIG. 5B shows a bottom view; FIG. 5C shows a perspective view taken from the bottom, left side thereof; FIG. 5D shows a perspective view taken from the top, left side thereof; FIG. 5E shows an internal side view that illustrates an example arrangement of the antenna elements; FIG. 5F shows right-side view; FIG. 5G shows two cross-sectional views (taken along X and Y) and a right-side view that shows the locations of the X and Y sections; FIG. 5H shows three views: a bottom view, a perspective view taken from the bottom, right, front side thereof, and a perspective view taken from the bottom, right, back side thereof; FIG. 5I shows six views: a right-side view, a left-side view, a back view, a front view, a top view, and a perspective view taken from the top left, front side thereof. FIG. 5J illustrates an interior view of a radome housing an antenna system that is mounted to an emergency vehicle; and FIG. 5K shows two views: a bottom support member having two di-pole antenna elements mounted thereto, and a perspective view of the bottom support member having a radome placed thereon that is taken generally from the bottom, back left-side thereof.

With reference to FIGS. 5A-5E, 5J and 5K, the antenna 230 includes two di-pole antenna elements, one disposed in the radome near the back end of the radome and the other closer to the front of the radome. The first antenna element of the antenna 230 located at the back end can include vertically-arranged antenna radiator planes. In an exemplary embodiment, the radiators can be configured in a plus (+) shaped arrangement when viewed from the top of the arrangement. In an exemplary embodiment, the first antenna element can be configured as a vertically polarized antenna. The second antenna element of the antenna 230 located near the front end of the radome can include one or more horizontally-arranged antenna radiator planes. For example, the second antenna element can include two more horizontally-arranged antenna radiator planes that are arranged in the same horizontal plane. In an exemplary embodiment, the second antenna element can be configured as a horizontally polarized antenna. In an exemplary embodiment, the antenna 230 is externally disposed on the vehicle 102 and connected to the transceiver 230 located within the interior of the vehicle 102. The Returning to FIG. 2, the imaging modality 250 is configured to generate one or more imaging modalities of a patient. The imaging modalities can include, for example (but not limited to), ultrasound images such as, carotid, transcranial Doppler (TCD), and/or Transcranial Color Coded Doppler (TCCD), photoacoustic spectroscopy, and phased array ultrasound. The Doppler imaging can include both two-dimensional (2D) and three-dimensional (3D) imaging. The imaging modalities are limited thereto and can include, for example (but not limited to), computed tomography (CT) imaging, positron emission tomography (PET) imaging, single-photon emission computed tomography (SPECT), X-ray imaging, magnetic resonance imaging (MRI), nuclear magnetic resonance imaging (NMRI), magnetic resonance tomography (MRT), and/or another imaging technology as would be understood by those skilled in the relevant arts. In an exemplary embodiment, the imaging modality 250 is a helmet and collar device configured to generate medical images of blood vessels of the brain and neck region of the patient. In an exemplary embodiment, the telemedicine system 200 can use raman spectroscopy and/or other molecular diagnostic techniques in addition to, or alternatively to, these imaging modalities. In an exemplary embodiment, molecular analysis can be performed on, for example (but not limited to), serum, plasma, cells, and/or other tissue, but is not limited hereto. Exemplary imaging modalities and other diagnostic technologies are described in more detail in the "Exemplary Imaging Modalities and Diagnostic Technologies" section below.

The imaging modality 250 can be configured to generate 2D and 3D Carotid Doppler images, Transcranial Doppler images, and/or Interventional angiography. The imaging modality 250 can be configured to perform brain and neck vessel angiography to visualize brain and neck artery anatomy with contrast. Using the generated images, it can be determined if a patient should receive an intra-arterial clot buster solution or if a clot retrieval or other surgical procedures to physical remove clot from neck (carotid) arteries should be performed. For example, these techniques can facilitate delivery of clot buster to blocked arteries or the unblocking of arteries with intra-artery clot buster or clot retrieval with or without stenting. The images can also be used to verify a successful removal of the obstruction. Oxygenation efficacy of damaged and surrounding tissue can be assessed with carotid and/or transcranial Doppler, phased array, and photoacoustic spectroscopy.

The imaging modality 250 can provide real time analysis of blood flow velocity and flow direction and other neck and brain blood flow measures in a pre-hospital situation as the patient is being transported to a medical facility in the vehicle 102. For example, carotid Doppler and transcranial Doppler and phased array ultrasound can be used to provide this analysis.

In exemplary embodiments, a potential stroke can be identified by providing brain insight data to the medical personnel in advance of the patient's arrival. The telemedicine system 200 can provide a depiction of, for example (but not limited to), the middle cerebral arteries, carotid arteries, and basilar Artery. Tomography of oxygenation in various (e.g., three) regions of middle cerebral artery territory and various (e.g., two) regions of basilar artery can also be performed.

Figure 3:
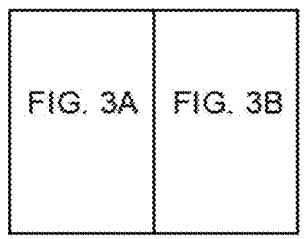
FIGS. 3A and 3B illustrate a telemedicine system according to an exemplary embodiment of the present disclosure.
Figure 3A:
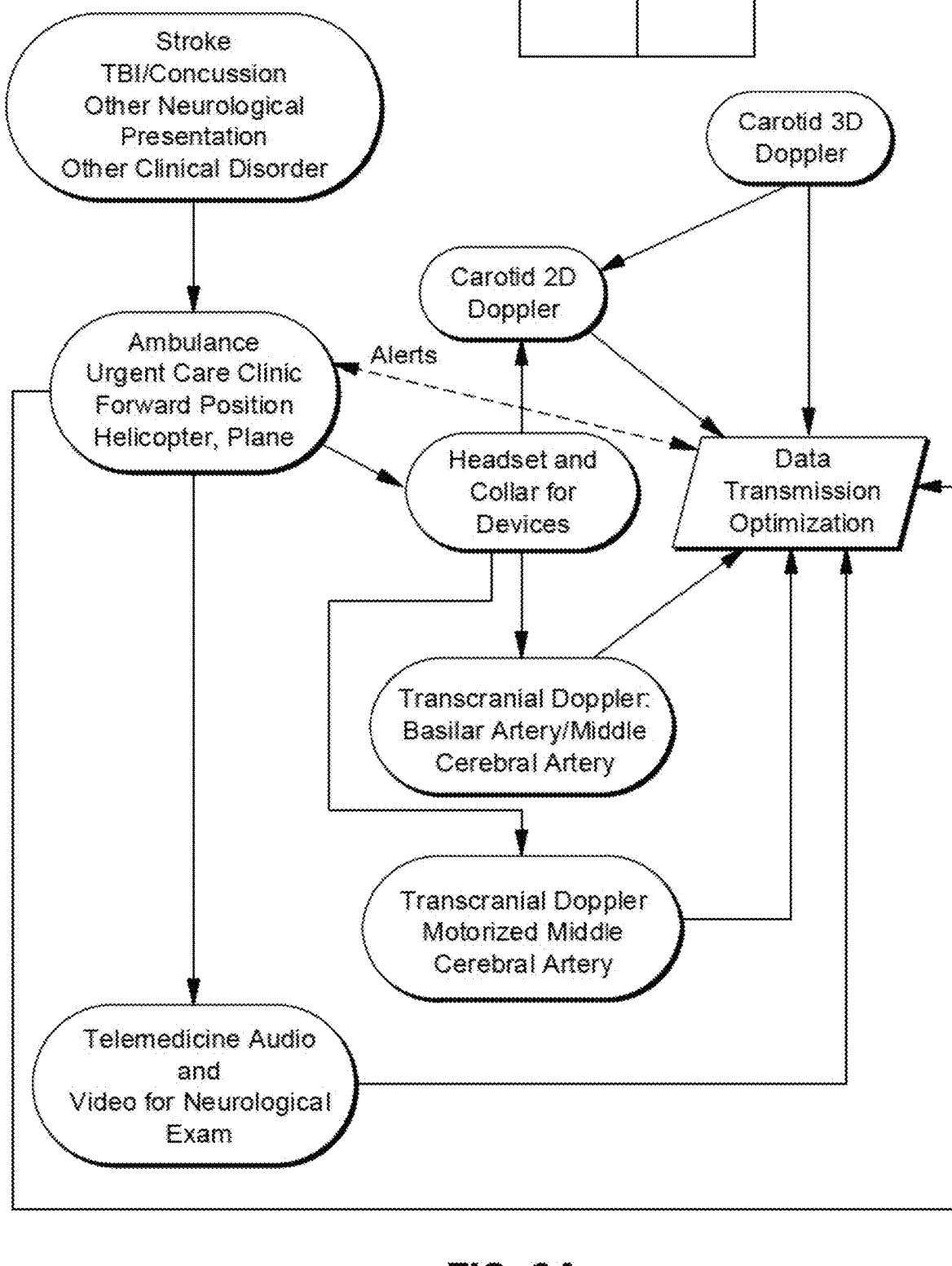
Figure 3B:
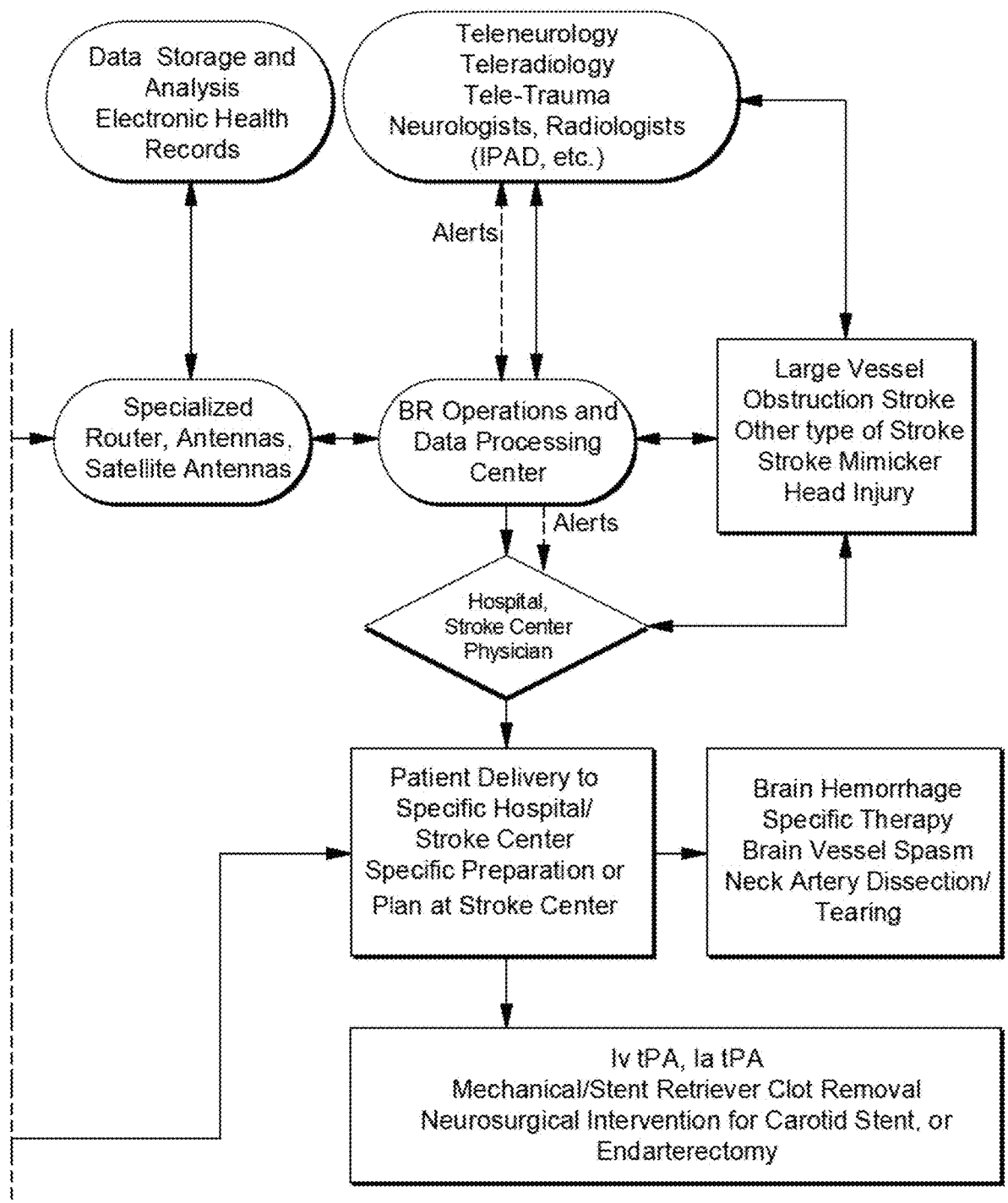

FIGS. 3A & 3B illustrate a telemedicine system 300 according to an exemplary embodiment of the present disclosure. The system 300 shown in FIG. 3 illustrates the interaction of components of a telemedicine system, the operations performed by the components, and the interactions between the various components. In the telemedicine system 300, a patient with a stroke, a traumatic brain injury (TBI), other neurological disorder, or other clinical disorder presents in an emergent situation in a civilian or military context and is evaluated and transported in an ambulance, seen and then transported if appropriate from an urgent care clinic, helicopter, plane, or other moving vehicle. At the point of care and during transport, real time neurological examination with a NIH Stroke Scale is performed by telemedicine evaluation as shown in FIG. 3 using the telemedicine systems illustrated in FIGS. 1-2 that include optimized connectivity and audio video quality (Data transmission optimization), in particular in rural and urban areas or in forward military positions in conjunction with wireless and cellular towers and with satellites in some circumstances. Large head vessels, particularly the basilar artery and middle cerebral artery can be imaged with, for example (but not limited to), transcranial Doppler or transcranial color-coded Doppler. The large neck vessels, the carotid arteries are evaluated by, for example (but not limited to), 2D and 3D carotid Doppler. The neurological and radiological examination is performed by experts and the vascular examination is facilitated by a helmet with probes, which is easy to apply. The data optimization is fostered by software and hardware, including routers and antennas, in conjunction with cellular towers, wireless access points and/or satellite communications. Data is transmitted to an operation center which directly involves the neurologists and neurologists where a diagnosis of large vessel obstruction or stenosis might be suggested, or another disorder, such as a brain hemorrhage or brain trauma with vessel spasm or vessel tearing or other neurological disorder. The operations center staff and the consulting neurologists and radiologists can communicate directly with the ambulance, the ambulance dispatch, the ambulance medical director or other facility personnel in real time as well as hospital personnel, including emergency department physicians, neurologists, and to other physicians. A decision is made where to transport and what to prepare at the institution by the receiving hospital. If a stroke, clot buster may be warranted or clot retrieval may be needed. The operations center also can also develop data within an electronic health record that may be transmitted to the hospitals electronic health record system or by fax. Data storage and analysis sub-acutely can also occur from the operations center. Alerting from the ambulance on pickup to the operations center lead to triggering of alerting to tele-neurologist/tele-radiologist, who then can alert back to the operations center when their evaluation is completed. This is followed by alerting to the hospital, hospital physicians, ambulance, and/or ambulance dispatch. The operations center performs a critical role in coordinating all efforts for care prehospitally during delivery to the appropriate hospital and specialists, where further evaluation and therapy can be delivered, when warranted. Exemplary embodiments herein are directed to systems of care predicated on telemedicine and physiological and neurological evaluation that may optimize the quality and process of care with initiation of early, safe, and appropriate diagnosis and therapy that may improve prognosis and prevent death.

In an exemplary embodiment, upon the presentation of stroke or other brain injury symptoms in a person, an emergency vehicle (e.g., ambulance, plane, helicopter, etc.) can be dispatched to the person. Or the person can be taken to an urgent care facility by other means.

In an ambulance scenario, ambulance personnel can evaluate a stroke in the field or on the ambulance's way to a medical facility using a telemedicine system such as the system 200. Multimedia (audio, video) information of a neurological exam to an operations center. Additionally, one or more imaging modalities can be used to capture medical images that can be transmitted to the operations center. The operations center can communicate with one or more medical facilities, including one or more medical professional either at the facility or remotely located. Based on the examination results, the operations center can direct the emergency vehicle to an appropriate facility as well as instruct the facility prepare for the arrival of the patient.

The ambulance can be outfitted with a telemedicine system configured to send valuable telemetry to the medical facility ahead of the patient's arrival. A neurological examination using, for example (but not limited to), the NIH stroke scale would be performed. A Transcranial Doppler of Bilateral Middle Cerebral Arteries and Carotid Arteries and then Basilar Artery can be performed. These arteries are the large arteries that can cause the most severe stroke and that would be amenable to intravenous or intra-arterial therapy. In exemplary embodiments, depending on the length of the ambulance ride, the neurological examination and ultrasound examinations could be repeated or could be continuous to provide ongoing data about the patient during transport.

FIG. 4 illustrates a telemedicine system 400 according to an exemplary embodiment of the present disclosure. The system 400 shown in FIG. 4 illustrates the interaction of components of a telemedicine system, the operations performed by the components, and the interactions between the various components, including the interactions between software and hardware components, as well as the flow of information and data. With reference to FIG. 4, alerts and hardware and/or software are illustrated for the ambulance telemedicine evaluation. The ambulance and the ambulance paramedics and crew pick up the patient and an ambulance electronic health record is begun (1). At the same time (2), an alert is sent to the operations center and a patient case is opened. An alert (3) is sent to the expert teleneurologists, telestroke specialists, and teleneuroradiologists that a case has begun and evaluation of the patient by telemedicine and ultrasound begins immediately by these physicians in the ambulance or other moving vehicle (4). A consultation is generated by these physicians using a template at the operations center (4). The operations center is alerted as the examination is completed (5). The operations center at (6) sends an alert and starts a telemedicine communication with the operations center, the evaluating expert neurologists and radiologist, Ambulance, Ambulance Medical Director, the potential receiving hospital, i.e. primary or comprehensive stroke center, and the formal physician consultation is sent to the hospital and stroke center. The ambulance Medical director, hospital, and stroke neurologists then make decisions at to destination for patient delivery, preparation and studies to be done on patient at receiving hospital, including special and personnel needed for potential clot buster and endovascular clot retrieval procedures. The telemedicine and ultrasound and other evaluations to be determined are sent to an AV archive (7) and all notes, alerts, measures, accounting and other data for the specific patient encounter are sent to the AV archive (7). All initial data from the encounter is sent to a secure data warehouse and a backup warehouse (8). Data is available for big data analytics from this data warehouse in collaboration with the operations center and the telemedicine group.

Data from the destination hospitals, including neurological examination and imaging examinations, therapy, hospital records, and measures, i.e. time to therapy, time to diagnosis, success measures, acute and subacute outcome measures are also sent to the operations center and data warehouse (9).

Figure 6:
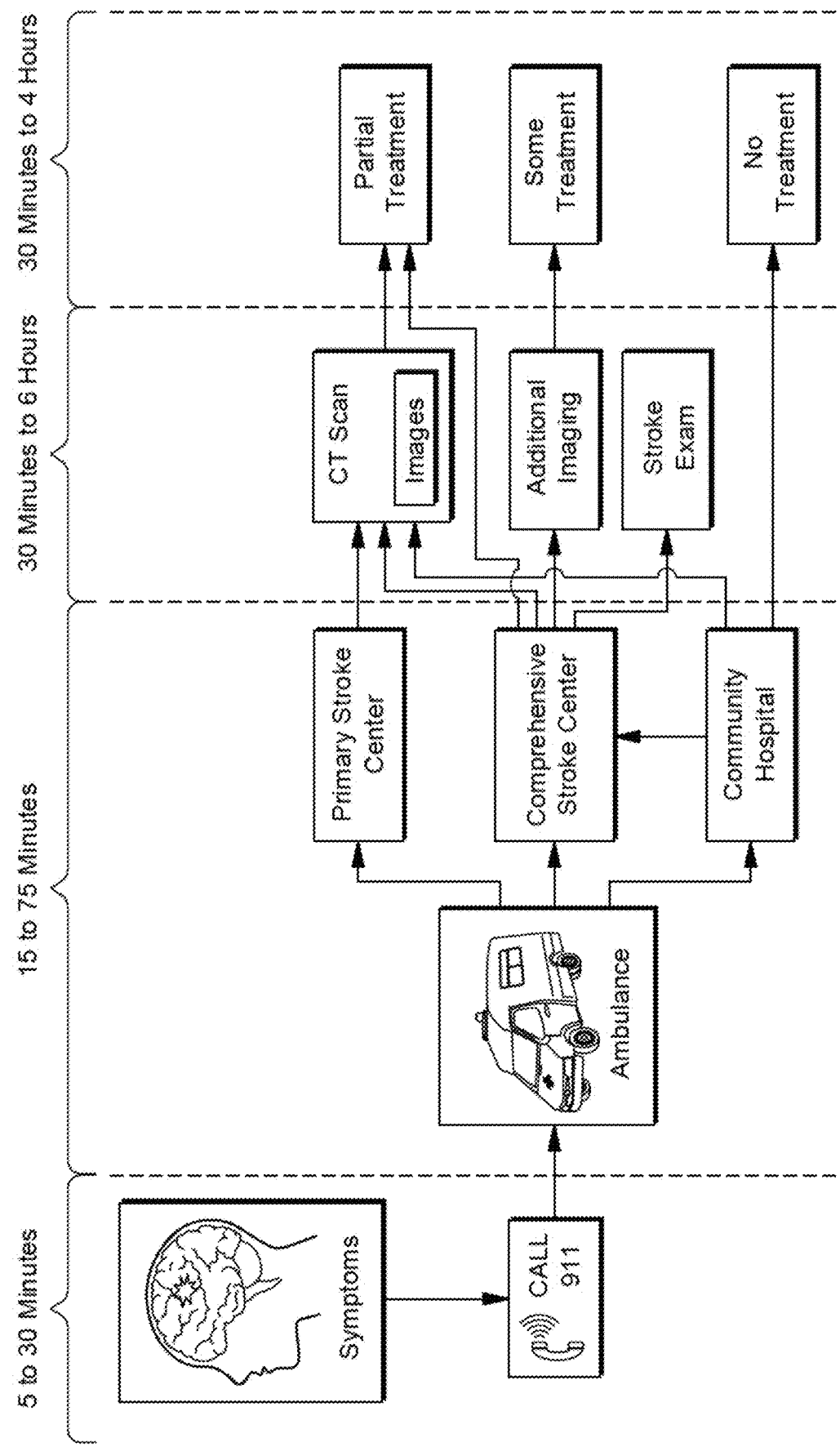
FIG. 6 illustrates an example emergency response sequence according to exemplary embodiments of the present disclosure.

FIG. 6 illustrates an example emergency response sequence 600. Upon the presentation of stroke or other brain injury symptoms, emergency services can be contacted (e.g., a call to 911), which dispatches an emergency vehicle and personnel to the person. The emergency vehicle can transport the patient to a stroke center or hospital where medical images can be taken, including vessel imaging, and appropriate medical treatments can be performed. In this response sequence, substantial time has passed before the patient receives the appropriate treatments, such as treatment for stroke. This delay in treatment can significantly reduce recovery while increasing long-lasting or permanent stroke effects and mortality rates. FIG. 6 illustrates an example emergency response sequence 600 for, for example (but not limited to), stroke (but is not limited to stroke treatments). The patient develops neurological symptoms that might be consistent with a stroke and a 911 call is made. An ambulance is dispatched and the crew does an evaluation. Depending on their evaluation and that of dispatch center, the patient may be sent to a primary stroke center (shown) or a stroke ready center or in some cases to a comprehensive stroke center. In rural settings, this may be a non-stroke center or a stroke ready hospital. Larger urban centers may have preponderance of primary stroke centers and one or more comprehensive stroke centers. Time for transport to the hospital will depend on the time for an ambulance to arrive, evaluation at the site and clinical care, and then transport to a hospital. A medical record is generated in the ambulance that may be on paper or electronic. A certain time range is illustrated. In a typical situation, the patient arrives to a stroke ready or primary stroke center and the hospital is alerted about a potential stroke. Hospitals may have a stroke alert, mobilization of a stroke team, and as the patient arrives the protocol varies even though there is a national standard for stroke protocols. The emergency department may not be optimized for strokes and usually an initial examination by the emergency physician is done, a neurologist is called, and a CT scan is done. Neurologists may not be available and may have variable time before they can arrive for examination. Radiologists skilled in stroke evaluations may not be available. Alternatively, a Tele-stroke cart or robot in the emergency department may allow distant communication and real time with a neurologist. A neurological examination with a formal NIH Stroke Scale is performed, but this may or may not involve a stroke neurologist. A decision after considering exclusions and inclusions, the time of initial stroke onset, the CT scan, and neurological examination is then made to give or not give tPA. This process is variable across different primary and stroke ready hospitals, as illustrated. The Golden Hour delivery from symptom onset to tPA administration may be achieved and carries with a better prognosis. The longer the delay of clot buster in warranted and safe situations, the poorer the prognosis with a range up to 4.5 hours. In some stroke ready and primary stroke centers, the ability to image vessels by CT angiography or MR angiography in combination with the neurological examination and CT scan may suggest a large vessel stroke. The patient can then be transferred to a comprehensive stroke center, where there is the capacity to perform clot retrieval with stent retrievers or other devices in combination with cerebral angiography. The time delay is significant in these cases where the patient first goes to a primary stroke center and then to a comprehensive stroke center. However, clot retrieval can occur, depending on the case and center up to 6 to 8 hours after stroke onset or up to 12 hours after stroke onset. Longer lengths of time are not ideal for tPA or for clot retrieval as more brain is at risk for death. Again, time from stroke onset to therapy is critical for prognosis. In some cases, the patient may be delivered to a comprehensive stroke center, that has 24/7 neurology coverage, imaging modalities, and both tPA and clot retrieval available. The time and prognosis is better in this primary transport to a comprehensive stroke center.

Figure 7A:
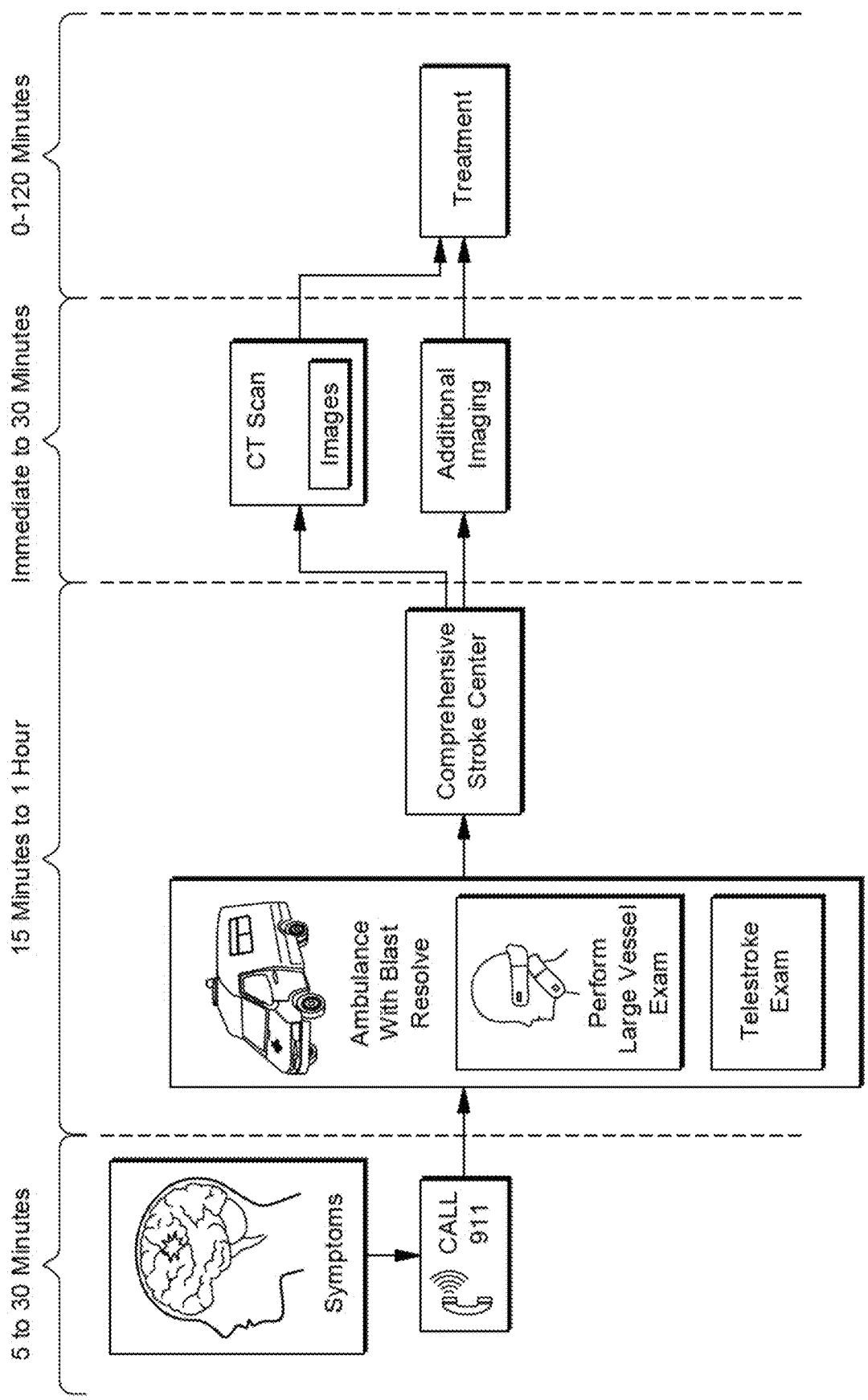
FIG. 7A illustrates an emergency response using a telemedicine system according to exemplary embodiments of the present disclosure.

FIG. 7A illustrates an emergency response 700 of brain injuries and medical treatments in response to the presentation of brain injury symptoms using a telemedicine system according to exemplary embodiments. An alternative to the general protocol in FIG. 6 is to perform pre-hospital neurological evaluation and vascular evaluation of the large vessels in the ambulance or other moving vehicle. As illustrated in the present disclosure, quality real time, neurological examination including a NIH Stroke Scale, is performed by an expert vascular neurologist. Data on the large vessels for stenosis or obstruction is obtained with carotid and transcranial Doppler in real time. If these studies and neurological examination suggests a large vessel stroke, the patient can be transferred directly to a comprehensive stroke for tPA, angiography, and clot retrieval of brain vessel obstructions or stenting or endarterectomy of neck vessel stenosis or obstruction. The time is shortened to definitive therapy and the ED and appropriate physicians and other services are alerted and prepared for the patient, whether that involves CT, other vessel imaging modalities, or catheterization for clot retrieval or surgery to remove neck clots or obstruction. The change of accurate diagnosis and improved prognosis as well as reversal is enhanced by changing the process and logistics for the patient. If the patient can only go to a primary stroke center, similar benefits are seen with earlier use of tPA clot buster and then transfer can occur, if warranted.

Figure 7B:
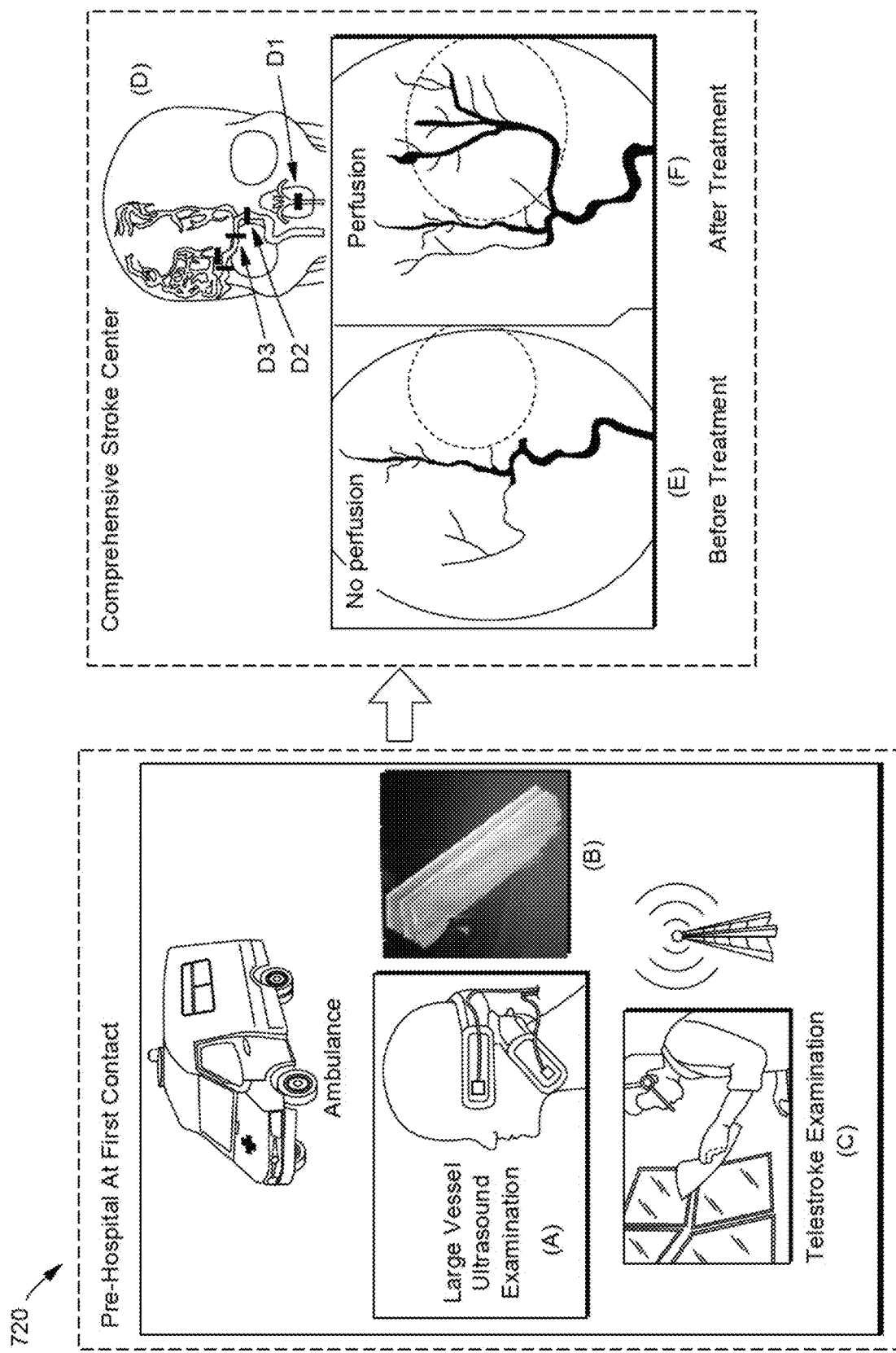
FIG. 7B illustrates an emergency response using a telemedicine system according to exemplary embodiments of the present disclosure.

Upon the presentation of stroke or other brain injury symptoms, emergency services can be contacted (e.g., a call to 911), which dispatches an emergency vehicle and personnel to the person. With an emergency vehicle (e.g., ambulance, plane, helicopter, etc.) that includes a telemedicine system such as the system 200, a neurological exam can be performed in the emergency vehicle and corresponding multimedia (audio, video) information of the exam is transmitted to an operations center, as well as one or more medical facilities. Additionally, one or more imaging modalities can be used to capture medical images that can be transmitted to the operations center and/or medical facilities. Upon arrival at the medical facility, appropriate medical treatments can be performed (e.g., intravenous or intra-arterial therapy). FIG. 7B illustrates an emergency response 702 using a telemedicine system according to exemplary embodiments. As shown, a neurological exam can be performed in the emergency vehicle and corresponding multimedia (audio, video) information of the exam as well as medical images from one or more medical imaging modalities (e.g., helmet and neck imaging device) are transmitted to an operations center, as well as one or more medical facilities. FIG. 7B is expanded to show Telestroke evaluation by neurology and radiology (Panel C) with cellular and/or satellite and the large vessel examination with special apparatus to allow easy application of probes for looking at the neck and head vessels with ultrasound (Panel A). A typical 3D carotid Doppler picture of the carotid artery is demonstrated (Panel B) and it is evident that obstruction can be observed if present. This can be obtained within 30 seconds per carotid artery. The expert neurological and radiological examination of the Dopplers is illustrated distally in real time. Large vessel strokes can result from obstruction or stenosis in the basilar artery (D1), the carotid artery (D2), or the middle cerebral artery (D3). These large vessel strokes have the potential with more significant injury and disability. Imaging at a comprehensive stroke can show obstruction of the middle cerebral artery (Panel E) and with clot retrieval with use of retrieval devices, such as a stent retriever, revascularization is demonstrated with re-perfusion of areas that were not getting blood flow or oxygen. The exemplary embodiments are developed to promote this type of result.

By using telemedicine systems according to the exemplary embodiments described with increase network connectivity, treatment success rates performed at trauma centers for brain injuries such as stroke are significantly increased.

Exemplary Imaging Modalities and Diagnostic Technologies

The following discussion includes example imaging modalities and other diagnostic technologies that can be implemented in the telemedicine systems of the exemplary embodiments of the present disclosure.

2D and 3D Carotid Doppler, Transcranial Doppler and Interventional angiography

Embodiments described herein use direct interventional therapy, which initially can involve brain and neck catheter-based angiography. Brain and neck vessel angiography, which visualizes brain and neck artery anatomy precisely with contrast, is warranted in those patients appropriately selected to get intra-arterial clot buster or clot retrieval or in surgical procedures to physical remove clot from neck (carotid) arteries. These techniques are generally the standard in brain and neck vessel definition, with particular relevance to obstruction and collateral blood flow. These techniques provide the platform for delivery of clot buster to blocked arteries or unblocking of those arteries with intra-artery clot buster or clot retrieval with or without stenting. These techniques also provide information after the obstruction clearing attempts at successful opening of the blocked or obstructed vessels. These angiography techniques only provide an anatomical picture but no information on tissue efficacy of potentially damaged tissue before, during, or after the procedure. Oxygenation efficacy of damaged and surrounding tissue at these times cannot be assessed with angiography but could be intravascularly assessed with carotid and/or transcranial Doppler, phased array, and photoacoustic spectroscopy.

Additionally, in exemplary embodiments, real time analysis of blood flow velocity and flow direction and other neck and brain blood flow measures is not available pre-hospital or in the Emergency Department. These can be provided with carotid Doppler and transcranial Doppler and phased array ultrasound. Also, known techniques, except transcranial Doppler, are unable to detect and characterize brain or neck artery emboli, define vessel plaque characteristics, and measure vessel-wall thickness (carotid Doppler with intimal thickness).

In another embodiment, a method for allowing an ambulance crew or EMTs (Emergency Medical Technicians) to evaluate a stroke out in the field or on the ambulance's way to the E.R., (it should be appreciated that ER, emergency room,) the ambulance would be outfitted with the present invention which would send valuable telemetry to the E.R. ahead of the patient's arrival. The steps would include dispatching an ambulance and EMT to the patient. A neurological examination with a NIH stroke scale would be performed. A Transcranial Doppler of Bilateral Middle Cerebral Arteries and Carotid Arteries and then Basilar Artery would be performed (These are the large arteries that can cause the most severe stroke and that would be amenable to intravenous or intra-arterial therapy). In an exemplary embodiment, depending on the length of the ambulance ride, the neurological examination and ultrasound examinations could be repeated or could be continuous to provide ongoing data about the patient during transport.

Brain and Neck Ultrasound Examination

Transcranial Doppler and Carotid Doppler provide for real time analysis of brain and neck blood flow that compliment anatomical representations of brain and neck arterial anatomical imaging, i.e. CT and MR angiography of head and neck. A piezoelectric crystal emits ultrasound pulses and listens for reflected echoes (sound waves). The reflected echoes may provide time of flight, intensity, or frequency data of the reflected versus the transmitted wave. Velocity of blood flow is based on the calculated frequency shift of reflected waves.

Both transcranial and carotid Doppler are performed in a standard sequence that involves placement upon sites to insonate the vessels, listening for the sound of blood flow that may reflect on normal flow or obstructed flow, and determination of anatomical vessel characteristics (carotid Doppler), spectral analysis with blood flow velocity and pulse wave determination (carotid and transcranial Doppler), adventitial embolic signals (transcranial Doppler), power m mode (transcranial Doppler) and comparison of anatomical and blood flow velocity and wave anatomy with known, established, and normal standards to determine normal versus abnormal, including determination of abnormal vessels with degree of stenosis and obstruction. Low or elevated blood flow may reflect on local pathology of the neck or brain blood vessels or the efficacy of blood flow from the heart, i.e. cardiogenic shock, cardiac valve disorders, or sepsis. Rapid and real time transcranial Doppler and carotid Doppler can identify critical stenosis or obstruction in specific neck and brain blood vessels that will provide information for correct hospital transport, hospital preparation for stroke intervention, appropriate treatment selection, and time savings to save brain cells.

In exemplary embodiments, Transcranial Doppler can be used for other measures that reflect on brain intracranial pressure and vessel reactivity that can reflect on conditions of increased brain pressure, related to traumatic brain injury, brain swelling from many causes, or large stroke with brain swelling.

Carotid Doppler

Vascular duplex ultrasound of the carotid Doppler involves 2 ultrasound components, B-mode Gray Scale (2-D imaging) and Doppler imaging including flow measurement, color Doppler and spectral Doppler with blood flow velocity measurement. In an exemplary embodiment, carotid Doppler will include the above elements and will be recorded with a previously validated (NASA Space Simulator) carotid Doppler system and transducers affixed to the bilateral carotid arteries. The transducer will be a standard 4 cm or larger convex as opposed to linear transducer. A single sampling point will be used as opposed to multiple sampling points for proximal, middle, and distal carotid arteries. Raw imaging data will be sent wirelessly to the data/operations center, processed there, and analyzed similar to the transcranial Doppler ultrasound. The carotid Doppler probes will be used to evaluate the carotid arteries and the neck vertebral arteries. The carotid Doppler probe will be incorporated into the neck portion of the helmet (see, e.g., FIGS. 7A, 7B (Panels A and B) & 10). The internal carotid artery is particularly relevant for stroke.

B mode or gray scale imaging can look at the carotid artery and associated anatomical vessel and other structures in transverse or longitudinal plane. B mode is useful for defining the internal carotid artery wall and characterizing, localizing and defining extent and size of low or high echo structures, including atherosclerotic plaque, that may be obstructing the vessel, i.e. internal carotid artery. Plaque usually results from aging change and pieces of plaque may dissociate and lead to emboli sent distally. Carotid artery tearing, plaque obstruction, or emboli from plaque or carotid artery spasm, bleeding into the carotid wall, can all lead to stroke. Information related to these causes can be derived from B mode imaging.

Complimentary to B mode imaging, color flow Doppler can reveal blood flow direction and mean velocity of flow and is very useful for imaging stenosis or obstruction and the site within the vessel. At various levels of the carotid artery, the peak and mean flow velocities, resistance, and actual arterial wave on spectral imaging provides quantitative numbers for determination of obstruction and stenosis of the internal carotid artery. All elements of the carotid Doppler examination as well as information on the vertebral arteries in the neck can be rapidly accessed and used for rapid evaluation of stroke, its cause, and potential intervention. Other arteries can be assessed in the neck as part of the internal carotid artery examination.

3D Carotid Doppler

In another embodiment, multiple 2D carotid images can be rapidly obtained through a carotid ultrasound device and processed and reconstructed into a 3D or 3 dimensional image of the carotid artery. The latter incorporates B mode and color flow Doppler. Rapid identification of stenosis and obstruction can be demonstrated with combined individual 2D internal carotid Doppler and separate 3D carotid Doppler.

Transcranial Doppler

Transcranial Doppler (TCD) is a test that measures the velocity of blood flow through the brain's blood vessels, usually the mean blood flow velocity. Blood flow velocity is recorded by emitting a high-pitched sound wave from the ultrasound probe, which then bounces off of various materials to be measured by the same probe. A specific frequency is used (usually close to 2 MHz), and the speed of the blood in relation to the probe causes a phase shift, wherein the frequency is increased or decreased. This frequency change directly correlates with the speed of the blood, which is then recorded electronically for later analysis. Normally a range of depths and angles must be measured to ascertain the correct velocities.

For transcranial Doppler, the site of insonation determines the potential vessels to be sampled, i.e. pre-temporal for example is for middle cerebral arteries or anterior cerebral arteries. This technique is an indirect measure and depth of insonation by power m mode is directly related to the position on a specific artery.

Because the bones of the skull block the transmission of ultrasound, regions with thinner walls insonation windows can be used for analyzing. For this reason, recording is performed in the temporal region above the cheekbone/zygomatic arch, through the eyes, below the jaw, and from the back of the head. Patient age, gender, race and other factors affect bone thickness, making some examinations more difficult or even impossible. Most can still be performed to obtain acceptable responses, sometimes requiring using alternate sites from which to view the vessels.

Transcranial Doppler is a real time technique that is sensitive and specific for blood flow velocity in multiple medium and large blood vessels of the brain over a broad range of velocities, able to determine brain blood vessel resistance, useful in determining collateral flow presence and efficacy and cerebral atherosclerosis, able to compare blood flow in blood vessels in comparison from one side of the brain to the other, is the only technique available for brain emboli detection, and can reliably predict vessel obstruction. Transcranial Doppler images can give specific artery and within artery information on mean flow velocity, flow direction, and obstruction and stenosis. Wave analysis on spectral flow is also useful in defining site of stenosis or obstruction as well as efficacy of blood flow. Transcranial Doppler analysis follows a sequential analysis of the ophthalmic vessels, the vessels in the anterior circulation, noted pre-temporally, and the posterior circulation at the back of the head, with continuous listening for bruits and atherosclerosis and also emboli followed by prolonged emboli detection. Specific abnormalities in the waveform and also specific velocities may be associated with obstruction and stenosis when compared to normal age related standards for specific vessels.

Eye patch transcranial Doppler probes may be applied to the eyelids to sample the ophthalmic arteries bilaterally and transcranial probes will be used in the pre-temporal region to evaluate the middle and anterior cerebral arteries and other arteries bilaterally and in the back of the head to evaluate the basilar artery and vertebral arteries and other arteries (see, e.g., PCT Application No. PCT/US2013/067713, U.S. patent application Ser. No. 14/674,411; (C) U.S. patent application Ser. No. 14/070,264; (D) U.S. patent application Ser. No. 14/084,039; (E) U.S. Provisional Application No. 61/720,992; (F) U.S. Provisional Application No. 61/794,618; and (G) U.S. Provisional Application No. 61/833,802). The transcranial Doppler probes will be incorporated in the pre-temporal region and in the back of head (suboccipitally) into the helmet (see, e.g., FIGS. 3A, 5 & 6; paragraphs [0079], [0081] & [0082] of U.S. patent application Ser. No. 14/674,411, which are incorporated herein by reference). Transcranial Doppler mean blood flow velocity in major cerebral arteries represents an indirect assessment of cerebral perfusion. Changes in cerebral blood flow can be inferred from changes in blood flow velocity; however, there are limitations in that a constant vessel diameter and specific angle of insonation are assumed. Transcranial Doppler cannot measure perfusion abnormalities at the microcirculatory level but large vessel territory perfusion abnormalities are relevant in stroke definition and determination for intervention. Operator expertise has limited transcranial Doppler but is obviated by the embodiments of the helmet and probe design.

Transcranial Color Coded Doppler (TCCD)

Similar to transcranial Doppler (TCD), transcranial color-coded Doppler can be used to interrogate brain blood vessels for velocity and other measures. The difference with TCCD versus TCD is that in the former, the large and potentially medium sized vessels can actually be seen. Transcranial Doppler infers information on vessels based on their location and depth and other parameter without direct visualization. For TCCD, similar to carotid 2D and 3D Doppler, a picture of the vessel with potential changes with or without stenosis or obstruction can be seen. In an exemplary embodiment, this may be employed as a primary or additional measure for evaluating the large and potentially medium vessels of the brain in stroke and in traumatic brain injury. In an exemplary embodiment, transcranial Doppler and transcranial color Dopplers can be deployed and used within the ambulance for identification of large vessel stenosis, obstruction, as well as other measures and collateral brain circulation. In an exemplary embodiment, transcranial Doppler can be used to obtain other measures that reflect on brain intracranial pressure and vessel reactivity that can reflect on conditions of increased brain pressure, related to traumatic brain injury, brain swelling from many causes, or large stroke with brain swelling.

Phased Array

Phased Array Ultrasound enables the use of multiple transducers to be pulsed and readout independently. Having an array of such devices enables beam steering, beam forming, and higher resolution imaging upon return of the reflected/scattered ultrasound. Due to the larger receiving aperture, the beam can be electronically steered, and then read back for that part of space interrogated by the smaller beam size enabled by the phased array beam-forming algorithms. Such devices are used in Medical Imaging and in many industrial applications. Typically, because of the much higher resolution afforded by MRI and CT scanning devices, phase array ultrasound has not been used in the brain. However, when larger structures are imaged, such as major vasculature, and superb resolution is not desired, phased array ultrasound is adequate. In particular, phased array ultrasound can fit into a small box, of size 10"×10"×3", and be part of an ambulances or Emergency Department or other medical settings, equipment, as compared to the room-size MRI's and CT scanning systems in common use. Phased array has been used to look at brain blood flow velocities, similar to transcranial Doppler and the probes could be placed in similar positions to transcranial Doppler probes.

Phased array probes may be used to replace transcranial Doppler probes. This can provide beam steering capacities that may increase the procurement of brain vessel data. In an exemplary embodiment, in addition to external use within the helmet, a phased array probe or transcranial Doppler probe is combined with an optoacoustic or photoacoustic probe to provide physiological vessel flow data, reflective of stenosis or obstruction, and oxygenation information on contiguous brain tissue that is supplied by these vessels (See below). It should be appreciated that probes and transducers are synonymous and can be used interchangeable in the application, and the probes of the invention and could be carotid probes, transcranial probes, phased array or photoacoustic spectroscopy probes.

Photoacoustic Spectroscopy

Photoacoustic spectroscopy may be used as part of the evaluation of oxygen and oxygenation externally in some embodiments. For example, probes for this would be added to the existing head parts of the helmet (not shown). Further, as part of this embodiment, a photoacoustic head would be part of the transcranial Doppler and phased array multi-head probes that would be used in intravascular evaluation in connection with cerebral angiography and interventional catheter based intra-arterial therapy with clot buster or clot removal/stenting. Photoacoustic spectroscopy is the measurement of the effect of absorbed electromagnetic energy (particularly of light) on matter by means of acoustic detection.

Photoacoustic imaging is based on the photoacoustic effect. In photoacoustic imaging, non-ionizing laser pulses are delivered into biological tissues (when radio frequency pulses are used, the technology is referred to as thermoacoustic imaging).

Some of the delivered energy will be absorbed and converted into heat, leading to transient thermoelastic expansion and thus wideband (e.g., MHz) ultrasonic emission. The generated ultrasonic waves are then detected by ultrasonic transducers. Computer systems of the invention convert these waves into images. It is known that optical absorption is closely associated with physiological properties, such as hemoglobin concentration and oxygen saturation.

Hemoglobin (Hb or Hgb) is the iron-containing oxygen-transport metalloprotein in the red blood cells of most vertebrates. Hemoglobin in the blood carries oxygen from the respiratory organs (lungs or gills) to the rest of the body (i.e. the tissues) where it releases the oxygen to burn nutrients to provide energy to power the functions of the organism, and collects the resultant carbon dioxide to bring it back to the respiratory organs to be dispensed from the organism.

In general, hemoglobin can be saturated with oxygen molecules (oxyhemoglobin), or desaturated with oxygen molecules (deoxyhemoglobin). Oxyhemoglobin is formed during physiological respiration when oxygen binds to the heme component of the protein hemoglobin in red blood cells. This process occurs in the pulmonary capillaries adjacent to the alveoli of the lungs. The oxygen then travels through the blood stream to be dropped off at cells where it is utilized as a terminal electron acceptor in the production of ATP by the process of oxidative phosphorylation. It does not, however, help to counteract a decrease in blood pH. Ventilation, or breathing, may reverse this condition by removal of carbon dioxide, thus causing a shift up in pH. In this embodiment both as part of the external headset apparatus or the brain intra-arterial set of probes, photoacoustic spectroscopy would be used to evaluate oxygenation, tissue efficacy, and as part of the determination of cerebral perfusion in combination with transcranial Doppler and phased array ultrasound and special fluorescent intravascular injection.

Vasculature and Perfusion Measurement

Perfusion may be used and is the process of delivery of blood to a capillary bed in the biological tissue. Vasculature and perfusion measurements in the brain perfusion (more correctly transit times) can be estimated with contrast-enhanced computed tomography or MR angiography. To get a better representation of the blood flow in the brain, a dye is injected into the patient to enhance visualization of the suspect area. Cerebral perfusion measurements are based on quantitative measures of cerebral blood flow, mean transit time (MTT), or time to peak flow (TTP) and cerebral blood volume (CBV). In some embodiments, brain perfusion in specific regions of potential completed stroke and penumbral regions with still preserved function will involve transcranial Doppler, phased array, photoacoustic spectroscopy, and ICN dye.

Tissue plasminogen activator (tPA) or clot buster is used in diseases that feature blood clots, such as stroke, pulmonary embolism, myocardial infarction, in a medical treatment called thrombolysis. To be most effective in ischemic stroke, tPA must be administered as early as possible after the onset of symptoms. Protocol guidelines require its use intravenously within the first three hours of the event (in some cases up to 4.5 hours), after which its detriments may outweigh its benefits. tPA can either be administered systemically or administered through an arterial catheter directly to the site of occlusion in the case of peripheral arterial thrombi and thrombi in the proximal deep veins of the leg. In some embodiments, the methods and devices include introducing iPA intravenously or intra-arterially into a patient after assessing a patient for a stroke and evaluating for potential risk of this therapy in each specific patient situation.

A transcranial Doppler photoacoustic device can be used to transmit a first energy to a region of interest at an internal site of a subject is disclosed (the entire inside of the skull is illuminated, and produces sound waves, proportional to the absorption of incident light). The method comprises the steps outputting optical excitation energy to said region of interest and heating said region, causing a transient thermoelastic expansion and producing a wideband ultrasonic emission. A phased-array transducer system records the ultrasonic waves. Computer systems of the invention convert the waves into images. Because all of the transducers record simultaneously, the device can image the whole brain area simultaneously.

By providing at least one, or a plurality of one or two dimensional detectors, the detectors receive wideband ultrasonic emission. An oxygen level is computed of said region of interest from said wideband ultrasonic emission. Then, an array of ultrasound transducer elements output a beam pattern from said array of ultrasound transducer elements to insonate a region of interest at an internal site in a body, where the beam output pattern is sufficiently large to comprise a multi-beam pattern. Multiple receiver elements insonate over a substantially simultaneous period by directing energy produced by said array of ultrasound transducer elements into said region of interest in said body, and adjusting an amplitude of energy output by said array of transducers to cause the beam pattern output to have a generally flat upper pattern and nulls in a grating lobe region. This would be performed by the user with the device and associated software.

Then a propagation time delay is introduced and the beam pattern output from said array of ultrasound transducer elements, wherein the propagation delay increases as a distance increases from a central output area of said array of ultrasound transducer elements produces an image of said internal site. In addition, in software during reconstruction, phase shifts can be selectively added to all of the signals so that the reconstructed beam scans the whole brain cavity.

The photoacoustic technology deployed can use an unfocused detector to acquire the photoacoustic signals and the image is reconstructed by inversely solving the photoacoustic equations. Alternatively, the transcranial Doppler photoacoustic device of this embodiment may use a spherically focused detector with 2D and 3D point-by-point scanning and would require a reconstruction algorithm. Thermoelastic expansion of the blood vessel wall depends on the oxyhemoglobin/deoxyhemoglobin ratio. In order to obtain precise mapping of the area of interest, the Doppler ultrasound functionality of the device is utilized to provide an image to the user.

Dye can be administered to a patient to visualize the brain vasculature and a perfusion measurement can be made in various regions of the brain along with the transcranial Doppler and the photoacoustic screening.

The photoacoustic technology deployed in this device uses an unfocused detector to acquire the photoacoustic signals and the image is reconstructed by inversely solving the photoacoustic equations. Alternatively, the transcranial Doppler photoacoustic device of this embodiment may use a spherically focused detector with 2D and 3D point-by-point scanning and would require a reconstruction algorithm, that operates in near real-time or after data acquisition is complete. Thermoelastic expansion of the blood vessel wall depends on the oxyhemoglobin/deoxyhemoglobin ratio. In order to obtain precise mapping of the area of interest, the Doppler ultrasound functionality of the devise is utilized to provide an image to the user.

A laser-induced photoacoustic tomography (PAT) device (photoacoustic spectroscopy) can also be used. PAT retains intrinsic optical contrast characteristics while taking advantage of the diffraction-limited high spatial resolution of ultrasound. This embodiment will also allow for imaging hyperoxia-and hypoxia-induced cerebral hemodynamic changes. The PAT technology would show oxygenation levels and the phased array Doppler would present blood flow. This embodiment employs an algorithm of using velocities and blood distribution and oxygen level to simultaneously to determine what is going on with neuronal respiration. This algorithm will determine the 12 types of strokes, as treatment is different in a hemorrhagic stroke or an emboli-induced stroke, in that the blood distribution and velocities are far different in each type.

A microwave-based thermoacoustic tomography (TAT) device can be used to image deeply seated lesions and objects in biological tissues and the phased array Doppler or single receiver Doppler would present blood flow. Because malignant tissue absorbs microwaves more strongly than benign tissue, cancers can be imaged with good spatial resolution and contrast.

Phased array Doppler can be used to present blood flow using multiple wavelength photoacoustic measurements. Oxoborinic acid (Hb02) is the dominant absorbing compounds in biological tissues in the visible spectral range, multiple wavelength photoacoustic measurements can be used to reveal the relative concentration of these two chromophores (the part of a molecule responsible for its color). Thus, the relative total concentration of hemoglobin (HbT) and the hemoglobin oxygen saturation (s02) can be derived. Therefore, cerebral hemodynamic changes associated with brain function can be successfully detected with PAT. For example, under a hyperoxia status, the averaged s02 level, in the areas of imaged cortical venous vessels of brain is higher than that under the normoxia status.

Compounds in vascular walls can be excited by either phased array Doppler or the PAT. This would allow the analysis of the atheroma (plaque) on the linings of certain compounds on vasculature walls.

Ultrasonic transducers can be configured in different patterns to aid in the reception of the photoacoustic signal, for example (but not limited to), the transducers can be set up in an 8 by 8 array.

An algorithm deployed as software, firmware or hardware can be used to produce data which can utilized to produce an image of the biological tissue. In an another embodiment, a tunable laser would be utilized for subtraction and comparison differential imaging to see emboli, say in the carotid artery, or subclavian artery, which are not underneath the skull or any additional areas of interest.

Different frequencies of light of the laser can be used to excite vascular wall, gaseous emboli, and fatty emboli, in superficial or deeper vasculature, both in the skull or the general circulation, to determine probability or likelihood of stroke or other vascular disorder.

Transcranial Doppler can be used to detect emboli in the brain. Emboli may be gaseous or particulate. Examples of emboli include calcium, fat, platelets, red blood cells, clots, or other substances that travel through the bloodstream and lodges in a blood vessel. A stroke or transient ischemic attacks (TIA) involve brain tissue damage that results from the obliteration of blood flow with reduced oxygen delivery through specific extracranial vessels, i.e. carotid arteries, cervical vertebral arteries, or intracranial vessels, i.e. middle cerebral arteries, posterior cerebral arteries due to atherosclerotic vessel change, emboli, or a combination of both. The size of these embolic components is approximately 50 microns for particulate or solid emboli and 1-10 microns for gaseous emboli. Particulate emboli may have a more important role in stroke or TIA causation, as compared to gas emboli; this underlies a need for detection and differentiation of particulate versus gas emboli.

Cerebral emboli may be associated with cardiac, aorta, neck and intracranial vessel disease, as well as coagulation disorders and neck and during diagnostic and surgical procedures on the heart and the carotid arteries. Cerebral embolism can be a dynamic process episodic, persistent, symptomatic, asymptomatic, and may, but, not in all cases, predispose to stroke or TIA, influenced to some degree by composition and size; the latter embolic stroke, which is influenced by the vessel and its diameter to which the embolus goes.

Raman Spectroscopy

In one or more exemplary embodiments, an application of infrared light, modulated at 200 kHz to 30 MHz frequencies can be used to excite contrast agents or certain molecules in the brain and release ultrasound waves. This can be applied behind the skull, in blood cells, in tissue, and in serum or plasma. This application combines photoacoustic and ultrasound methodology. Raman infrared wavelengths of approximately 10 microns are used to make a photo-acoustic image. Raman methodology is able to distinguish hemoglobin with oxygen from hemoglobin without oxygen, as well as specific proteins, mRNA molecules, microRNA molecules, and look at specific DNAs. Raman spectroscopy can also define small point mutations in a DNA molecule in patients that may different from normal as well as variants called SNPs or restriction length polymorphisms that may be involved in disease pathogenesis. Raman can therefore be used for genetic profiling or to define abnormalities that may cause or underlay specific diseases. In traumatic brain injury and stroke, specific molecules may rise or change, in specific types or subsets of these disorders, including concussion and large vessel obstruction strokes. Stroke may also be associated with certain genetic abnormalities or SNPs that warrant detection for therapy preventatively. In one or more exemplary embodiments, Raman Spectroscopy in the pre-hospital and non-emergent situations can be employed.

Other measurement techniques have been used in non-urgent situations and can be used in real-time in traumatic brain injury and concussion for qualitative and quantitative molecular biomarkers and potential diagnosis of traumatic brain injury, concussion, and other brain disorders. These measurements techniques including, for example (but not limited to), Western blot technology, genomic, proteomic, metabolomic, lipidomic, and other methodologies. Similar methodologies and molecules have been identified in specific stroke types using proteomic, metabolomic, molecular biological/genetic tools. In traumatic brain injury, concussion, stroke, other brain disorders, and non-brain medical disorders, these biomarkers can be identified in blood, blood cells, serum, plasma, cerebrospinal fluid, urine, and brain and other tissues. In an exemplary embodiment, these tools will be combined with Raman Spectroscopy for point-of-care diagnostics with other point-of-care molecular analysis devices for diagnosis of stroke, traumatic brain injury, concussion, and other neurological and medical disorders.

Traumatic Brain Injury and Concussion

At least 1.7 M individuals per year may sustain traumatic brain injury and concussion and 20% of military personnel may sustain traumatic brain injury, including but not limited to blast injury, concussion and/or major traumatic brain injury. Early on, this may involve alteration of consciousness, seizures, weakness of both or one side of the body, inability to speak or understand speech and other neurological dysfunction and death. Sequelae of traumatic brain injury include severe neurological disability, seizures, learning disability, mood disorder, suicide, post-traumatic stress disorder, other psychiatric disorders, memory disorder, cognitive disorders, and dementia. The early clinical disorders and abnormalities in traumatic brain injury can be predicated on neuronal dysfunction and death, brain swelling, brain immunological responses, large neck or brain spasm of vessels with narrowing of vessels and reduced blood flow, large neck or blood vessel tearing (dissection) large or small brain bleeds (hemorrhage) within the brain substance, other bleeding including bleeds into spaces that surround the brain, i.e., subarachnoid bleeds, epidural and subdural bleeds (hematoma). Early diagnosis and early appropriate treatment of traumatic brain injury, similar to stroke, is essential to delimit morbidity and mortality and to prevent neurological and psychiatric sequelae. In the acute phase of traumatic brain injury (TBI), neurological and other clinical examination, evaluation for brain and neck blood vessel obstruction or tearing, i.e., dissection, evaluation of shifts in the brain contents due to blood or swelling (edema), and vessel spasms, can be evaluated in real time with telemedicine neurological and other clinical examination and including, but not limited to, carotid Doppler and transcranial Doppler, and by specific traumatic brain injury molecular measures can be done. The carotid Doppler can detect vessel obstruction and vessel tearing. The transcranial Doppler can detect brain vessel obstruction, emboli, vessel spasm, and abnormalities in vessel reactivity. The latter can be an earlier and specific detector for concussion. In an exemplary embodiment, these measures can be done and also an expansion of the device has the capacity to detect shift in brain content due to edema or hemorrhage. In an exemplary embodiment, neurological and other clinical examination, transcranial Doppler, and/or carotid Doppler can be performed to allow for early diagnosis, early treatment, similar to stroke. In an exemplary embodiment, this data can be interfaced with other devices in this disclosure, including, for example (but not limited to), the devices discussed in paragraph [00261] below.

Inclusions and Exclusions for Stroke Acute Treatment.

Well-established national and international criteria are recommended and/or required screened, in acute stroke, where there is consideration for clot buster, tPA or endovascular clot removal. These include a standard questionnaire that determines the time last known normal. tPA is generally not warranted if the patient had stroke symptoms or was last known well at 3 hours and potentially up to 4.5 hours. For endovascular intervention, 6-8 hours from time of last known well, but this can be longer, based on local criteria (up to 12-16 hours) is used. If these times are exceeded, then these types of therapies, e.g., clot buster, endovascular clot removal, are not clinically warranted. Exclusions include but are not limited to elevated clotting profiles, use of anticoagulants, prior recent major surgery or head injury. Elevated blood pressure of 180 systolic or above, if not corrected, is an exclusion for clot buster, tPA. Relative exclusions may be diabetes or age over 80 years. Each case is different and warrants expert neurological and radiological evaluation for decision making. Given the importance of time for potential reversal of brain injury or preservation of brain function in stroke, any means that will reduce time to diagnosis and treatment is useful. In an exemplary embodiment, this is clinical information that will be collected and be part of the clinical notes generated by neurologists and radiologists through the operations center as part of the telemedicine system. Blood drawing within the ambulance or moving vehicle, may limit one step that requires time, at the receiving hospital. Blood analysis for glucose, full chemistry panel, blood count, blood coagulation profiles, and other standard blood are part of the standard needed studies. Other bodily fluids may also be analyzed. The actual determination of the blood results within an ambulance with ambulance blood laboratories has been established and promotes earlier diagnosis, exclusions, and treatment decisions. In an exemplary embodiment, when these are available, the results and data form this blood analysis can be reviewed and transmitted with the telemedicine system disclosed herein as part of earlier diagnosis and a change in the process and logistics for stroke care.

Establishment of Brain Hemorrhage in Stroke and Traumatic Brain Injury.

13-15% of strokes are hemorrhagic. Hemorrhage is an absolute exclusion for clot buster, tPA. Endovascular clot retrieval is not a part of the treatment pathway for non-hemorrhagic stroke. However, the identification of hemorrhage has required a CT scan or less likely, a MRI scan of brain. In some cases, a spinal tap is also required to rule in or rule out a bleed. A device that could detect blood by ultrasound or other measures would be useful, particularly in the ambulance or other moving vehicle, to determine appropriate treatment for the receiving hospital. In an exemplary embodiment, the telemedicine system can interact or include such a device or can interface to an existing device. An ambulance CT scan can be definitive to determine brain hemorrhage. As such, a small number of ambulances with head CT scanners have recently been deployed. These are limited by expense and geography, requiring proximity to a major tertiary medical center. However, when utilized, the head CT scanners can identify a brain bleed and, when combined with a neurological examination and general blood profiles with clotting measurements, can lead to the administration of a clot buster in the ambulance, with earlier stroke treatment, prehospitally. However, these ambulances are limited by the connectivity and quality and delivery of the imaging data of the neurological examination and imaging examination. In an exemplary embodiment, the telemedicine system can operate and interact with ambulance CT systems to allow for improvement or resolution of the connectivity, quality of service, and delivery of imaging data. Additionally, neurosurgery notification and involvement are essential for preventing, diagnosing and/or treating hemorrhagic stroke. In a further exemplary embodiment, the telemedicine system provides for real time communication with and determination by a medical personnel (such as a neurosurgeon) regarding a patient. With the telemedicine system, the medical personnel can communicate and determine in real time appropriate hospital delivery, hospital preparation and/or neurosurgical direct involvement based on real time transmitted blood data.

In an exemplary embodiment, the telemedicine system can also be used to collect and transmit direct video and audio information and data from one or more devices that reflect on brain function and other organ systems, including, but not limited to, brain wave or Electroencephalogram (EEG) data using one or more EEG devices, for example (but not limited to), Brainscope's Ahead™ 300, the ElMindA device and/or other EEG devices for evaluation for seizures, traumatic brain injury, concussion, and other brain disorders; one or more devices that measure brain blood flow, for example (but not limited to), C-FLOW™ (Ornim), or brain oxygenation; one or more brain pressure measurement devices, for example (but not limited to), Cerepress™ (Third Eye Diagnostics); one or more potential brain hemorrhage detection devices, for example (but not limited to), INFRASCANNER; one or more ultrasound devices that can look at the thickness or anatomy of the optic nerves for brain pressure; one or more ultrasound devices that evaluate heart and other organs, eye movement analysis devices for TBI and other neurological disorders; one or more telemedicine otoscopes or viewing devices for ear disease or signs of TBI with bleeding in the ear as well as pupillary response, for example (but not limited to), Firefly wireless digital video otoscope; one or more telemedicine ophthalmoscopes that look externally and internally into the eye and its optic disc and retina; one or more devices that use telemedicine to auscultate or listen to the heart or lungs, for example (but not limited to), Thinklabs digital stethoscope; one or more blood pressure measurement devices that accurately measure blood pressure with application to high and low blood pressure disorders; an intracranial pressure measurement device; brain hemorrhage diagnostic device, non-brain diagnostic device, blood diagnostic test device; bodily fluid diagnostic test device, or a combination thereof. The telemedicine system can also be used in combination with machine learning and other artificial intelligence to compliment and augment the direct telemedicine and device analysis for stroke blood vessel measurements and other physiological measurements.

In an exemplary embodiment, the telemedicine system is a system of connectivity and quality of service that can be applied to non-medical environments in rural, urban, extreme rural, maritime, and/or aviation environments for observing and evaluating equipment and for transmitting data from equipment for efficacy and malfunction assessment.

The aforementioned description of the specific aspects will so fully reveal the general nature of the disclosure that others can, by applying knowledge within the skill of the art, readily modify and/or adapt for various applications such specific aspects, without undue experimentation, and without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

References in the specification to "one aspect," "an aspect," "an exemplary aspect," etc., indicate that the aspect described may include a particular feature, structure, or characteristic, but every aspect may not necessarily include the particular feature, structure, or characteristic. Moreover, such phrases are not necessarily referring to the same aspect. Further, when a particular feature, structure, or characteristic is described in connection with an aspect, it is submitted that it is within the knowledge of one skilled in the art to affect such feature, structure, or characteristic in connection with other aspects whether or not explicitly described.

The exemplary aspects described herein are provided for illustrative purposes, and are not limiting. Other exemplary aspects are possible, and modifications may be made to the exemplary aspects. Therefore, the specification is not meant to limit the disclosure. Rather, the scope of the disclosure is defined only in accordance with the following claims and their equivalents.

Aspects may be implemented in hardware (e.g., circuits), firmware, software, or any combination thereof. Aspects may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general purpose computer.

For the purposes of this discussion, the term "processor circuitry" shall be understood to be circuit(s), processor(s), logic, or a combination thereof. For example, a circuit can include an analog circuit, a digital circuit, state machine logic, other structural electronic hardware, or a combination thereof. A processor can include a microprocessor, a digital signal processor (DSP), or other hardware processor. The processor can be "hard-coded" with instructions to perform corresponding function(s) according to aspects described herein. Alternatively, the processor can access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary aspects described herein, processor circuitry can include memory that stores data and/or instructions. The memory can be any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

As will be apparent to a person of ordinary skill in the art based on the teachings herein, the communication protocols of the exemplary embodiments are not limited, and can include, for example, Long-Term Evolution (LTE), and can be applied to other cellular communication standards, including (but not limited to) Evolved High-Speed Packet Access (HSPA+), Wideband Code Division Multiple Access (W-CDMA), CDMA2000, Time Division-Synchronous Code Division Multiple Access (TD-SCDMA), Global System for Mobile Communications (GSM), General Packet Radio Service (GPRS), Enhanced Data Rates for GSM Evolution (EDGE), and Worldwide Interoperability for Microwave Access (WiMAX) (Institute of Electrical and Electronics Engineers (IEEE) 802.16) to provide some examples. Further, exemplary aspects are not limited to cellular communication networks and can be used or implemented in other kinds of wireless communication access networks, including (but not limited to) one or more IEEE 802.11 protocols, Bluetooth, Near-field Communication (NFC) (ISO/IEC 18092), ZigBee (IEEE 802.15.4), and/or Radio-frequency identification (RFID), to provide some examples. Further, exemplary aspects are not limited to the above wireless networks and can be used or implemented in one or more wired networks using one or more well-known wired specifications and/or protocols.

What is claimed is:

1. A telemedicine system operable to communicate with a remote operations center, comprising:
    a router having at least two or more transceivers configured to transmit and receive one or more communications via at least two or more antennas; wherein a first antenna is configured to communicate using cellular communications and a second antenna is configured to communicate using satellite communications;
    a controller connected to the at least two or more transceivers configured to establish, via the router, a telemedicine session with an operations center;

at least one or more medical measurement devices operably connected to the controller and configured to provide medical information of a patient during the telemedicine session; and wherein the router masks one or more transient network degradations of the telemedicine session by dynamically switching communications between the at least two or more antennas from an antenna having high packet loss or latency to an antenna having lower packet loss or latency.

2. The telemedicine system of claim 1, wherein the controller is configured to provide an interface to the router for adjusting parameters related to when dynamically switching communications occurs.

3. The telemedicine system of claim 1, wherein the telemedicine system is configured to encrypt communications of the telemedicine session.

4. The telemedicine system of claim 1, further comprising a VSAT terminal configured to transmit data over a Ku or Ka band antenna and a Broadband active or BGAN terminal configured to transmit data over an L-Band antenna.

5. A vehicle comprising the telemedicine system of claim 4, a plurality of wheels, and a motor configured to drive the plurality of wheels.

6. The telemedicine system of claim 1, wherein the at least two or more antennas include an omnidirectional MIMO antenna configured to establish satellite communications with at least one of a low earth orbit satellite or a geostationary satellite at one time.

7. The telemedicine system of claim 1, wherein the telemedicine system is configured to communicate using a protocol that provides capabilities for at least one of rate-limit or traffic prioritization.

8. The telemedicine system of claim 3, wherein the encryption is HIPAA compliant.

9. The telemedicine system of claim 1, further comprising at least two antennas configured to conduct cellular communications and are mounted in a vertical alignment and horizontal alignment, respectively.

10. The telemedicine system of claim 6, wherein the omnidirectional MIMO antenna is further configured to receive GPS, and communicate using cellular communications.

11. The telemedicine system of claim 1, wherein the controller is configured to adjust data send rate of the telemedicine session to reduce packet loss and reduce the resending of packets prior to dynamically switching communications.

12. The telemedicine system of claim 1, wherein the at least one or more medical measurement devices comprises a raman spectroscope configured to perform molecular analysis by raman spectroscopy and/or other molecular diagnostic techniques, the molecular analysis being performed on at least one of: serum, plasma, blood, blood cells, cerebrospinal fluid, urine, cells, and tissue of the patient, wherein the controller is configured to diagnose, based on the molecular analysis, the patient suffering from at least one of the following medical conditions: acute stroke, acute stroke subtype, concussion, and traumatic brain injury.

13. The telemedicine system of claim 9, wherein the at least two antennas configured to conduct cellular communications are enclosed in a single radome.

14. The telemedicine system of claim 1, further comprising:

at least one or more medical imaging modalities operably connected to the controller and configured to generate one or more medical images of the patient during the telemedicine session.

15. A telemedicine system operable to communicate with a remote operations center and one or more medical facilities, comprising:

a router having at least two or more transceivers configured to transmit and receive one or more communications via at least two or more antennas; wherein a first antenna is configured to communicate using cellular communications and a second antenna is configured to communicate using satellite communications;

a controller connected to the at least two or more transceivers configured to establish, via the router, a telemedicine session with an operations center;

at least one or more medical measurement devices operably connected to the controller and configured to provide medical information of a patient to the controller for use during the telemedicine session;

at least one or more multimedia equipment operably connected to the controller and configured to generate real-time audio and video information to the controller for use during the telemedicine session;

wherein the router masks one or more transient network degradations of the telemedicine session by dynamically switching communications between the at least two or more antennas from an antenna having high packet loss or latency to an antenna having lower packet loss or latency.

16. The telemedicine system of claim 15, wherein the controller is configured to provide an interface to the router for adjusting parameters related to dynamically switching communications.

17. The telemedicine system of claim 15, wherein the controller is configured to encrypt communications of the telemedicine session such that the telemedicine session is a secure telemedicine session.

18. The telemedicine system of claim 15, further comprising a VSAT terminal configured to transmit data over a Ku or Ka band antenna and a Broadband active or BGAN terminal configured to transmit data over an L-Band antenna.

19. The telemedicine system of claim 15, wherein the at least two antennas include an omnidirectional MIMO antenna configured to establish satellite communications with at least one of a low earth orbit satellite or a geostationary satellite at one time.

20. The telemedicine system of claim 15, wherein the telemedicine system is configured to communicate using a protocol that provides capabilities for at least one of rate-limit or traffic prioritization.

21. The telemedicine system of claim 17, wherein the encryption is HIPAA compliant.

22. The telemedicine system of claim 15, further comprising a raman spectroscope configured to perform molecular analysis by raman spectroscopy and/or other molecular diagnostic techniques, the molecular analysis being performed on at least one of: serum, plasma, blood, blood cells, cerebrospinal fluid, urine, cells, and tissue of the patient, wherein the controller is configured to diagnose, based on the molecular analysis, the patient suffering from at least one of the following medical conditions: acute stroke, acute stroke subtype, concussion, and traumatic brain injury.

23. The telemedicine system of claim 22, wherein the molecular analysis increases the precision of the diagnosis.

24. The telemedicine system of claim 15, further comprising at least two antennas configured to conduct cellular communications and are mounted in a vertical alignment and horizontal alignment, respectively.

25. The telemedicine system of claim 19, wherein the omnidirectional MIMO antenna is further configured to receive GPS, and communicate using cellular communications.

26. The telemedicine system of claim 15, further comprising a 2D and 3D carotid Doppler and transcranial Doppler that are connected to the telemedicine system.

27. The telemedicine system of claim 15, wherein the telemedicine system operates in a vehicle in a rural, extreme rural, urban, maritime or aviation environment.

28. The telemedicine system of claim 27, wherein the vehicle is selected from the group consisting of ambulance, helicopter, bus, train, car, boat, oil rig, and airplane.

29. The telemedicine system of claim 15, wherein the controller is configured to adjust data send rate of the telemedicine session to reduce packet loss and reduce the resending of packets prior to dynamically switching antennas.

30. The telemedicine system of claim 15, wherein the one or more medical measurement devices is a EEG device, intracranial pressure measurement device, blood pressure measurement device, brain hemorrhage diagnostic device, non-brain diagnostic device, blood diagnostic test device; bodily fluid diagnostic test device, or a combination thereof.

31. The telemedicine system of claim 15, wherein the collected and transmitted audio, video or medical information is reviewed in real-time by at least one physician to diagnosis and/or treat the patient suffering from stroke, a traumatic brain injury, a neurological disorder, an organ system medical disorder, or a combination thereof.

32. The telemedicine system of claim 31, wherein the controller is configured to implement an enhanced transport layer that mitigates high-latency of packets across at least one satellite link and at least one cellular wireless link, and provides Quality of Service (QoS) and wide-area network (WAN) optimization across the at least one satellite link and the at least one cellular wireless link, and wherein the operations center is configured to provide real-time communication between at least one medical personnel in a vehicle with the telemedicine system, the at least one physician, and at least one medical personnel at a receiving hospital.

33. The telemedicine system of claim 15, further comprising at least one teleconferencing solution, the at least one teleconferencing solution is connected to the telemedicine system at an application layer, and rides on top of fully redundant physical, network and transport layers with no single point of failure and with at least 99.99% availability.

* * * * *

UNITED STATES PATENT AND TRADEMARK OFFICE
CERTIFICATE OF CORRECTION

PATENT NO. : 10,534,894 B2
APPLICATION NO. : 15/487955
DATED : January 14, 2020
INVENTOR(S) : Stein et al.

Page 1 of 1

It is certified that error appears in the above-identified patent and that said Letters Patent is hereby corrected as shown below:

On the Title Page

Item (72) Inventor is corrected to read:
-- Stuart Alan Stein, Tucson, (AZ);
Craig Steven Smith, Littleton, (CO);
Jeffrey Holt Stein, Scottsdale, (AZ) --.

Signed and Sealed this
Twelfth Day of May, 2020

Andrei Iancu
*Director of the United States Patent and Trademark Office*